(12) United States Patent
Minshull et al.

(10) Patent No.: US 10,287,590 B2
(45) Date of Patent: May 14, 2019

(54) METHODS FOR GENERATING LIBRARIES WITH CO-VARYING REGIONS OF POLYNULEOTIDES FOR GENOME MODIFICATION

(71) Applicant: DNA2.0, Inc., Menlo Park, CA (US)

(72) Inventors: Jeremy Minshull, Los Altos, CA (US); Sridhar Govindrajan, Los Altos, CA (US); Kedar Patel, Fremont, CA (US)

(73) Assignee: DNA2.0, INC., Newark, CA (US)

( * ) Notice: Subject to any disclaimer, the term of this patent is extended or adjusted under 35 U.S.C. 154(b) by 0 days.

(21) Appl. No.: 14/582,938

(22) Filed: Dec. 24, 2014

(65) Prior Publication Data

US 2015/0225730 A1  Aug. 13, 2015

Related U.S. Application Data

(60) Provisional application No. 61/939,207, filed on Feb. 12, 2014, provisional application No. 61/974,873, filed on Apr. 3, 2014, provisional application No. 62/075,601, filed on Nov. 5, 2014.

(51) Int. Cl.
*C12N 15/66* (2006.01)
*C12N 15/64* (2006.01)

(52) U.S. Cl.
CPC ............. *C12N 15/66* (2013.01); *C12N 15/64* (2013.01)

(58) Field of Classification Search
None
See application file for complete search history.

(56) References Cited

U.S. PATENT DOCUMENTS

| | | | |
|---|---|---|---|
| 4,994,370 A * | 2/1991 | Silver .................... | C12N 15/10 435/15 |
| 5,128,256 A * | 7/1992 | Huse et al. .................. | 435/472 |
| 8,697,359 B1 * | 4/2014 | Zhang ..................... | C12N 15/85 424/94.1 |
| 2006/0246452 A1 * | 11/2006 | Gonda et al. ..................... | 435/6 |
| 2014/0068797 A1 * | 3/2014 | Doudna ................ | C12N 15/102 800/18 |

FOREIGN PATENT DOCUMENTS

| WO | WO 13/169398 A2 | 11/2013 |
|---|---|---|
| WO | WO 13/169398 A3 | 11/2013 |
| WO | WO 13/169802 A1 | 11/2013 |
| WO | WO 13/176772 A1 | 11/2013 |
| WO | WO 14/018423 A2 | 1/2014 |

OTHER PUBLICATIONS

Dicarlo et al., "Genome engineering in *Saccharomyces cerevisiae* using CRISPR-Cas systems," Nucleic Acids Research, 41(7):4336-4343, (2013).
Jinek et al., "A Programmable Dual-RNA-Guided DNA Endonuclease in Adaptive Bacterial Immunity," Science, 337:816-821, (2012).
Le Cong et al., "Multiplex Genome Engineering Using CRISPR/Cas Systems," Science, 339:819-823, DOI: 10.1123/science. 1231143, 6 pages, (2013).
Mali et al., "CAS9 transcriptional activators for target specificity screening and paired nickase for cooperative genome engineering," Nature Biotechnology, Letters (2013).
Ran et al., "Double Nicking by RNA-Guided CRISPR Cas9 for Enchanced Genome Editing Specificity," Cell, 154-1380-1389, (2013).
Sanjana et al., "Improved vectors and genome-wide libraries for CRISPR screen," Nature Methods, 11(8):783-784, (2014).
Shalem et al., "Genome-Scale CRISPR-Cas9 Knockout Screening in Human Cells," Scienceexpress, 7 pages, DOI:10.1126/science. 1247005, (2013).
Wang et al., "Genetic Screens in Human Cells Using the CRIPSR-Cas9 System" Science, 343:80-84, DOI:10.1126/science.1246981, (2014).

* cited by examiner

*Primary Examiner* — Anne M. Gussow
*Assistant Examiner* — James S Ketter
(74) *Attorney, Agent, or Firm* — Alston & Bird LLP

(57) ABSTRACT

The invention provides methods for introducing co-varying paired nucleic acids into a vector such under separate transcriptional control. An oligonucleotide is synthesized including the paired nucleic acids. The oligonucleotide is then assembled with a spacer nucleic acid encoding a promoter. After assembly the spacer nucleic acid is to one side of the oligonucleotide encoding the paired segments. However, on circularization of the assembled nucleic acid and cleavage between the DNA segments the spacer oligonucleotide and its components now occur between the paired segments. The resulting nucleic acid can now be cloned into a vector with a single step, such that each of the paired nucleic acid segments is linked to its own promoter. The present method can readily be extended to library screening without proportionately increasing the effort.

13 Claims, 14 Drawing Sheets
Specification includes a Sequence Listing.

SEQUENCE LISTING

```
<160> NUMBER OF SEQ ID NOS: 204

<210> SEQ ID NO 1
<211> LENGTH: 300
<212> TYPE: DNA
<213> ORGANISM: Artificial sequence
<220> FEATURE:
<223> OTHER INFORMATION: Mammalian

<400> SEQUENCE: 1
gctccgcggc acgagaactc aaagcccgg ggcctgggtc ccacgcgggg tcccttaccc      60
agggtgcccc gggcgctcat ttgcatgtcc cacccaacag gtaaacctga caggtcatcg    120
cggccaggta cgacctggcg gtcagagcac caaacatacg agccttgtga tgagttccgt    180
tgcatgaaat tctcccaaag gctccaagat ggacaggaaa gggcgcggtt cggtcaccgt    240
aagtagaata ggtgaaagac tcccgtgcct tataaggcct gtgggtgact tcttctcacc    300

<210> SEQ ID NO 2
```

<211> LENGTH: 300
<212> TYPE: DNA
<213> ORGANISM: Artificial sequence
<220> FEATURE:
<223> OTHER INFORMATION: Mammalian

<400> SEQUENCE: 2

| gcctgaggcg tggggccgcc tcccaaagac ttctgggagg gcggtgcggc tcaggctctg | 60 |
| cccgcctcc gggctatttt gcatacgacc atttccagta attcccagca gccaccgtag | 120 |
| ctatatttgg tagaacaacg agcactttct caactccagt caataactac gttagttgca | 180 |
| ttacacattg aatagaggt taaatctcta ggtcatttaa gagaagtcgg cctatgtgta | 240 |
| cgctaatata agacatttgt tccaggggct ttaaatagct ggtggtggaa ctcaatatcc | 300 |

<210> SEQ ID NO 3
<211> LENGTH: 249
<212> TYPE: DNA
<213> ORGANISM: Artificial sequence
<220> FEATURE:
<223> OTHER INFORMATION: Mammalian

<400> SEQUENCE: 3

| gagggcctat ttcccatgat tccttcatat ttgcatatac gatacaaggc tgttagagag | 60 |
| ataattggaa ttaatttgac tgtaaacaca aagatattag tacaaaatac gtgacgtaga | 120 |
| aagtaataat ttcttgggta gtttgcagtt ttaaaattat gttttaaaat ggactatcat | 180 |
| atgcttaccg taacttgaaa gtatttcgat ttcttggctt tatatatctt gtggaaagga | 240 |
| cgaaacacc | 249 |

<210> SEQ ID NO 4
<211> LENGTH: 300
<212> TYPE: DNA
<213> ORGANISM: Artificial sequence
<220> FEATURE:
<223> OTHER INFORMATION: Mammalian

<400> SEQUENCE: 4

| ggaggcctca cccctacct cggccgctcc aggggcggg cctgcatctg ggccacctct | 60 |
| tttgcatatt ggcacccaca atccaccgcg gctatgaggc cagtataagg cggtaaaatt | 120 |
| acgataagat atgggatttt acgtgatcga agacatcaaa gtaagcgtaa gcacgaaagt | 180 |
| tgttctgcaa cataccactg taggaaatta tgctaaatat gaaaccgacc ataagttatc | 240 |
| ctaaccaaaa gatgatttga ttgaagggct taaaataggt gtgacagtaa cccttgagtc | 300 |

<210> SEQ ID NO 5
<211> LENGTH: 300
<212> TYPE: DNA
<213> ORGANISM: Artificial sequence
<220> FEATURE:
<223> OTHER INFORMATION: Mammalian

<400> SEQUENCE: 5

| aagtccgcgg cacgagaaat caaagccccg gggcctgggt cccacgcggg gtcccttacc | 60 |
| cagggtgccc cggcgctca tttgcatgtc ccacccaaca ggtaaacctg acagatcggt | 120 |
| cgcggccagg tacggcctgg cggtcagagc accaaactta cgagccttgt gatgagttcc | 180 |
| gttacatgaa attctcctaa aggctccaag atgacagga aagcgctcga ttcggttacc | 240 |
| gtaaggaaaa caaatgagaa actcccgtgc cttataagac ctggggacgg acttatttgc | 300 |

-continued

```
<210> SEQ ID NO 6
<211> LENGTH: 19
<212> TYPE: DNA
<213> ORGANISM: Artificial sequence
<220> FEATURE:
<223> OTHER INFORMATION: Mammalian

<400> SEQUENCE: 6
gggcacagat gagaaactc                                               19

<210> SEQ ID NO 7
<211> LENGTH: 20
<212> TYPE: DNA
<213> ORGANISM: Artificial sequence
<220> FEATURE:
<223> OTHER INFORMATION: Mammalian

<400> SEQUENCE: 7
tgaaggtgtg gttccagaac                                              20

<210> SEQ ID NO 8
<211> LENGTH: 19
<212> TYPE: DNA
<213> ORGANISM: Artificial sequence
<220> FEATURE:
<223> OTHER INFORMATION: Mammalian

<400> SEQUENCE: 8
agtccgagca gaagaagaa                                               19

<210> SEQ ID NO 9
<211> LENGTH: 19
<212> TYPE: DNA
<213> ORGANISM: Artificial sequence
<220> FEATURE:
<223> OTHER INFORMATION: Mammalian

<400> SEQUENCE: 9
ccgtttgtac tttgtcctc                                               19

<210> SEQ ID NO 10
<211> LENGTH: 9058
<212> TYPE: DNA
<213> ORGANISM: Artificial sequence
<220> FEATURE:
<223> OTHER INFORMATION: Mammalian

<400> SEQUENCE: 10
gctcttcagt tttagagcta gaaatagcaa gttaaaataa ggctagtccg ttatcaactt    60
gaaaaagtgg caccgagtcg gtgcttttttt gaagacacac cgctctcaat attggccatt   120
agccatatta ttcattggtt atatagcata aatcaatatt ggctattggc cattgcatac   180
gttgtatcta tatcataata tgtacattta tattggctca tgtccaatat gaccgccatg   240
ttggcattga ttattgacta gttattaata gtaatcaatt acggggtcat tagttcatag   300
cccatatatg gagttccgcg ttacataact tacggtaaat ggcccgcctg gctgaccgcc   360
caacgacccc cgcccattga cgtcaataat gacgtatgtt cccatagtaa cgccaatagg   420
gactttccat tgacgtcaat gggtggagta tttacgtaa actgcccact tggcagtaca    480
tcaagtgtat catatgccaa gtccgccccc tattgacgtc aatgacggta aatggcccgc   540
ctggcattat gcccagtaca tgaccttacg ggactttcct acttggcagt acatctacgt   600
attagtcatc gctattacca tgctgatgcg gttttggcag tacaccaatg ggcgtggata   660
```

```
gcggtttgac tcacggggat ttccaagtct ccaccccatt gacgtcaatg ggagtttgtt      720
ttggcaccaa aatcaacggg actttccaaa atgtcgtaat aaccccgccc cgttgacgca      780
aatgggcggt aggcgtgtac ggtgggaggt ctatataagc agagctcgtt tagtgaaccg      840
tcagatcact agaagcttta ttgcggtagt ttatcacagt taaattgcta acgcagtcag      900
gccaacagag accacaccca agctggccgc caccatggcc ccaaagaaga gcggaaggt       960 cggtatccac ggagtcccag cagccgacaa gaagtacagc atcggcctgg ccatcggcac     1020
caactctgtg ggctgggccg tgatcaccga cgagtacaag gtgcccagca gaaaattcaa     1080
ggtgctgggc aacaccgacc ggcacagcat caagaagaac ctgatcggag ccctgctgtt     1140
cgacagcggc gaaacagccg aggccacccg gctgaagaga accgcagaa gaagatacac      1200 cagacggaag aaccggatct gctatctgca agagatcttc agcaacgaga tggccaaggt     1260
ggacgacagc ttcttccaca gactggaaga gtccttcctg gtggaagagg ataagaagca     1320
cgagcggcac cccatcttcg gcaacatcgt ggacgaggtg gcctaccacg agaagtaccc     1380
caccatctac cacctgagaa agaaactggt ggacagcacc gacaaggccg acctgcggct     1440
gatctatctg gccctggccc acatgatcaa gttccggggc cacttcctga tcgagggcga     1500
cctgaacccc gacaacagcg acgtggacaa gctgttcatc cagctggtgc agacctacaa     1560
ccagctgttc gaggaaaacc ccatcaacgc cagcggcgtg gacgccaagg ccatcctgtc     1620
tgccagactg agcaagagca gacggctgga aaatctgatc gcccagctgc cggcgagaa     1680 gaagaatggc ctgttcggaa acctgattgc cctgagcctg ggcctgaccc ccaacttcaa     1740
gagcaacttc gacctggccg aggatgccaa actgcagctg agcaaggaca cctacgacga     1800
cgacctggac aacctgctgg cccagatcgg cgaccagtac gccgacctgt ttctggccgc     1860
caagaacctg tccgacgcca tcctgctgag cgacatcctg agagtgaaca ccgagatcac     1920
caaggccccc ctgagcgcct ctatgatcaa gagatacgac gagcaccacc aggacctgac     1980
cctgctgaaa gctctcgtgc ggcagcagct gcctgagaag tacaaagaga ttttcttcga     2040
ccagagcaag aacggctacg ccggctacat tgacggcgga gccagccagg aagagttcta     2100
caagttcatc aagcccatcc tggaaaagat ggacggcacc gaggaactgc tcgtgaagct     2160
gaacagagag gacctgctgc ggaagcagcg gaccttcgac aacggcagca tcccccacca     2220
gatccacctg ggagagctgc acgccattct gcggcggcag gaagattttt acccattcct     2280
gaaggacaac cgggaaaaga tcgagaagat cctgaccttc cgcatcccct actacgtggg     2340
ccctctggcc aggggaaaca gcagattcgc ctggatgacc agaaagagcg aggaaaccat     2400 cacccctgg aacttcgagg aagtggtgga caagggcgct tccgcccaga gcttcatcga     2460
gcggatgacc aacttcgata agaacctgcc caacgagaag gtgctgccca gcacagcct      2520 gctgtacgag tacttcaccg tgtataacga gctgaccaaa gtgaaatacg tgaccgaggg     2580
aatgagaaag cccgccttcc tgagcggcga gcagaaaag gccatcgtgg acctgctgtt      2640
caagaccaac cggaaagtga ccgtgaagca gctgaaagag gactacttca gaaaaatcga     2700
gtgcttcgac tccgtggaaa tctccggcgt ggaagatcgg ttcaacgcct ccctgggcac     2760
ataccacgat ctgctgaaaa ttatcaagga caaggacttc ctggacaatg aggaaaacga     2820
ggacattctg gaagatatcg tgctgaccct gacactgttt gaggacagag agatgatcga     2880
ggaacggctg aaaacctatg cccacctgtt cgacgacaaa gtgatgaagc agctgaagcg     2940
gcggagatac accggctggg gcaggctgag ccggaagctg atcaacggca tccgggacaa     3000
gcagtccggc aagacaatcc tggatttcct gaagtccgac ggcttcgcca acagaaactt     3060
```

```
catgcagctg atccacgacg acagcctgac ctttaaagag gacatccaga aagcccaggt   3120
gtccggccag ggcgatagcc tgcacgagca cattgccaat ctggccggca gccccgccat   3180
taagaagggc atcctgcaga cagtgaaggt ggtggacgag ctcgtgaaag tgatgggccg   3240
gcacaagccc gagaacatcg tgatcgaaat ggccagagaa aaccagacca cccagaaggg   3300
acagaagaac agccgcgaga gaatgaagcg gatcgaagag ggcatcaaag agctgggcag   3360
ccagatcctg aaagaacacc ccgtggaaaa cacccagctg cagaacgaga gctgtacct   3420
gtactacctg cagaatgggc gggatatgta cgtggaccag gaactgggaca tcaaccggct   3480
gtccgactac gatgtggacc atatcgtgcc tcagagcttt ctgaaggacg actccatcga   3540
caacaaggtg ctgaccagaa gcgacaagaa ccggggcaag agcgacaacg tgccctccga   3600
agaggtcgtg aagaagatga aaactactg gcggcagctg ctgaacgcca agctgattac   3660
ccagagaaag ttcgacaatc tgaccaaggc cgagagaggc ggcctgagcg aactggataa   3720
ggccggcttc atcaagagac agctggtgga aacccggcag atcacaaagc acgtggcaca   3780
gatcctggac tcccggatga acactaagta cgacgagaat gacaagctga tccgggaagt   3840
gaaagtgatc accctgaagt ccaagctggt gtccgatttc cggaaggatt tccagttta   3900
caaagtgcgc gagatcaaca actaccacca cgcccacgac gcctacctga acgccgtcgt   3960
gggaaccgcc ctgatcaaaa agtaccctaa gctggaaagc gagttcgtgt acggcgacta   4020
caaggtgtac gacgtgcgga gatgatcgc caagagcgag caggaaatcg gcaaggctac   4080
cgccaagtac ttcttctaca gcaacatcat gaactttttc aagaccgaga ttaccctggc   4140
caacggcgag atccggaagc ggcctctgat cgagacaaac ggcgaaaccg gggagatcgt   4200
gtgggataag ggccgggatt ttgccaccgt gcggaaagtg ctgagcatgc ccaagtgaa   4260
tatcgtgaaa aagaccgagg tgcagacagg cggcttcagc aaagagtcta tcctgcccaa   4320
gaggaacagc gataagctga tcgccagaaa aaaggactgg gaccctaaga agtacgcgg   4380
cttcgacagc cccaccgtgg cctattctgt gctggtggtg gccaaagtgg aaaagggcaa   4440
gtccaagaaa ctgaagagtg tgaaagagct gctgggatc accatcatgg aaagaagcag   4500
cttcgagaag aatcccatcg actttctgga agccaagggc tacaaagaag tgaaaaagga   4560
cctgatcatc aagctgccta agtactccct gttcgagctg gaaaacggcc ggaagagaat   4620
gctggcctct gccggcgaac tgcagaaggg aaacgaactg gccctgccct ccaaatatgt   4680
gaacttcctg tacctggcca gccactatga aagctgaag ggctcccccg aggataatga   4740
gcagaaacag ctgtttgtgg aacagcacaa gcactacctg gacgagatca tcgagcagat   4800
cagcgagttc tccaagagag tgatcctggc cgacgctaat ctggacaaag tgctgtccgc   4860
ctacaacaag caccgggata gcccatcag agagcaggcc gagaatatca tccacctgtt   4920
taccctgacc aatctgggag cccctgccgc cttcaagtac tttgacacca ccatcgaccg   4980
gaagaggtac accagcacca agaggtgct ggacgccacc ctgatccacc agagcatcac   5040
cggcctgtac gagacacgga tcgacctgtc tcagctggga ggcgacaaaa ggccggcggc   5100
cacgaaaaag gccggccagg caaaaaagaa aaagggcaca tctgagggca ggggaagtct   5160
gctaacatgc ggggacgtgg aggaaaatcc cggccccatg actgccctga ccgaaggtgc   5220
taagctgttt gagaaggaga ttccgtacat caccgagctg gaagggacg tcgaaggaat   5280
gaagttcatc atcaagggag aaggaaccgg ggacgctacg actggaacca ttaaggccaa   5340
gtatatctgt accactggag atctgccagt gccttgggcc acccttgtgt caaccctctc   5400
```

```
gtatggagtg cagtgttttg ctaagtaccc tagccacatt aaggacttct tcaaatccgc    5460
catgccggaa ggttataccc aagagcgcac catttctttt gagggagatg gagtgtacaa    5520
gacccgcgcg atggtcacct atgagagggg atctatctac aaccgggtga ctctgactgg    5580
agaaaacttt aagaaggacg ggcatattct tcggaagaat gtcgccttcc agtgccctcc    5640
cagcatcctt tacattctcc ccgacactgt gaacaacgga atccgcgtgg agttcaatca    5700
agcctacgac atcgaggggg tgacggagaa gctggtgacc aagtgtagcc agatgaatcg    5760
gccactggcc ggttcagcgg ctgtccacat tccgcgctac catcatatca cttatcacac    5820
taagctctcc aaagaccgcg atgagaggag agatcacatg tgcctggtgg aagtggtcaa    5880
ggccgtcgat ctcgatacct atcagtaagg tctcactcga gatcagcctc gactgtgcct    5940
tctagttgcc agccatctgt tgtttgcccc tcccccgtgc cttccttgac cctggaaggt    6000
gccactccca ctgtcctttc ctaataaaat gaggaaattg catcccact  tcagaagttc    6060 ctatactttc tagagaatag gaacttcact atagagtcga ataagggcga cacccccta a    6120 ttagcccggg cgaaaggccc agtctttcga ctgagccttt cgttttattt gatgcctggc    6180
agttccctac tctcgcatgg ggagtcccca cactaccatc ggcgctacgg cgtttcactt    6240
ctgagttcgg catggggtca ggtgggacca ccgcgctact gccgccaggc aaacaagggg    6300
tgttatgagc catattcagg tataaatggg ctcgcgataa tgttcagaat tggttaattg    6360
gttgtaacac tgaccctat  ttgtttattt ttctaaatac attcaaatat gtatccgctc    6420
atgagacaat aaccctgata aatgcttcaa taatattgaa aaaggaagaa tatgagccat    6480
attcaacggg aaacgtcgag gccgcgatta aattccaaca tggatgctga tttatatggg    6540
tataaatggg ctcgcgataa tgtcgggcaa tcaggtgcga caatctatcg cttgtatggg    6600
aagcccgatg cgccagagtt gtttctgaaa catggcaaag gtagcgttgc caatgatgtt    6660
acagatgaga tggtcagact aaactggctg acggaattta tgccacttcc gaccatcaag    6720
cattttatcc gtactcctga tgatgcatgg ttactcacca ctgcgatccc cggaaaaaca    6780
gcgttccagg tattagaaga atatcctgat tcaggtgaaa atattgttga tgcgctggca    6840
gtgttcctgc gccggttgca ctcgattcct gtttgtaatt gtcctttta  cagcgatcgc    6900 gtatttcgcc tcgctcaggc gcaatcacga atgaataacg gtttggttga tgcgagtgat    6960
tttgatgacg agcgtaatgg ctggcctgtt gaacaagtct ggaaagaaat gcataaactt    7020
ttgccattct caccggattc agtcgtcact catggtgatt tctcacttga taaccttatt    7080
tttgacgagg ggaaattaat aggttgtatt gatgttggac gagtcggaat cgcagaccga    7140
taccaggatc ttgccatcct atggaactgc ctcggtgagt tttctccttc attacagaaa    7200 cggcttttc  aaaaatatgg tattgataat cctgatatga ataaattgca gtttcatttg    7260
atgctcgatg agttttttcta aaagcagagc attacgctga cttgacggga cggcgcaagc    7320
tcatgaccaa aatcccttaa cgtgagttac gcgcgcgtcg ttccactgag cgtcagaccc    7380
cgtagaaaag atcaaaggat cttcttgaga tccttttttt ctgcgcgtaa tctgctgctt    7440
gcaaacaaaa aaaccaccgc taccagcggt ggtttgtttg ccggatcaag agctaccaac    7500 tcttttccg aaggtaactg gcttcagcag agcgcagata ccaaatactg ttcttctagt    7560
gtagccgtag ttagcccacc acttcaagaa ctctgtagca ccgcctacat acctcgctct    7620
gctaatcctg ttaccagtgg ctgctgccag tggcgataag tcgtgtctta ccgggttgga    7680
ctcaagacga tagttaccgg ataaggcgca gcggtcgggc tgaacggggg gttcgtgcac    7740
acagcccagc ttggagcgaa cgacctacac cgaactgaga tacctacagc gtgagctatg    7800
```

```
agaaagcgcc acgcttcccg aagggagaaa ggcggacagg tatccggtaa gcggcagggt    7860
cggaacagga gagcgcacga gggagcttcc aggggggaaac gcctggtatc tttatagtcc   7920
tgtcgggttt cgccacctct gacttgagcg tcgattttg tgatgctcgt caggggggcg    7980
gagcctatgg aaaaacgcca gcaacgcggc ctttttacgg ttcctggcct tttgctggcc   8040
ttttgctcac atgttctttc ctgcgttatc ccctgattct gtggataacc gtattaccgc   8100
ctttgagtga gctgataccg ctcgccgcag ccgaacgacc gagcgcagcg agtcagtgag   8160
cgaggaagcg gaaggcgaga gtagggaact gccaggcatc aaactaagca gaaggcccct   8220
gacggatggc cttttgcgt ttctacaaac tctttctgtg ttgtaaaacg acggccagtc    8280
ttaagctcgg gccccctggg cggttctgat aacgagtaat cgttaatccg caaataacgt   8340
aaaaacccgc ttcggcgggt ttttttatgg ggggagttta gggaaagagc atttgtcaga   8400
atatttaagg gcgcctgtca ctttgcttga tatatgagaa ttatttaacc ttataaatga   8460
gaaaaaagca acgcacttta ataagatac gttgctttt cgattgatga acacctataa    8520
ttaaactatt catctattat ttatgatttt ttgtatatac aatatttcta gtttgttaaa   8580
gagaattaag aaaataaatc tcgaaaataa taaagggaaa atcagttttt gatatcaaaa   8640
ttatacatgt caacgataat acaaaatata atacaaacta taagatgtta tcagtattta   8700
ttatgcattt agaataaatt ttgtgtcgcc cttattcgac tcactataga agttcctatt   8760
ctctagaaag tataggaact tcacttcatt ttccgtcttc gagggcctat ttcccatgat   8820
tccttcatat ttgcatatac gatcaaggc tgttagagag ataattggaa ttaatttgac    8880
tgtaaacaca aagatattag tacaaaatac gtgacgtaga aagtaataat ttcttgggta   8940
gtttgcagtt ttaaaattat gttttaaaat ggactatcat atgcttaccg taacttgaaa   9000
gtatttcgat ttcttggctt tatatatctt gtggaaagga cgaaacaccg tgaagagc     9058
```

<210> SEQ ID NO 11
<211> LENGTH: 263
<212> TYPE: PRT
<213> ORGANISM: Artificial sequence
<220> FEATURE:
<223> OTHER INFORMATION: Mammalian

<400> SEQUENCE: 11

```
Met Val Ser Lys Gly Glu Glu Leu Ile Lys Glu Asn Met Arg Met Lys
1               5                   10                  15

Leu Tyr Met Glu Gly Thr Val Asn Asn His His Phe Lys Cys Thr Ser
            20                  25                  30

Glu Gly Glu Gly Lys Pro Tyr Glu Gly Thr Gln Thr Met Arg Ile Lys
        35                  40                  45

Val Val Glu Gly Gly Pro Leu Pro Phe Ala Phe Asp Ile Leu Ala Thr
    50                  55                  60

Ser Phe Met Tyr Gly Ser Arg Thr Phe Ile Lys Tyr Pro Lys Gly Ile
65                  70                  75                  80

Pro Asp Phe Phe Lys Gln Ser Phe Pro Glu Gly Phe Thr Trp Glu Arg
                85                  90                  95

Val Thr Arg Tyr Glu Asp Gly Gly Val Val Thr Val Met Gln Asp Thr
            100                 105                 110

Ser Leu Glu Asp Gly Cys Leu Val Tyr His Val Gln Val Arg Gly Val
        115                 120                 125

Asn Phe Pro Ser Asn Gly Pro Val Met Gln Lys Lys Thr Lys Gly Trp
    130                 135                 140
```

```
Glu Pro Asn Thr Glu Met Leu Tyr Pro Ala Asp Gly Gly Leu Glu Gly
145                 150                 155                 160

Arg Ser Asp Met Ala Leu Lys Leu Val Gly Gly His Leu Ser Cys
                165                 170                 175

Ser Phe Val Thr Thr Tyr Arg Ser Lys Lys Pro Ala Lys Asn Leu Lys
                180                 185                 190

Met Pro Gly Ile His Ala Val Asp His Arg Leu Glu Arg Leu Glu Glu
            195                 200                 205

Ser Asp Asn Glu Met Phe Val Val Gln Arg Glu His Ala Val Ala Arg
        210                 215                 220

Tyr Cys Asp Leu Pro Ser Lys Leu Gly His Lys Leu Asn Ser Gly Leu
225                 230                 235                 240

Arg Ser Arg Ala Gln Ala Ser Asn Ser Ala Val Asp Gly Thr Ala Gly
                245                 250                 255

Pro Gly Ser Thr Gly Ser Arg
            260
```

```
<210> SEQ ID NO 12
<211> LENGTH: 383
<212> TYPE: DNA
<213> ORGANISM: Artificial sequence
<220> FEATURE:
<223> OTHER INFORMATION: Mammalian

<400> SEQUENCE: 12
gttttagagc tagaaatagc aagttaaaat aaggctagtc cgttatcaac ttgaaaaagt      60
ggcaccgagt cggtgctttt tgctccgcg gcacgagaac tcaaagcccc ggggcctggg     120
tcccacgcgg ggtcccttac ccagggtgcc ccgggcgctc atttgcatgt cccacccaac    180
aggtaaacct gacaggtcat cgcggccagg tacgacctgg cggtcagagc accaaacata    240
cgagccttgt gatgagttcc gttgcatgaa attctcccaa aggctccaag atggacagga    300
aagggcgcgg ttcggtcacc gtaagtagaa taggtgaaag actcccgtgc cttataaggc    360
ctgtgggtga cttcttctca ccg                                            383
```

```
<210> SEQ ID NO 13
<211> LENGTH: 53
<212> TYPE: DNA
<213> ORGANISM: Artificial sequence
<220> FEATURE:
<223> OTHER INFORMATION: Mammalian

<400> SEQUENCE: 13
gatgggatgg tctcagtttt agagctagaa atagcaagtt aaaataaggc tag            53
```

```
<210> SEQ ID NO 14
<211> LENGTH: 104
<212> TYPE: DNA
<213> ORGANISM: Artificial sequence
<220> FEATURE:
<223> OTHER INFORMATION: Mammalian

<400> SEQUENCE: 14
agggcaccgg tctctaaaca gcaatgaata tgaaaaactc ggtgaagagc gctcttctaa     60
cctgcctgaa tgcaaacact gcggtgagaa gaagtcaccc acag                     104
```

```
<210> SEQ ID NO 15
<211> LENGTH: 104
<212> TYPE: DNA
```

<213> ORGANISM: Artificial sequence
<220> FEATURE:
<223> OTHER INFORMATION: Mammalian

<400> SEQUENCE: 15

```
agggcaccgg tctctaaact cccataggcg ccctccccgc ggtgaagagc gctcttctaa    60
cgcagtacga atgcgtggcg gcggtgagaa gaagtcaccc acag                     104
```

<210> SEQ ID NO 16
<211> LENGTH: 104
<212> TYPE: DNA
<213> ORGANISM: Artificial sequence
<220> FEATURE:
<223> OTHER INFORMATION: Mammalian

<400> SEQUENCE: 16

```
agggcaccgg tctctaaacc atgtcgatgg acgtggagtc ggtgaagagc gctcttctaa    60
cccggatgtc ctctttgggg ccggtgagaa gaagtcaccc acag                     104
```

<210> SEQ ID NO 17
<211> LENGTH: 104
<212> TYPE: DNA
<213> ORGANISM: Artificial sequence
<220> FEATURE:
<223> OTHER INFORMATION: Mammalian

<400> SEQUENCE: 17

```
agggcaccgg tctctaaaca aaggcccaac gccatcctgc ggtgaagagc gctcttctaa    60
ctggcaaagc caaagtcagt gcggtgagaa gaagtcaccc acag                     104
```

<210> SEQ ID NO 18
<211> LENGTH: 104
<212> TYPE: DNA
<213> ORGANISM: Artificial sequence
<220> FEATURE:
<223> OTHER INFORMATION: Mammalian

<400> SEQUENCE: 18

```
agggcaccgg tctctaaacc caaaaactac gataaacatc ggtgaagagc gctcttctaa    60
ctcacttgat agtcctttgg acggtgagaa gaagtcaccc acag                     104
```

<210> SEQ ID NO 19
<211> LENGTH: 104
<212> TYPE: DNA
<213> ORGANISM: Artificial sequence
<220> FEATURE:
<223> OTHER INFORMATION: Mammalian

<400> SEQUENCE: 19

```
agggcaccgg tctctaaaca ccgagatgtc aaggtgaggc ggtgaagagc gctcttctaa    60
cgggccccca acctgaatcc tcggtgagaa gaagtcaccc acag                     104
```

<210> SEQ ID NO 20
<211> LENGTH: 104
<212> TYPE: DNA
<213> ORGANISM: Artificial sequence
<220> FEATURE:
<223> OTHER INFORMATION: Mammalian

<400> SEQUENCE: 20

```
agggcaccgg tctctaaacc gatcttgtgc gcgatgccgc ggtgaagagc gctcttctaa    60
caacccacga atcaagctca tcggtgagaa gaagtcaccc acag                     104
```

-continued

<210> SEQ ID NO 21
<211> LENGTH: 104
<212> TYPE: DNA
<213> ORGANISM: Artificial sequence
<220> FEATURE:
<223> OTHER INFORMATION: Mammalian

<400> SEQUENCE: 21
agggcaccgg tctctaaacg tgaattagcg ctttgggttc ggtgaagagc gctcttctaa    60
caaggagtgg cttatcttca ccggtgagaa gaagtcaccc acag                    104

<210> SEQ ID NO 22
<211> LENGTH: 104
<212> TYPE: DNA
<213> ORGANISM: Artificial sequence
<220> FEATURE:
<223> OTHER INFORMATION: Mammalian

<400> SEQUENCE: 22
agggcaccgg tctctaaacg ttgggcgtag aagacacttc ggtgaagagc gctcttctaa    60
cgcaagaagc tgtcctgttg acggtgagaa gaagtcaccc acag                    104

<210> SEQ ID NO 23
<211> LENGTH: 104
<212> TYPE: DNA
<213> ORGANISM: Artificial sequence
<220> FEATURE:
<223> OTHER INFORMATION: Mammalian

<400> SEQUENCE: 23
agggcaccgg tctctaaaca tctaacgaac tgatctggtc ggtgaagagc gctcttctaa    60
ctcctgcatg ccaggcttgt acggtgagaa gaagtcaccc acag                    104

<210> SEQ ID NO 24
<211> LENGTH: 104
<212> TYPE: DNA
<213> ORGANISM: Artificial sequence
<220> FEATURE:
<223> OTHER INFORMATION: Mammalian

<400> SEQUENCE: 24
agggcaccgg tctctaaaca cagggagacg tgtggatctc ggtgaagagc gctcttctaa    60
caggatgtgt ccatgagctc ccggtgagaa gaagtcaccc acag                    104

<210> SEQ ID NO 25
<211> LENGTH: 104
<212> TYPE: DNA
<213> ORGANISM: Artificial sequence
<220> FEATURE:
<223> OTHER INFORMATION: Mammalian

<400> SEQUENCE: 25
agggcaccgg tctctaaacc tccctcaag gaagagaatc ggtgaagagc gctcttctaa    60
cgggatgctg caaactatct tcggtgagaa gaagtcaccc acag                    104

<210> SEQ ID NO 26
<211> LENGTH: 104
<212> TYPE: DNA
<213> ORGANISM: Artificial sequence
<220> FEATURE:
<223> OTHER INFORMATION: Mammalian

<400> SEQUENCE: 26
agggcaccgg tctctaaacc agatttacac acggtctgtc ggtgaagagc gctcttctaa    60
cactggtgca ggaacagggt ccggtgagaa gaagtcaccc acag                    104

<210> SEQ ID NO 27
<211> LENGTH: 104
<212> TYPE: DNA
<213> ORGANISM: Artificial sequence
<220> FEATURE:
<223> OTHER INFORMATION: Mammalian

<400> SEQUENCE: 27
agggcaccgg tctctaaacg aaacaagttg acgggagagc ggtgaagagc gctcttctaa    60
cggcggattt tcttaagcgc ccggtgagaa gaagtcaccc acag                    104

<210> SEQ ID NO 28
<211> LENGTH: 104
<212> TYPE: DNA
<213> ORGANISM: Artificial sequence
<220> FEATURE:
<223> OTHER INFORMATION: Mammalian

<400> SEQUENCE: 28
agggcaccgg tctctaaacc ctcacgaact gtgctgatgc ggtgaagagc gctcttctaa    60
catggaggag gaggtggagg acggtgagaa gaagtcaccc acag                    104

<210> SEQ ID NO 29
<211> LENGTH: 104
<212> TYPE: DNA
<213> ORGANISM: Artificial sequence
<220> FEATURE:
<223> OTHER INFORMATION: Mammalian

<400> SEQUENCE: 29
agggcaccgg tctctaaact gggcaacaac agccatattc ggtgaagagc gctcttctaa    60
cggagcctgc cccggtgccg gcggtgagaa gaagtcaccc acag                    104

<210> SEQ ID NO 30
<211> LENGTH: 104
<212> TYPE: DNA
<213> ORGANISM: Artificial sequence
<220> FEATURE:
<223> OTHER INFORMATION: Mammalian

<400> SEQUENCE: 30
agggcaccgg tctctaaacc cacggtgagc cgcacccccc ggtgaagagc gctcttctaa    60
caccgcagga aggaaggaga gcggtgagaa gaagtcaccc acag                    104

<210> SEQ ID NO 31
<211> LENGTH: 104
<212> TYPE: DNA
<213> ORGANISM: Artificial sequence
<220> FEATURE:
<223> OTHER INFORMATION: Mammalian

<400> SEQUENCE: 31
agggcaccgg tctctaaacc aggctacgtg ggtaagtctc ggtgaagagc gctcttctaa    60
cactggtcaa ccttcctcct gcggtgagaa gaagtcaccc acag                    104

<210> SEQ ID NO 32
<211> LENGTH: 104

<212> TYPE: DNA
<213> ORGANISM: Artificial sequence
<220> FEATURE:
<223> OTHER INFORMATION: Mammalian

<400> SEQUENCE: 32
agggcaccgg tctctaaacg atagtggaga aggggttttc ggtgaagagc gctcttctaa    60
cagacttggc ggatcagagt gcggtgagaa gaagtcaccc acag                    104

<210> SEQ ID NO 33
<211> LENGTH: 104
<212> TYPE: DNA
<213> ORGANISM: Artificial sequence
<220> FEATURE:
<223> OTHER INFORMATION: Mammalian

<400> SEQUENCE: 33
agggcaccgg tctctaaacc aaagactcac agattttgtc ggtgaagagc gctcttctaa    60
cccagtgatt gctccacgcc ccggtgagaa gaagtcaccc acag                    104

<210> SEQ ID NO 34
<211> LENGTH: 104
<212> TYPE: DNA
<213> ORGANISM: Artificial sequence
<220> FEATURE:
<223> OTHER INFORMATION: Mammalian

<400> SEQUENCE: 34
agggcaccgg tctctaaact cttctatttc gtgagccagc ggtgaagagc gctcttctaa    60
ccacatcaag ctgattgact tcggtgagaa gaagtcaccc acag                    104

<210> SEQ ID NO 35
<211> LENGTH: 104
<212> TYPE: DNA
<213> ORGANISM: Artificial sequence
<220> FEATURE:
<223> OTHER INFORMATION: Mammalian

<400> SEQUENCE: 35
agggcaccgg tctctaaact aagccatggg tgattcagtc ggtgaagagc gctcttctaa    60
cgctgaaagg atcactgttt acggtgagaa gaagtcaccc acag                    104

<210> SEQ ID NO 36
<211> LENGTH: 104
<212> TYPE: DNA
<213> ORGANISM: Artificial sequence
<220> FEATURE:
<223> OTHER INFORMATION: Mammalian

<400> SEQUENCE: 36
agggcaccgg tctctaaacc cgtgggcgcc tgcggagtgc ggtgaagagc gctcttctaa    60
cgcacagaga gggcattctc gcggtgagaa gaagtcaccc acag                    104

<210> SEQ ID NO 37
<211> LENGTH: 104
<212> TYPE: DNA
<213> ORGANISM: Artificial sequence
<220> FEATURE:
<223> OTHER INFORMATION: Mammalian

<400> SEQUENCE: 37
agggcaccgg tctctaaacc aggaatctgg aattttattc ggtgaagagc gctcttctaa    60
cactgatcgg aaagaaacgt acggtgagaa gaagtcaccc acag                    104

<210> SEQ ID NO 38
<211> LENGTH: 104
<212> TYPE: DNA
<213> ORGANISM: Artificial sequence
<220> FEATURE:
<223> OTHER INFORMATION: Mammalian

<400> SEQUENCE: 38
agggcaccgg tctctaaacg cgcgcaagcc tcgcgcaggc ggtgaagagc gctcttctaa    60
caggcggagc cgctgcccct gcggtgagaa gaagtcaccc acag                   104

<210> SEQ ID NO 39
<211> LENGTH: 104
<212> TYPE: DNA
<213> ORGANISM: Artificial sequence
<220> FEATURE:
<223> OTHER INFORMATION: Mammalian

<400> SEQUENCE: 39
agggcaccgg tctctaaact ctggcctggt catggccagc ggtgaagagc gctcttctaa    60
cgttaatcaa ggcaaactca ccggtgagaa gaagtcaccc acag                   104

<210> SEQ ID NO 40
<211> LENGTH: 104
<212> TYPE: DNA
<213> ORGANISM: Artificial sequence
<220> FEATURE:
<223> OTHER INFORMATION: Mammalian

<400> SEQUENCE: 40
agggcaccgg tctctaaacc ggccgaggcg agatgctgtc ggtgaagagc gctcttctaa    60
ctggtcgacg gggaagaagg acggtgagaa gaagtcaccc acag                   104

<210> SEQ ID NO 41
<211> LENGTH: 104
<212> TYPE: DNA
<213> ORGANISM: Artificial sequence
<220> FEATURE:
<223> OTHER INFORMATION: Mammalian

<400> SEQUENCE: 41
agggcaccgg tctctaaaca gacaagagat gctggctgtc ggtgaagagc gctcttctaa    60
cggacttaac acttactgcc acggtgagaa gaagtcaccc acag                   104

<210> SEQ ID NO 42
<211> LENGTH: 104
<212> TYPE: DNA
<213> ORGANISM: Artificial sequence
<220> FEATURE:
<223> OTHER INFORMATION: Mammalian

<400> SEQUENCE: 42
agggcaccgg tctctaaacg aagggataca gtgtgaagtc ggtgaagagc gctcttctaa    60
ctcgtgatgc ccagactcca acggtgagaa gaagtcaccc acag                   104

<210> SEQ ID NO 43
<211> LENGTH: 104
<212> TYPE: DNA
<213> ORGANISM: Artificial sequence
<220> FEATURE:
<223> OTHER INFORMATION: Mammalian

<400> SEQUENCE: 43
agggcaccgg tctctaaact atttaggtca tactactagc ggtgaagagc gctcttctaa        60
cattcagaca taatttgctt ccggtgagaa gaagtcaccc acag        104

<210> SEQ ID NO 44
<211> LENGTH: 104
<212> TYPE: DNA
<213> ORGANISM: Artificial sequence
<220> FEATURE:
<223> OTHER INFORMATION: Mammalian

<400> SEQUENCE: 44
agggcaccgg tctctaaacg aagaccggcc acgtcattgc ggtgaagagc gctcttctaa        60
cgggtagccg ccaaggctca ccggtgagaa gaagtcaccc acag        104

<210> SEQ ID NO 45
<211> LENGTH: 104
<212> TYPE: DNA
<213> ORGANISM: Artificial sequence
<220> FEATURE:
<223> OTHER INFORMATION: Mammalian

<400> SEQUENCE: 45
agggcaccgg tctctaaact gatgcgcttt gctgggtttc ggtgaagagc gctcttctaa        60
cagaacttga tcaaccagat gcggtgagaa gaagtcaccc acag        104

<210> SEQ ID NO 46
<211> LENGTH: 104
<212> TYPE: DNA
<213> ORGANISM: Artificial sequence
<220> FEATURE:
<223> OTHER INFORMATION: Mammalian

<400> SEQUENCE: 46
agggcaccgg tctctaaacc tgctgccaga agcagtcttc ggtgaagagc gctcttctaa        60
cagcctccgt gactgaaccc ccggtgagaa gaagtcaccc acag        104

<210> SEQ ID NO 47
<211> LENGTH: 104
<212> TYPE: DNA
<213> ORGANISM: Artificial sequence
<220> FEATURE:
<223> OTHER INFORMATION: Mammalian

<400> SEQUENCE: 47
agggcaccgg tctctaaacg gcgacccccg ctcctacctc ggtgaagagc gctcttctaa        60
ctcgccaatc ttgatgaagt tcggtgagaa gaagtcaccc acag        104

<210> SEQ ID NO 48
<211> LENGTH: 104
<212> TYPE: DNA
<213> ORGANISM: Artificial sequence
<220> FEATURE:
<223> OTHER INFORMATION: Mammalian

<400> SEQUENCE: 48
agggcaccgg tctctaaacc gctaagttta tggttctttc ggtgaagagc gctcttctaa        60
caaacaatta attttctgac ccggtgagaa gaagtcaccc acag        104

<210> SEQ ID NO 49

```
<211> LENGTH: 104
<212> TYPE: DNA
<213> ORGANISM: Artificial sequence
<220> FEATURE:
<223> OTHER INFORMATION: Mammalian

<400> SEQUENCE: 49
agggcaccgg tctctaaacg catgctaact gggtgttgcc ggtgaagagc gctcttctaa      60
cattacaggt caacttacca acggtgagaa gaagtcaccc acag                     104

<210> SEQ ID NO 50
<211> LENGTH: 104
<212> TYPE: DNA
<213> ORGANISM: Artificial sequence
<220> FEATURE:
<223> OTHER INFORMATION: Mammalian

<400> SEQUENCE: 50
agggcaccgg tctctaaacc cgagttacta tttggagctc ggtgaagagc gctcttctaa      60
ccatgtccac acctacacca tcggtgagaa gaagtcaccc acag                     104

<210> SEQ ID NO 51
<211> LENGTH: 104
<212> TYPE: DNA
<213> ORGANISM: Artificial sequence
<220> FEATURE:
<223> OTHER INFORMATION: Mammalian

<400> SEQUENCE: 51
agggcaccgg tctctaaaca aacgcagtgc aatcaagatc ggtgaagagc gctcttctaa      60
cactgacaag aactgccaaa gcggtgagaa gaagtcaccc acag                     104

<210> SEQ ID NO 52
<211> LENGTH: 104
<212> TYPE: DNA
<213> ORGANISM: Artificial sequence
<220> FEATURE:
<223> OTHER INFORMATION: Mammalian

<400> SEQUENCE: 52
agggcaccgg tctctaaaca ccgtgtggtg acactctggc ggtgaagagc gctcttctaa      60
ccaccgagca acagctccgg gcggtgagaa gaagtcaccc acag                     104

<210> SEQ ID NO 53
<211> LENGTH: 104
<212> TYPE: DNA
<213> ORGANISM: Artificial sequence
<220> FEATURE:
<223> OTHER INFORMATION: Mammalian

<400> SEQUENCE: 53
agggcaccgg tctctaaact tgttactgtt gattccaacc ggtgaagagc gctcttctaa      60
cctgcaatca attctcggat gcggtgagaa gaagtcaccc acag                     104

<210> SEQ ID NO 54
<211> LENGTH: 104
<212> TYPE: DNA
<213> ORGANISM: Artificial sequence
<220> FEATURE:
<223> OTHER INFORMATION: Mammalian

<400> SEQUENCE: 54
agggcaccgg tctctaaaca cgatcacgtg gcttacaggc ggtgaagagc gctcttctaa      60
```
cttcccaatg accttgagga ccggtgagaa gaagtcaccc acag               104

<210> SEQ ID NO 55
<211> LENGTH: 104
<212> TYPE: DNA
<213> ORGANISM: Artificial sequence
<220> FEATURE:
<223> OTHER INFORMATION: Mammalian

<400> SEQUENCE: 55
agggcaccgg tctctaaaca gccggcaaaa gtactgcttc ggtgaagagc gctcttctaa   60
ctgctgttag atctgtggtg acggtgagaa gaagtcaccc acag                  104

<210> SEQ ID NO 56
<211> LENGTH: 104
<212> TYPE: DNA
<213> ORGANISM: Artificial sequence
<220> FEATURE:
<223> OTHER INFORMATION: Mammalian

<400> SEQUENCE: 56
agggcaccgg tctctaaacc ggacaaaggc ccgtcctggc ggtgaagagc gctcttctaa   60
cgcaacgggc acccagtgag ccggtgagaa gaagtcaccc acag                  104

<210> SEQ ID NO 57
<211> LENGTH: 104
<212> TYPE: DNA
<213> ORGANISM: Artificial sequence
<220> FEATURE:
<223> OTHER INFORMATION: Mammalian

<400> SEQUENCE: 57
agggcaccgg tctctaaacc aaagaagatg gaatttcctc ggtgaagagc gctcttctaa   60
cacagcactg ccacttgatt tcggtgagaa gaagtcaccc acag                  104

<210> SEQ ID NO 58
<211> LENGTH: 104
<212> TYPE: DNA
<213> ORGANISM: Artificial sequence
<220> FEATURE:
<223> OTHER INFORMATION: Mammalian

<400> SEQUENCE: 58
agggcaccgg tctctaaact cacgatgcag atgcagctgc ggtgaagagc gctcttctaa   60
cgaaagaaga cgctttcaga tcggtgagaa gaagtcaccc acag                  104

<210> SEQ ID NO 59
<211> LENGTH: 104
<212> TYPE: DNA
<213> ORGANISM: Artificial sequence
<220> FEATURE:
<223> OTHER INFORMATION: Mammalian

<400> SEQUENCE: 59
agggcaccgg tctctaaacg ataccacttc ccaagttctc ggtgaagagc gctcttctaa   60
ccaacagtac tttgtaagta tcggtgagaa gaagtcaccc acag                  104

<210> SEQ ID NO 60
<211> LENGTH: 104
<212> TYPE: DNA
<213> ORGANISM: Artificial sequence
<220> FEATURE:

<223> OTHER INFORMATION: Mammalian

<400> SEQUENCE: 60
agggcaccgg tctctaaacg aagtggatgt gtggagtctc ggtgaagagc gctcttctaa    60
cctgactaat gtatagagaa tcggtgagaa gaagtcaccc acag    104

<210> SEQ ID NO 61
<211> LENGTH: 104
<212> TYPE: DNA
<213> ORGANISM: Artificial sequence
<220> FEATURE:
<223> OTHER INFORMATION: Mammalian

<400> SEQUENCE: 61
agggcaccgg tctctaaaca gtaaccaagg gcagaccctc ggtgaagagc gctcttctaa    60
cacaacctag agaaggtaag acggtgagaa gaagtcaccc acag    104

<210> SEQ ID NO 62
<211> LENGTH: 104
<212> TYPE: DNA
<213> ORGANISM: Artificial sequence
<220> FEATURE:
<223> OTHER INFORMATION: Mammalian

<400> SEQUENCE: 62
agggcaccgg tctctaaacc ccccggaagc gtgtggattc ggtgaagagc gctcttctaa    60
ccttcccgtg acggctcagc acggtgagaa gaagtcaccc acag    104

<210> SEQ ID NO 63
<211> LENGTH: 104
<212> TYPE: DNA
<213> ORGANISM: Artificial sequence
<220> FEATURE:
<223> OTHER INFORMATION: Mammalian

<400> SEQUENCE: 63
agggcaccgg tctctaaacc gaggtgctgc agagcatccc ggtgaagagc gctcttctaa    60
cgatgtcata caccttgggc tcggtgagaa gaagtcaccc acag    104

<210> SEQ ID NO 64
<211> LENGTH: 104
<212> TYPE: DNA
<213> ORGANISM: Artificial sequence
<220> FEATURE:
<223> OTHER INFORMATION: Mammalian

<400> SEQUENCE: 64
agggcaccgg tctctaaacg gagaatatgc caacaccctc ggtgaagagc gctcttctaa    60
cctgccacgc acctgagcct ccggtgagaa gaagtcaccc acag    104

<210> SEQ ID NO 65
<211> LENGTH: 104
<212> TYPE: DNA
<213> ORGANISM: Artificial sequence
<220> FEATURE:
<223> OTHER INFORMATION: Mammalian

<400> SEQUENCE: 65
agggcaccgg tctctaaacc taagggtagt gcttttcagc ggtgaagagc gctcttctaa    60
ccgaggtcta ttaaatggta tcggtgagaa gaagtcaccc acag    104

<210> SEQ ID NO 66
<211> LENGTH: 104
<212> TYPE: DNA
<213> ORGANISM: Artificial sequence
<220> FEATURE:
<223> OTHER INFORMATION: Mammalian

<400> SEQUENCE: 66
agggcaccgg tctctaaacc gcaggtgagg agccagctgc ggtgaagagc gctcttctaa      60
ccaggagcac acgcaggtac gcggtgagaa gaagtcaccc acag                      104

<210> SEQ ID NO 67
<211> LENGTH: 104
<212> TYPE: DNA
<213> ORGANISM: Artificial sequence
<220> FEATURE:
<223> OTHER INFORMATION: Mammalian

<400> SEQUENCE: 67
agggcaccgg tctctaaaca atgccaagaa aagacatggc ggtgaagagc gctcttctaa      60
cccattattg ggaccaccaa tcggtgagaa gaagtcaccc acag                      104

<210> SEQ ID NO 68
<211> LENGTH: 104
<212> TYPE: DNA
<213> ORGANISM: Artificial sequence
<220> FEATURE:
<223> OTHER INFORMATION: Mammalian

<400> SEQUENCE: 68
agggcaccgg tctctaaact ccccggaagc gtgtggactc ggtgaagagc gctcttctaa      60
ccttgccgtg ccggttcagc acggtgagaa gaagtcaccc acag                      104

<210> SEQ ID NO 69
<211> LENGTH: 104
<212> TYPE: DNA
<213> ORGANISM: Artificial sequence
<220> FEATURE:
<223> OTHER INFORMATION: Mammalian

<400> SEQUENCE: 69
agggcaccgg tctctaaacc tctaaaaact cttaaccatc ggtgaagagc gctcttctaa      60
caaaggtgag tcattgtcac acggtgagaa gaagtcaccc acag                      104

<210> SEQ ID NO 70
<211> LENGTH: 104
<212> TYPE: DNA
<213> ORGANISM: Artificial sequence
<220> FEATURE:
<223> OTHER INFORMATION: Mammalian

<400> SEQUENCE: 70
agggcaccgg tctctaaact taagctttgg atattttttc ggtgaagagc gctcttctaa      60
ccaagttcaa caccccaaaa acggtgagaa gaagtcaccc acag                      104

<210> SEQ ID NO 71
<211> LENGTH: 104
<212> TYPE: DNA
<213> ORGANISM: Artificial sequence
<220> FEATURE:
<223> OTHER INFORMATION: Mammalian

<400> SEQUENCE: 71

```
agggcaccgg tctctaaaca tctgtgagcg tttcacagcc ggtgaagagc gctcttctaa      60
cgacagaggg aggcctgctt gcggtgagaa gaagtcaccc acag                      104
```

<210> SEQ ID NO 72
<211> LENGTH: 104
<212> TYPE: DNA
<213> ORGANISM: Artificial sequence
<220> FEATURE:
<223> OTHER INFORMATION: Mammalian

<400> SEQUENCE: 72

```
agggcaccgg tctctaaaca ttgttgctga gatgcttttc ggtgaagagc gctcttctaa      60
cagccctcaa gaacctcaaa tcggtgagaa gaagtcaccc acag                      104
```

<210> SEQ ID NO 73
<211> LENGTH: 104
<212> TYPE: DNA
<213> ORGANISM: Artificial sequence
<220> FEATURE:
<223> OTHER INFORMATION: Mammalian

<400> SEQUENCE: 73

```
agggcaccgg tctctaaacg ctgaccctgg gcattgcctc ggtgaagagc gctcttctaa      60
cgtgcacgat gctcttgctg tcggtgagaa gaagtcaccc acag                      104
```

<210> SEQ ID NO 74
<211> LENGTH: 104
<212> TYPE: DNA
<213> ORGANISM: Artificial sequence
<220> FEATURE:
<223> OTHER INFORMATION: Mammalian

<400> SEQUENCE: 74

```
agggcaccgg tctctaaacg gagctgagcc agaccttctc ggtgaagagc gctcttctaa      60
ccgggggcag cataggctgt acggtgagaa gaagtcaccc acag                      104
```

<210> SEQ ID NO 75
<211> LENGTH: 104
<212> TYPE: DNA
<213> ORGANISM: Artificial sequence
<220> FEATURE:
<223> OTHER INFORMATION: Mammalian

<400> SEQUENCE: 75

```
agggcaccgg tctctaaacg gagtatgcca aaccaaaatc ggtgaagagc gctcttctaa      60
cggtgaagag tcgaaaattt tcggtgagaa gaagtcaccc acag                      104
```

<210> SEQ ID NO 76
<211> LENGTH: 104
<212> TYPE: DNA
<213> ORGANISM: Artificial sequence
<220> FEATURE:
<223> OTHER INFORMATION: Mammalian

<400> SEQUENCE: 76

```
agggcaccgg tctctaaact caacatacgt atttctcttc ggtgaagagc gctcttctaa      60
caagatgatc ctgttgttaa gcggtgagaa gaagtcaccc acag                      104
```

<210> SEQ ID NO 77
<211> LENGTH: 104
<212> TYPE: DNA
<213> ORGANISM: Artificial sequence
<220> FEATURE:
<223> OTHER INFORMATION: Mammalian

<400> SEQUENCE: 77

```
agggcaccgg tctctaaact cagactttga gcatacgatc ggtgaagagc gctcttctaa    60
ccggtgactg catcaaaccc ccggtgagaa gaagtcaccc acag                    104
```

<210> SEQ ID NO 78
<211> LENGTH: 104
<212> TYPE: DNA
<213> ORGANISM: Artificial sequence
<220> FEATURE:
<223> OTHER INFORMATION: Mammalian

<400> SEQUENCE: 78

```
agggcaccgg tctctaaaca atgggctggc tgcaaaggcc ggtgaagagc gctcttctaa    60
cgaaactcgg cggggcccag gcggtgagaa gaagtcaccc acag                    104
```

<210> SEQ ID NO 79
<211> LENGTH: 104
<212> TYPE: DNA
<213> ORGANISM: Artificial sequence
<220> FEATURE:
<223> OTHER INFORMATION: Mammalian

<400> SEQUENCE: 79

```
agggcaccgg tctctaaact tgttgtccag tggtccgttc ggtgaagagc gctcttctaa    60
cgtgaagatg aacaagagca acggtgagaa gaagtcaccc acag                    104
```

<210> SEQ ID NO 80
<211> LENGTH: 104
<212> TYPE: DNA
<213> ORGANISM: Artificial sequence
<220> FEATURE:
<223> OTHER INFORMATION: Mammalian

<400> SEQUENCE: 80

```
agggcaccgg tctctaaacc taatcctgtt gttttagtc ggtgaagagc gctcttctaa     60
cggatggcga atactgccca gcggtgagaa gaagtcaccc acag                    104
```

<210> SEQ ID NO 81
<211> LENGTH: 104
<212> TYPE: DNA
<213> ORGANISM: Artificial sequence
<220> FEATURE:
<223> OTHER INFORMATION: Mammalian

<400> SEQUENCE: 81

```
agggcaccgg tctctaaaca gtactggaca gaatcaaatc ggtgaagagc gctcttctaa    60
ccataaggct ggagttaatg acggtgagaa gaagtcaccc acag                    104
```

<210> SEQ ID NO 82
<211> LENGTH: 104
<212> TYPE: DNA
<213> ORGANISM: Artificial sequence
<220> FEATURE:
<223> OTHER INFORMATION: Mammalian

<400> SEQUENCE: 82

```
agggcaccgg tctctaaacc gcatcacgat cacgggcgtc ggtgaagagc gctcttctaa    60
caggctgaac gtccaggtca ccggtgagaa gaagtcaccc acag                    104
```

<210> SEQ ID NO 83
<211> LENGTH: 104
<212> TYPE: DNA
<213> ORGANISM: Artificial sequence
<220> FEATURE:
<223> OTHER INFORMATION: Mammalian

<400> SEQUENCE: 83
agggcaccgg tctctaaacg ctctgccacg cccttagatc ggtgaagagc gctcttctaa    60
ctgcttcttt tgagggtgga ccggtgagaa gaagtcaccc acag                    104

<210> SEQ ID NO 84
<211> LENGTH: 104
<212> TYPE: DNA
<213> ORGANISM: Artificial sequence
<220> FEATURE:
<223> OTHER INFORMATION: Mammalian

<400> SEQUENCE: 84
agggcaccgg tctctaaacc ggcagggaca ccaggctctc ggtgaagagc gctcttctaa    60
cgaaatgccc acactggaat ccggtgagaa gaagtcaccc acag                    104

<210> SEQ ID NO 85
<211> LENGTH: 104
<212> TYPE: DNA
<213> ORGANISM: Artificial sequence
<220> FEATURE:
<223> OTHER INFORMATION: Mammalian

<400> SEQUENCE: 85
agggcaccgg tctctaaaca ccgcctgaca tccaggaagc ggtgaagagc gctcttctaa    60
ccaaagatct ggttgaggac gcggtgagaa gaagtcaccc acag                    104

<210> SEQ ID NO 86
<211> LENGTH: 104
<212> TYPE: DNA
<213> ORGANISM: Artificial sequence
<220> FEATURE:
<223> OTHER INFORMATION: Mammalian

<400> SEQUENCE: 86
agggcaccgg tctctaaacg acgtcaatgg gggagctgtc ggtgaagagc gctcttctaa    60
cgaagtactc ctgaggtcta ccggtgagaa gaagtcaccc acag                    104

<210> SEQ ID NO 87
<211> LENGTH: 104
<212> TYPE: DNA
<213> ORGANISM: Artificial sequence
<220> FEATURE:
<223> OTHER INFORMATION: Mammalian

<400> SEQUENCE: 87
agggcaccgg tctctaaacg gaggggcggg aggtgtgtgc ggtgaagagc gctcttctaa    60
cgacgcagca cacgcagctc ccggtgagaa gaagtcaccc acag                    104

<210> SEQ ID NO 88
<211> LENGTH: 104
<212> TYPE: DNA
<213> ORGANISM: Artificial sequence
<220> FEATURE:
<223> OTHER INFORMATION: Mammalian

<400> SEQUENCE: 88

```
agggcaccgg tctctaaacg cgagggaagt ttcctgcctc ggtgaagagc gctcttctaa    60
cctcgcgggg cacgccgctc acggtgagaa gaagtcaccc acag                     104
```

<210> SEQ ID NO 89
<211> LENGTH: 104
<212> TYPE: DNA
<213> ORGANISM: Artificial sequence
<220> FEATURE:
<223> OTHER INFORMATION: Mammalian

<400> SEQUENCE: 89

```
agggcaccgg tctctaaacg ctcatcaatg agttgggtgc ggtgaagagc gctcttctaa    60
cggccgaagt cagccagctt gcggtgagaa gaagtcaccc acag                     104
```

<210> SEQ ID NO 90
<211> LENGTH: 104
<212> TYPE: DNA
<213> ORGANISM: Artificial sequence
<220> FEATURE:
<223> OTHER INFORMATION: Mammalian

<400> SEQUENCE: 90

```
agggcaccgg tctctaaacg actctgttgc tttggaggtc ggtgaagagc gctcttctaa    60
cattcagccg ccacagaacc tcggtgagaa gaagtcaccc acag                     104
```

<210> SEQ ID NO 91
<211> LENGTH: 104
<212> TYPE: DNA
<213> ORGANISM: Artificial sequence
<220> FEATURE:
<223> OTHER INFORMATION: Mammalian

<400> SEQUENCE: 91

```
agggcaccgg tctctaaact tttagaatta tatttgactc ggtgaagagc gctcttctaa    60
cgaaaatatt ttgtttgtga acggtgagaa gaagtcaccc acag                     104
```

<210> SEQ ID NO 92
<211> LENGTH: 104
<212> TYPE: DNA
<213> ORGANISM: Artificial sequence
<220> FEATURE:
<223> OTHER INFORMATION: Mammalian

<400> SEQUENCE: 92

```
agggcaccgg tctctaaacc tcacaaacac gtcgcctgcc ggtgaagagc gctcttctaa    60
cagtgaatct ggggagctct tcggtgagaa gaagtcaccc acag                     104
```

<210> SEQ ID NO 93
<211> LENGTH: 104
<212> TYPE: DNA
<213> ORGANISM: Artificial sequence
<220> FEATURE:
<223> OTHER INFORMATION: Mammalian

<400> SEQUENCE: 93

```
agggcaccgg tctctaaact actccagcaa acacaggatc ggtgaagagc gctcttctaa    60
caggcatcag gagcttttta acggtgagaa gaagtcaccc acag                     104
```

<210> SEQ ID NO 94
<211> LENGTH: 104
<212> TYPE: DNA

```
<213> ORGANISM: Artificial sequence
<220> FEATURE:
<223> OTHER INFORMATION: Mammalian

<400> SEQUENCE: 94
agggcaccgg tctctaaact tgagctcctg gggtcagctc ggtgaagagc gctcttctaa      60
cgagaaaatg agttaagaag acggtgagaa gaagtcaccc acag                     104

<210> SEQ ID NO 95
<211> LENGTH: 104
<212> TYPE: DNA
<213> ORGANISM: Artificial sequence
<220> FEATURE:
<223> OTHER INFORMATION: Mammalian

<400> SEQUENCE: 95
agggcaccgg tctctaaacc gcatgcagtg cagcagcttc ggtgaagagc gctcttctaa      60
ccaaccgcat catcaagaac gcggtgagaa gaagtcaccc acag                     104

<210> SEQ ID NO 96
<211> LENGTH: 104
<212> TYPE: DNA
<213> ORGANISM: Artificial sequence
<220> FEATURE:
<223> OTHER INFORMATION: Mammalian

<400> SEQUENCE: 96
agggcaccgg tctctaaacc gagagtgcct acctctgttc ggtgaagagc gctcttctaa      60
cggccctgca gcaccctac tcggtgagaa gaagtcaccc acag                      104

<210> SEQ ID NO 97
<211> LENGTH: 104
<212> TYPE: DNA
<213> ORGANISM: Artificial sequence
<220> FEATURE:
<223> OTHER INFORMATION: Mammalian

<400> SEQUENCE: 97
agggcaccgg tctctaaacg agtgggatga ccgttccagc ggtgaagagc gctcttctaa      60
cccgctcacc aggtctttga ccggtgagaa gaagtcaccc acag                     104

<210> SEQ ID NO 98
<211> LENGTH: 104
<212> TYPE: DNA
<213> ORGANISM: Artificial sequence
<220> FEATURE:
<223> OTHER INFORMATION: Mammalian

<400> SEQUENCE: 98
agggcaccgg tctctaaacg ccagcagcgt gtacatgatc ggtgaagagc gctcttctaa      60
ccgcatgtcc aggtggagca ccggtgagaa gaagtcaccc acag                     104

<210> SEQ ID NO 99
<211> LENGTH: 104
<212> TYPE: DNA
<213> ORGANISM: Artificial sequence
<220> FEATURE:
<223> OTHER INFORMATION: Mammalian

<400> SEQUENCE: 99
agggcaccgg tctctaaacg gagttgccac cactgttgtc ggtgaagagc gctcttctaa      60
cttaggagac aaggacggca gcggtgagaa gaagtcaccc acag                     104
```

<210> SEQ ID NO 100
<211> LENGTH: 104
<212> TYPE: DNA
<213> ORGANISM: Artificial sequence
<220> FEATURE:
<223> OTHER INFORMATION: Mammalian

<400> SEQUENCE: 100
agggcaccgg tctctaaaca caggtccaca ggcttcccgc ggtgaagagc gctcttctaa      60
cagaagtgct gcggaaggac ccggtgagaa gaagtcaccc acag                     104

<210> SEQ ID NO 101
<211> LENGTH: 104
<212> TYPE: DNA
<213> ORGANISM: Artificial sequence
<220> FEATURE:
<223> OTHER INFORMATION: Mammalian

<400> SEQUENCE: 101
agggcaccgg tctctaaaca gcgtgtgcag aggtggtgtc ggtgaagagc gctcttctaa      60
cacccgaagc tgcgtgttgc ccggtgagaa gaagtcaccc acag                     104

<210> SEQ ID NO 102
<211> LENGTH: 104
<212> TYPE: DNA
<213> ORGANISM: Artificial sequence
<220> FEATURE:
<223> OTHER INFORMATION: Mammalian

<400> SEQUENCE: 102
agggcaccgg tctctaaaca gaacttgctt gtgccacctc ggtgaagagc gctcttctaa      60
ccttgtggat cgttttattc acggtgagaa gaagtcaccc acag                     104

<210> SEQ ID NO 103
<211> LENGTH: 104
<212> TYPE: DNA
<213> ORGANISM: Artificial sequence
<220> FEATURE:
<223> OTHER INFORMATION: Mammalian

<400> SEQUENCE: 103
agggcaccgg tctctaaact cccgaagacc ggtgactttc ggtgaagagc gctcttctaa      60
ctgagtcatg tcctgaaact acggtgagaa gaagtcaccc acag                     104

<210> SEQ ID NO 104
<211> LENGTH: 104
<212> TYPE: DNA
<213> ORGANISM: Artificial sequence
<220> FEATURE:
<223> OTHER INFORMATION: Mammalian

<400> SEQUENCE: 104
agggcaccgg tctctaaaca acgcggcccc ctcgcccctc ggtgaagagc gctcttctaa      60
ctgggcactc gagtgccatt acggtgagaa gaagtcaccc acag                     104

<210> SEQ ID NO 105
<211> LENGTH: 104
<212> TYPE: DNA
<213> ORGANISM: Artificial sequence
<220> FEATURE:
<223> OTHER INFORMATION: Mammalian

```
<400> SEQUENCE: 105
agggcaccgg tctctaaaca tggccccgac agatgccttc ggtgaagagc gctcttctaa      60
cccggcccag gcggcaccgg ccggtgagaa gaagtcaccc acag                      104

<210> SEQ ID NO 106
<211> LENGTH: 104
<212> TYPE: DNA
<213> ORGANISM: Artificial sequence
<220> FEATURE:
<223> OTHER INFORMATION: Mammalian

<400> SEQUENCE: 106
agggcaccgg tctctaaacg accctcccaa gaccctcatc ggtgaagagc gctcttctaa      60
ccacagatcg actccaggta tcggtgagaa gaagtcaccc acag                      104

<210> SEQ ID NO 107
<211> LENGTH: 104
<212> TYPE: DNA
<213> ORGANISM: Artificial sequence
<220> FEATURE:
<223> OTHER INFORMATION: Mammalian

<400> SEQUENCE: 107
agggcaccgg tctctaaacg tcagtaagag aaggccaagc ggtgaagagc gctcttctaa      60
ctgcacgcgg atgctcatga tcggtgagaa gaagtcaccc acag                      104

<210> SEQ ID NO 108
<211> LENGTH: 104
<212> TYPE: DNA
<213> ORGANISM: Artificial sequence
<220> FEATURE:
<223> OTHER INFORMATION: Mammalian

<400> SEQUENCE: 108
agggcaccgg tctctaaacc atcgccgacg ggctcccggc ggtgaagagc gctcttctaa      60
cgggcccgcc cggcggtccg acggtgagaa gaagtcaccc acag                      104

<210> SEQ ID NO 109
<211> LENGTH: 104
<212> TYPE: DNA
<213> ORGANISM: Artificial sequence
<220> FEATURE:
<223> OTHER INFORMATION: Mammalian

<400> SEQUENCE: 109
agggcaccgg tctctaaaca aggatatgcg aagaaagatc ggtgaagagc gctcttctaa      60
cctgggaact caaaactgcc tcggtgagaa gaagtcaccc acag                      104

<210> SEQ ID NO 110
<211> LENGTH: 104
<212> TYPE: DNA
<213> ORGANISM: Artificial sequence
<220> FEATURE:
<223> OTHER INFORMATION: Mammalian

<400> SEQUENCE: 110
agggcaccgg tctctaaacg cacgcgcttc aacgccacgc ggtgaagagc gctcttctaa      60
cgcgacttga agaacggagg ccggtgagaa gaagtcaccc acag                      104

<210> SEQ ID NO 111
<211> LENGTH: 104
```

```
<212> TYPE: DNA
<213> ORGANISM: Artificial sequence
<220> FEATURE:
<223> OTHER INFORMATION: Mammalian

<400> SEQUENCE: 111
agggcaccgg tctctaaacg cacatcacct gcaaagatgc ggtgaagagc gctcttctaa    60
ccgtccatcg acatgtggtc acggtgagaa gaagtcaccc acag                    104

<210> SEQ ID NO 112
<211> LENGTH: 104
<212> TYPE: DNA
<213> ORGANISM: Artificial sequence
<220> FEATURE:
<223> OTHER INFORMATION: Mammalian

<400> SEQUENCE: 112
agggcaccgg tctctaaacg cacatcgtac ggatcgtggc ggtgaagagc gctcttctaa    60
cccctgcgta cagattctcg tcggtgagaa gaagtcaccc acag                    104

<210> SEQ ID NO 113
<211> LENGTH: 104
<212> TYPE: DNA
<213> ORGANISM: Artificial sequence
<220> FEATURE:
<223> OTHER INFORMATION: Mammalian

<400> SEQUENCE: 113
agggcaccgg tctctaaaca tccaaaggac tatcaagtgc ggtgaagagc gctcttctaa    60
cgaaaattct ggctcaggaa gcggtgagaa gaagtcaccc acag                    104

<210> SEQ ID NO 114
<211> LENGTH: 104
<212> TYPE: DNA
<213> ORGANISM: Artificial sequence
<220> FEATURE:
<223> OTHER INFORMATION: Mammalian

<400> SEQUENCE: 114
agggcaccgg tctctaaaca ccgagatgtc aaggtgaggc ggtgaagagc gctcttctaa    60
ccgggccccc aacctgaatc ccggtgagaa gaagtcaccc acag                    104

<210> SEQ ID NO 115
<211> LENGTH: 104
<212> TYPE: DNA
<213> ORGANISM: Artificial sequence
<220> FEATURE:
<223> OTHER INFORMATION: Mammalian

<400> SEQUENCE: 115
agggcaccgg tctctaaacc gatcttgtgc gcgatgccgc ggtgaagagc gctcttctaa    60
cacccacgaa tcaagctcat ccggtgagaa gaagtcaccc acag                    104

<210> SEQ ID NO 116
<211> LENGTH: 104
<212> TYPE: DNA
<213> ORGANISM: Artificial sequence
<220> FEATURE:
<223> OTHER INFORMATION: Mammalian

<400> SEQUENCE: 116
agggcaccgg tctctaaacg catcaagtga gtcattattc ggtgaagagc gctcttctaa    60
```
cagcgccctt caatggagga acggtgagaa gaagtcaccc acag        104

<210> SEQ ID NO 117
<211> LENGTH: 104
<212> TYPE: DNA
<213> ORGANISM: Artificial sequence
<220> FEATURE:
<223> OTHER INFORMATION: Mammalian

<400> SEQUENCE: 117
agggcaccgg tctctaaacg ttgtagacac catcctagtc ggtgaagagc gctcttctaa        60
ctacctattg gcatctgcac acggtgagaa gaagtcaccc acag        104

<210> SEQ ID NO 118
<211> LENGTH: 104
<212> TYPE: DNA
<213> ORGANISM: Artificial sequence
<220> FEATURE:
<223> OTHER INFORMATION: Mammalian

<400> SEQUENCE: 118
agggcaccgg tctctaaacg tatctgtgcc catgcctatc ggtgaagagc gctcttctaa        60
cagaagtctg gcgtgcaggt ccggtgagaa gaagtcaccc acag        104

<210> SEQ ID NO 119
<211> LENGTH: 104
<212> TYPE: DNA
<213> ORGANISM: Artificial sequence
<220> FEATURE:
<223> OTHER INFORMATION: Mammalian

<400> SEQUENCE: 119
agggcaccgg tctctaaacg gccaccgtga actcacaggc ggtgaagagc gctcttctaa        60
cggtccatga gcagccgctt ccggtgagaa gaagtcaccc acag        104

<210> SEQ ID NO 120
<211> LENGTH: 104
<212> TYPE: DNA
<213> ORGANISM: Artificial sequence
<220> FEATURE:
<223> OTHER INFORMATION: Mammalian

<400> SEQUENCE: 120
agggcaccgg tctctaaact cccctcaagg aagagaatgc ggtgaagagc gctcttctaa        60
cgggatgctg caaactatct tcggtgagaa gaagtcaccc acag        104

<210> SEQ ID NO 121
<211> LENGTH: 104
<212> TYPE: DNA
<213> ORGANISM: Artificial sequence
<220> FEATURE:
<223> OTHER INFORMATION: Mammalian

<400> SEQUENCE: 121
agggcaccgg tctctaaact tattgccccg cgaccggatc ggtgaagagc gctcttctaa        60
catggagact cactgatttc gcggtgagaa gaagtcaccc acag        104

<210> SEQ ID NO 122
<211> LENGTH: 104
<212> TYPE: DNA
<213> ORGANISM: Artificial sequence
<220> FEATURE:
<223> OTHER INFORMATION: Mammalian -continued

<400> SEQUENCE: 122
agggcaccgg tctctaaacc atcaaggtaa tgcttctcac ggtgaagagc gctcttctaa    60
cagacatgcc catgatgaga gcggtgagaa gaagtcaccc acag                     104

<210> SEQ ID NO 123
<211> LENGTH: 104
<212> TYPE: DNA
<213> ORGANISM: Artificial sequence
<220> FEATURE:
<223> OTHER INFORMATION: Mammalian

<400> SEQUENCE: 123
agggcaccgg tctctaaact tactccccac gcccaacccc ggtgaagagc gctcttctaa    60
caatgttgtc cggtgagaag gcggtgagaa gaagtcaccc acag                     104

<210> SEQ ID NO 124
<211> LENGTH: 104
<212> TYPE: DNA
<213> ORGANISM: Artificial sequence
<220> FEATURE:
<223> OTHER INFORMATION: Mammalian

<400> SEQUENCE: 124
agggcaccgg tctctaaacc acctgcacca ccaccaccac ggtgaagagc gctcttctaa    60
caccccggat gaagatggtg tcggtgagaa gaagtcaccc acag                     104

<210> SEQ ID NO 125
<211> LENGTH: 104
<212> TYPE: DNA
<213> ORGANISM: Artificial sequence
<220> FEATURE:
<223> OTHER INFORMATION: Mammalian

<400> SEQUENCE: 125
agggcaccgg tctctaaacc cacggtgagc cgcacccccc ggtgaagagc gctcttctaa    60
ccaccgcagg aaggaaggag acggtgagaa gaagtcaccc acag                     104

<210> SEQ ID NO 126
<211> LENGTH: 104
<212> TYPE: DNA
<213> ORGANISM: Artificial sequence
<220> FEATURE:
<223> OTHER INFORMATION: Mammalian

<400> SEQUENCE: 126
agggcaccgg tctctaaact tagccaagga ctttatttgc ggtgaagagc gctcttctaa    60
cctcgttcgg atccttctca acggtgagaa gaagtcaccc acag                     104

<210> SEQ ID NO 127
<211> LENGTH: 104
<212> TYPE: DNA
<213> ORGANISM: Artificial sequence
<220> FEATURE:
<223> OTHER INFORMATION: Mammalian

<400> SEQUENCE: 127
agggcaccgg tctctaaact cacaattcaa cagatccttc ggtgaagagc gctcttctaa    60
cgacaccctg gcaaaaaaga acggtgagaa gaagtcaccc acag                     104

<210> SEQ ID NO 128

```
<211> LENGTH: 104
<212> TYPE: DNA
<213> ORGANISM: Artificial sequence
<220> FEATURE:
<223> OTHER INFORMATION: Mammalian

<400> SEQUENCE: 128
agggcaccgg tctctaaacc aaagactcac agattttgtc ggtgaagagc gctcttctaa      60
cgtgattgct ccacgcccag acggtgagaa gaagtcaccc acag                      104

<210> SEQ ID NO 129
<211> LENGTH: 104
<212> TYPE: DNA
<213> ORGANISM: Artificial sequence
<220> FEATURE:
<223> OTHER INFORMATION: Mammalian

<400> SEQUENCE: 129
agggcaccgg tctctaaacg atctaagctg agccagagcc ggtgaagagc gctcttctaa      60
cacatcctgt gagtatccct gcggtgagaa gaagtcaccc acag                      104

<210> SEQ ID NO 130
<211> LENGTH: 104
<212> TYPE: DNA
<213> ORGANISM: Artificial sequence
<220> FEATURE:
<223> OTHER INFORMATION: Mammalian

<400> SEQUENCE: 130
agggcaccgg tctctaaacc tgagcaggat aaaaaggatc ggtgaagagc gctcttctaa      60
cgtagacgtc tgggggtgcg gcggtgagaa gaagtcaccc acag                      104

<210> SEQ ID NO 131
<211> LENGTH: 104
<212> TYPE: DNA
<213> ORGANISM: Artificial sequence
<220> FEATURE:
<223> OTHER INFORMATION: Mammalian

<400> SEQUENCE: 131
agggcaccgg tctctaaact gggcgcctgc ggagtgcggc ggtgaagagc gctcttctaa      60
cgcacagaga gggcattctc gcggtgagaa gaagtcaccc acag                      104

<210> SEQ ID NO 132
<211> LENGTH: 104
<212> TYPE: DNA
<213> ORGANISM: Artificial sequence
<220> FEATURE:
<223> OTHER INFORMATION: Mammalian

<400> SEQUENCE: 132
agggcaccgg tctctaaacc aaaatggacg ttaccaaatc ggtgaagagc gctcttctaa      60
cggggatcag gagaacatcg gcggtgagaa gaagtcaccc acag                      104

<210> SEQ ID NO 133
<211> LENGTH: 104
<212> TYPE: DNA
<213> ORGANISM: Artificial sequence
<220> FEATURE:
<223> OTHER INFORMATION: Mammalian

<400> SEQUENCE: 133
agggcaccgg tctctaaacc cccggaccgg ggacacggcc ggtgaagagc gctcttctaa      60
```

```
ccgcctgagc gcccccgcat gcggtgagaa gaagtcaccc acag            104
```

<210> SEQ ID NO 134
<211> LENGTH: 104
<212> TYPE: DNA
<213> ORGANISM: Artificial sequence
<220> FEATURE:
<223> OTHER INFORMATION: Mammalian

<400> SEQUENCE: 134

```
agggcaccgg tctctaaacg aaaggtgagt ttgccttgac ggtgaagagc gctcttctaa    60
cgagaaataa tccaattacc tcggtgagaa gaagtcaccc acag                    104
```

<210> SEQ ID NO 135
<211> LENGTH: 104
<212> TYPE: DNA
<213> ORGANISM: Artificial sequence
<220> FEATURE:
<223> OTHER INFORMATION: Mammalian

<400> SEQUENCE: 135

```
agggcaccgg tctctaaacc gtcgaccacg ggccggccac ggtgaagagc gctcttctaa    60
cgacgccaaa gagctggagg ccggtgagaa gaagtcaccc acag                    104
```

<210> SEQ ID NO 136
<211> LENGTH: 104
<212> TYPE: DNA
<213> ORGANISM: Artificial sequence
<220> FEATURE:
<223> OTHER INFORMATION: Mammalian

<400> SEQUENCE: 136

```
agggcaccgg tctctaaact ccaatattct tctggacagc ggtgaagagc gctcttctaa    60
caagtcacag agcttaatat tcggtgagaa gaagtcaccc acag                    104
```

<210> SEQ ID NO 137
<211> LENGTH: 104
<212> TYPE: DNA
<213> ORGANISM: Artificial sequence
<220> FEATURE:
<223> OTHER INFORMATION: Mammalian

<400> SEQUENCE: 137

```
agggcaccgg tctctaaaca gagctcaacc agaagggatc ggtgaagagc gctcttctaa    60
cagactccaa atgtcagact tcggtgagaa gaagtcaccc acag                    104
```

<210> SEQ ID NO 138
<211> LENGTH: 104
<212> TYPE: DNA
<213> ORGANISM: Artificial sequence
<220> FEATURE:
<223> OTHER INFORMATION: Mammalian

<400> SEQUENCE: 138

```
agggcaccgg tctctaaact ataaggtaat tttttcatac ggtgaagagc gctcttctaa    60
ccaagtcaat accataggca tcggtgagaa gaagtcaccc acag                    104
```

<210> SEQ ID NO 139
<211> LENGTH: 104
<212> TYPE: DNA
<213> ORGANISM: Artificial sequence
<220> FEATURE:

<223> OTHER INFORMATION: Mammalian

<400> SEQUENCE: 139
agggcaccgg tctctaaacg gcggtgcgcg gcggcggtgc ggtgaagagc gctcttctaa    60
cgggaggacg ccgccatctt ccggtgagaa gaagtcaccc acag    104

<210> SEQ ID NO 140
<211> LENGTH: 104
<212> TYPE: DNA
<213> ORGANISM: Artificial sequence
<220> FEATURE:
<223> OTHER INFORMATION: Mammalian

<400> SEQUENCE: 140
agggcaccgg tctctaaacc gggtgcttga gagcctggtc ggtgaagagc gctcttctaa    60
ctaaacccag caaagcgcat ccggtgagaa gaagtcaccc acag    104

<210> SEQ ID NO 141
<211> LENGTH: 104
<212> TYPE: DNA
<213> ORGANISM: Artificial sequence
<220> FEATURE:
<223> OTHER INFORMATION: Mammalian

<400> SEQUENCE: 141
agggcaccgg tctctaaacc atatggtgac catgtcagtc ggtgaagagc gctcttctaa    60
cctggaaagc agggcttaaa tcggtgagaa gaagtcaccc acag    104

<210> SEQ ID NO 142
<211> LENGTH: 104
<212> TYPE: DNA
<213> ORGANISM: Artificial sequence
<220> FEATURE:
<223> OTHER INFORMATION: Mammalian

<400> SEQUENCE: 142
agggcaccgg tctctaaacg caggatgaac gaggagcagc ggtgaagagc gctcttctaa    60
cgcagcactg caaggcacac gcggtgagaa gaagtcaccc acag    104

<210> SEQ ID NO 143
<211> LENGTH: 104
<212> TYPE: DNA
<213> ORGANISM: Artificial sequence
<220> FEATURE:
<223> OTHER INFORMATION: Mammalian

<400> SEQUENCE: 143
agggcaccgg tctctaaaca agaaacggct gactacattc ggtgaagagc gctcttctaa    60
cgtgacccac ggatgctgga gcggtgagaa gaagtcaccc acag    104

<210> SEQ ID NO 144
<211> LENGTH: 104
<212> TYPE: DNA
<213> ORGANISM: Artificial sequence
<220> FEATURE:
<223> OTHER INFORMATION: Mammalian

<400> SEQUENCE: 144
agggcaccgg tctctaaaca gatggtattc actacctgcc ggtgaagagc gctcttctaa    60
caatctctgt gcaacaccca gcggtgagaa gaagtcaccc acag    104

```
<210> SEQ ID NO 145
<211> LENGTH: 104
<212> TYPE: DNA
<213> ORGANISM: Artificial sequence
<220> FEATURE:
<223> OTHER INFORMATION: Mammalian

<400> SEQUENCE: 145
agggcaccgg tctctaaacc cgagttacta tttggagctc ggtgaagagc gctcttctaa    60
cacatgtcca cacctacacc acggtgagaa gaagtcaccc acag                    104

<210> SEQ ID NO 146
<211> LENGTH: 104
<212> TYPE: DNA
<213> ORGANISM: Artificial sequence
<220> FEATURE:
<223> OTHER INFORMATION: Mammalian

<400> SEQUENCE: 146
agggcaccgg tctctaaaca aacgcagtgc aatcaagatc ggtgaagagc gctcttctaa    60
ccaactgaca agaactgcca acggtgagaa gaagtcaccc acag                    104

<210> SEQ ID NO 147
<211> LENGTH: 104
<212> TYPE: DNA
<213> ORGANISM: Artificial sequence
<220> FEATURE:
<223> OTHER INFORMATION: Mammalian

<400> SEQUENCE: 147
agggcaccgg tctctaaaca atacgagaag ctcgccaagc ggtgaagagc gctcttctaa    60
cgccttaccc gaaggtgcct tcggtgagaa gaagtcaccc acag                    104

<210> SEQ ID NO 148
<211> LENGTH: 104
<212> TYPE: DNA
<213> ORGANISM: Artificial sequence
<220> FEATURE:
<223> OTHER INFORMATION: Mammalian

<400> SEQUENCE: 148
agggcaccgg tctctaaacg acacagaaga ccaagaaacc ggtgaagagc gctcttctaa    60
ctcactgact gaattaatgt ccggtgagaa gaagtcaccc acag                    104

<210> SEQ ID NO 149
<211> LENGTH: 104
<212> TYPE: DNA
<213> ORGANISM: Artificial sequence
<220> FEATURE:
<223> OTHER INFORMATION: Mammalian

<400> SEQUENCE: 149
agggcaccgg tctctaaaca cgatcacgtg gcttacaggc ggtgaagagc gctcttctaa    60
ccttcccaat gaccttgagg acggtgagaa gaagtcaccc acag                    104

<210> SEQ ID NO 150
<211> LENGTH: 104
<212> TYPE: DNA
<213> ORGANISM: Artificial sequence
<220> FEATURE:
<223> OTHER INFORMATION: Mammalian

<400> SEQUENCE: 150
```
agggcaccgg tctctaaaca acccccacca gacacagtgc ggtgaagagc gctcttctaa    60
cgaagggctg agcaaagttc tcggtgagaa gaagtcaccc acag    104

<210> SEQ ID NO 151
<211> LENGTH: 104
<212> TYPE: DNA
<213> ORGANISM: Artificial sequence
<220> FEATURE:
<223> OTHER INFORMATION: Mammalian

<400> SEQUENCE: 151
agggcaccgg tctctaaaca gaagtccgca tcatgaaggc ggtgaagagc gctcttctaa    60
ccaccgatgt tggggtggtt tcggtgagaa gaagtcaccc acag    104

<210> SEQ ID NO 152
<211> LENGTH: 104
<212> TYPE: DNA
<213> ORGANISM: Artificial sequence
<220> FEATURE:
<223> OTHER INFORMATION: Mammalian

<400> SEQUENCE: 152
agggcaccgg tctctaaacc aaagaagatg gaatttcctc ggtgaagagc gctcttctaa    60
cccaacagca ctgccacttg acggtgagaa gaagtcaccc acag    104

<210> SEQ ID NO 153
<211> LENGTH: 104
<212> TYPE: DNA
<213> ORGANISM: Artificial sequence
<220> FEATURE:
<223> OTHER INFORMATION: Mammalian

<400> SEQUENCE: 153
agggcaccgg tctctaaact cacgatgcag atgcagctgc ggtgaagagc gctcttctaa    60
cagaaagaag acgctttcag acggtgagaa gaagtcaccc acag    104

<210> SEQ ID NO 154
<211> LENGTH: 104
<212> TYPE: DNA
<213> ORGANISM: Artificial sequence
<220> FEATURE:
<223> OTHER INFORMATION: Mammalian

<400> SEQUENCE: 154
agggcaccgg tctctaaacg ataccacttc ccaagttctc ggtgaagagc gctcttctaa    60
caacagtact ttgtaagtat ccggtgagaa gaagtcaccc acag    104

<210> SEQ ID NO 155
<211> LENGTH: 104
<212> TYPE: DNA
<213> ORGANISM: Artificial sequence
<220> FEATURE:
<223> OTHER INFORMATION: Mammalian

<400> SEQUENCE: 155
agggcaccgg tctctaaaca gcttttccaa ggaaagaagc ggtgaagagc gctcttctaa    60
ccacatccac ttcaggccca tcggtgagaa gaagtcaccc acag    104

<210> SEQ ID NO 156
<211> LENGTH: 104
<212> TYPE: DNA
<213> ORGANISM: Artificial sequence

```
<220> FEATURE:
<223> OTHER INFORMATION: Mammalian

<400> SEQUENCE: 156
agggcaccgg tctctaaact gtggcgcact tggtggatgc ggtgaagagc gctcttctaa      60
ccaaagacaa caactacctg ccggtgagaa gaagtcaccc acag                     104

<210> SEQ ID NO 157
<211> LENGTH: 104
<212> TYPE: DNA
<213> ORGANISM: Artificial sequence
<220> FEATURE:
<223> OTHER INFORMATION: Mammalian

<400> SEQUENCE: 157
agggcaccgg tctctaaacc ccggaagcgt gtggattctc ggtgaagagc gctcttctaa      60
ccttcccgtg acggctcagc acggtgagaa gaagtcaccc acag                     104

<210> SEQ ID NO 158
<211> LENGTH: 104
<212> TYPE: DNA
<213> ORGANISM: Artificial sequence
<220> FEATURE:
<223> OTHER INFORMATION: Mammalian

<400> SEQUENCE: 158
agggcaccgg tctctaaacg gacatcgtcc accgggaccc ggtgaagagc gctcttctaa      60
ctgtcgagga gaaggttctc gcggtgagaa gaagtcaccc acag                     104

<210> SEQ ID NO 159
<211> LENGTH: 104
<212> TYPE: DNA
<213> ORGANISM: Artificial sequence
<220> FEATURE:
<223> OTHER INFORMATION: Mammalian

<400> SEQUENCE: 159
agggcaccgg tctctaaacg actggtacct ctgaccctcc ggtgaagagc gctcttctaa      60
cgcagcacga tgcacttgac ccggtgagaa gaagtcaccc acag                     104

<210> SEQ ID NO 160
<211> LENGTH: 104
<212> TYPE: DNA
<213> ORGANISM: Artificial sequence
<220> FEATURE:
<223> OTHER INFORMATION: Mammalian

<400> SEQUENCE: 160
agggcaccgg tctctaaact gaaaaatact tacgaagtcc ggtgaagagc gctcttctaa      60
caacgtgcct cgaccaagaa acggtgagaa gaagtcaccc acag                     104

<210> SEQ ID NO 161
<211> LENGTH: 104
<212> TYPE: DNA
<213> ORGANISM: Artificial sequence
<220> FEATURE:
<223> OTHER INFORMATION: Mammalian

<400> SEQUENCE: 161
agggcaccgg tctctaaacc tgcgcacgat gtagtcatgc ggtgaagagc gctcttctaa      60
cgaaccatgg ttatgatgac gcggtgagaa gaagtcaccc acag                     104
```

<210> SEQ ID NO 162
<211> LENGTH: 104
<212> TYPE: DNA
<213> ORGANISM: Artificial sequence
<220> FEATURE:
<223> OTHER INFORMATION: Mammalian

<400> SEQUENCE: 162
agggcaccgg tctctaaact ctagcttatc gatatgaggc ggtgaagagc gctcttctaa    60
caaactcccc ttgccaataa tcggtgagaa gaagtcaccc acag    104

<210> SEQ ID NO 163
<211> LENGTH: 104
<212> TYPE: DNA
<213> ORGANISM: Artificial sequence
<220> FEATURE:
<223> OTHER INFORMATION: Mammalian

<400> SEQUENCE: 163
agggcaccgg tctctaaacc cccggaagcg tgtggactcc ggtgaagagc gctcttctaa    60
ccttgccgtg ccggttcagc acggtgagaa gaagtcaccc acag    104

<210> SEQ ID NO 164
<211> LENGTH: 104
<212> TYPE: DNA
<213> ORGANISM: Artificial sequence
<220> FEATURE:
<223> OTHER INFORMATION: Mammalian

<400> SEQUENCE: 164
agggcaccgg tctctaaacc atagcaatca gtgagtatgc ggtgaagagc gctcttctaa    60
ccatggcaaa agccccagaa tcggtgagaa gaagtcaccc acag    104

<210> SEQ ID NO 165
<211> LENGTH: 104
<212> TYPE: DNA
<213> ORGANISM: Artificial sequence
<220> FEATURE:
<223> OTHER INFORMATION: Mammalian

<400> SEQUENCE: 165
agggcaccgg tctctaaaca cccactttca aaacaatttc ggtgaagagc gctcttctaa    60
cagtagttct gatttggatt tcggtgagaa gaagtcaccc acag    104

<210> SEQ ID NO 166
<211> LENGTH: 104
<212> TYPE: DNA
<213> ORGANISM: Artificial sequence
<220> FEATURE:
<223> OTHER INFORMATION: Mammalian

<400> SEQUENCE: 166
agggcaccgg tctctaaacg acagcagctc agcaaagacc ggtgaagagc gctcttctaa    60
cccggtggat gtttgggcaa tcggtgagaa gaagtcaccc acag    104

<210> SEQ ID NO 167
<211> LENGTH: 104
<212> TYPE: DNA
<213> ORGANISM: Artificial sequence
<220> FEATURE:
<223> OTHER INFORMATION: Mammalian

<400> SEQUENCE: 167

-continued

```
agggcaccgg tctctaaaca ttgttgctga gatgcttttc ggtgaagagc gctcttctaa     60
cgccctcaag aacctcaaat gcggtgagaa gaagtcaccc acag                     104

<210> SEQ ID NO 168
<211> LENGTH: 104
<212> TYPE: DNA
<213> ORGANISM: Artificial sequence
<220> FEATURE:
<223> OTHER INFORMATION: Mammalian

<400> SEQUENCE: 168
agggcaccgg tctctaaacg acttactgtg gcagctttgc ggtgaagagc gctcttctaa     60
ccgtaagatc tctgggcaag ccggtgagaa gaagtcaccc acag                     104

<210> SEQ ID NO 169
<211> LENGTH: 104
<212> TYPE: DNA
<213> ORGANISM: Artificial sequence
<220> FEATURE:
<223> OTHER INFORMATION: Mammalian

<400> SEQUENCE: 169
agggcaccgg tctctaaacg aagctgactg actttggctc ggtgaagagc gctcttctaa     60
cggtgtgact tgggcaacac ccggtgagaa gaagtcaccc acag                     104

<210> SEQ ID NO 170
<211> LENGTH: 104
<212> TYPE: DNA
<213> ORGANISM: Artificial sequence
<220> FEATURE:
<223> OTHER INFORMATION: Mammalian

<400> SEQUENCE: 170
agggcaccgg tctctaaacc ctgggccgcc gcctcgggcc ggtgaagagc gctcttctaa     60
cagccggcgt cggaggcgcg gcggtgagaa gaagtcaccc acag                     104

<210> SEQ ID NO 171
<211> LENGTH: 104
<212> TYPE: DNA
<213> ORGANISM: Artificial sequence
<220> FEATURE:
<223> OTHER INFORMATION: Mammalian

<400> SEQUENCE: 171
agggcaccgg tctctaaaca acaacaggat catcttcagc ggtgaagagc gctcttctaa     60
cctggacaag tagtagctgt tcggtgagaa gaagtcaccc acag                     104

<210> SEQ ID NO 172
<211> LENGTH: 104
<212> TYPE: DNA
<213> ORGANISM: Artificial sequence
<220> FEATURE:
<223> OTHER INFORMATION: Mammalian

<400> SEQUENCE: 172
agggcaccgg tctctaaact cagactttga gcatacgatc ggtgaagagc gctcttctaa     60
cgtgactgca tcaaacccca ccggtgagaa gaagtcaccc acag                     104

<210> SEQ ID NO 173
<211> LENGTH: 104
<212> TYPE: DNA
```

<213> ORGANISM: Artificial sequence
<220> FEATURE:
<223> OTHER INFORMATION: Mammalian

<400> SEQUENCE: 173
agggcaccgg tctctaaaca atgggctggc tgcaaaggcc ggtgaagagc gctcttctaa    60
ctgaaactcg gcggggccca gcggtgagaa gaagtcaccc acag                    104

<210> SEQ ID NO 174
<211> LENGTH: 104
<212> TYPE: DNA
<213> ORGANISM: Artificial sequence
<220> FEATURE:
<223> OTHER INFORMATION: Mammalian

<400> SEQUENCE: 174
agggcaccgg tctctaaacc aaaacttcaa ataccatgcc ggtgaagagc gctcttctaa    60
ctccttaatg aattcctaga tcggtgagaa gaagtcaccc acag                    104

<210> SEQ ID NO 175
<211> LENGTH: 104
<212> TYPE: DNA
<213> ORGANISM: Artificial sequence
<220> FEATURE:
<223> OTHER INFORMATION: Mammalian

<400> SEQUENCE: 175
agggcaccgg tctctaaact tggcaaatc cccagtactc ggtgaagagc gctcttctaa     60
ctgacagaag cagaacggtt tcggtgagaa gaagtcaccc acag                    104

<210> SEQ ID NO 176
<211> LENGTH: 104
<212> TYPE: DNA
<213> ORGANISM: Artificial sequence
<220> FEATURE:
<223> OTHER INFORMATION: Mammalian

<400> SEQUENCE: 176
agggcaccgg tctctaaact atgcagaaca cctgcaaatc ggtgaagagc gctcttctaa    60
caggagtata tacattttct tcggtgagaa gaagtcaccc acag                    104

<210> SEQ ID NO 177
<211> LENGTH: 104
<212> TYPE: DNA
<213> ORGANISM: Artificial sequence
<220> FEATURE:
<223> OTHER INFORMATION: Mammalian

<400> SEQUENCE: 177
agggcaccgg tctctaaacg cgcatcacga tcacggcgc ggtgaagagc gctcttctaa     60
caggctgaac gtccaggtca ccggtgagaa gaagtcaccc acag                    104

<210> SEQ ID NO 178
<211> LENGTH: 104
<212> TYPE: DNA
<213> ORGANISM: Artificial sequence
<220> FEATURE:
<223> OTHER INFORMATION: Mammalian

<400> SEQUENCE: 178
agggcaccgg tctctaaacg ctctgccacg cccttagatc ggtgaagagc gctcttctaa    60
catgcttctt ttgagggtgg acggtgagaa gaagtcaccc acag                    104

<210> SEQ ID NO 179
<211> LENGTH: 104
<212> TYPE: DNA
<213> ORGANISM: Artificial sequence
<220> FEATURE:
<223> OTHER INFORMATION: Mammalian

<400> SEQUENCE: 179

```
agggcaccgg tctctaaacc cggcaggaga ggctgtgggc ggtgaagagc gctcttctaa      60
cgcccccggg acccagccag gcggtgagaa gaagtcaccc acag                      104
```

<210> SEQ ID NO 180
<211> LENGTH: 104
<212> TYPE: DNA
<213> ORGANISM: Artificial sequence
<220> FEATURE:
<223> OTHER INFORMATION: Mammalian

<400> SEQUENCE: 180

```
agggcaccgg tctctaaacg caagcttaaa acccacagcc ggtgaagagc gctcttctaa      60
cccctgaaca gacacttccg ccggtgagaa gaagtcaccc acag                      104
```

<210> SEQ ID NO 181
<211> LENGTH: 104
<212> TYPE: DNA
<213> ORGANISM: Artificial sequence
<220> FEATURE:
<223> OTHER INFORMATION: Mammalian

<400> SEQUENCE: 181

```
agggcaccgg tctctaaact ctggtagata cataatctgc ggtgaagagc gctcttctaa      60
cagaaatacg atcaaaacct ccggtgagaa gaagtcaccc acag                      104
```

<210> SEQ ID NO 182
<211> LENGTH: 104
<212> TYPE: DNA
<213> ORGANISM: Artificial sequence
<220> FEATURE:
<223> OTHER INFORMATION: Mammalian

<400> SEQUENCE: 182

```
agggcaccgg tctctaaaca gcgtgacgcc acgcgggtgc ggtgaagagc gctcttctaa      60
cgacgccatc cagcaccatc tcggtgagaa gaagtcaccc acag                      104
```

<210> SEQ ID NO 183
<211> LENGTH: 104
<212> TYPE: DNA
<213> ORGANISM: Artificial sequence
<220> FEATURE:
<223> OTHER INFORMATION: Mammalian

<400> SEQUENCE: 183

```
agggcaccgg tctctaaacc atcggcagca ggaagctggc ggtgaagagc gctcttctaa      60
ccgcgcacct tggcaaagga gcggtgagaa gaagtcaccc acag                      104
```

<210> SEQ ID NO 184
<211> LENGTH: 104
<212> TYPE: DNA
<213> ORGANISM: Artificial sequence
<220> FEATURE:
<223> OTHER INFORMATION: Mammalian

```
<400> SEQUENCE: 184
agggcaccgg tctctaaaca catcgtccgg tgagttgggc ggtgaagagc gctcttctaa      60
ctcgccatcc cagcttcccc acggtgagaa gaagtcaccc acag                     104

<210> SEQ ID NO 185
<211> LENGTH: 104
<212> TYPE: DNA
<213> ORGANISM: Artificial sequence
<220> FEATURE:
<223> OTHER INFORMATION: Mammalian

<400> SEQUENCE: 185
agggcaccgg tctctaaacg actctgttgc tttggaggtc ggtgaagagc gctcttctaa      60
cttcagccgc cacagaacct gcggtgagaa gaagtcaccc acag                     104

<210> SEQ ID NO 186
<211> LENGTH: 104
<212> TYPE: DNA
<213> ORGANISM: Artificial sequence
<220> FEATURE:
<223> OTHER INFORMATION: Mammalian

<400> SEQUENCE: 186
agggcaccgg tctctaaacg aatatttcat gtaatatgac ggtgaagagc gctcttctaa      60
caatagtgtc ttgtaagtat acggtgagaa gaagtcaccc acag                     104

<210> SEQ ID NO 187
<211> LENGTH: 104
<212> TYPE: DNA
<213> ORGANISM: Artificial sequence
<220> FEATURE:
<223> OTHER INFORMATION: Mammalian

<400> SEQUENCE: 187
agggcaccgg tctctaaacg agggtcggct ggcccgggcc ggtgaagagc gctcttctaa      60
cggatgaact cgccccacct ccggtgagaa gaagtcaccc acag                     104

<210> SEQ ID NO 188
<211> LENGTH: 104
<212> TYPE: DNA
<213> ORGANISM: Artificial sequence
<220> FEATURE:
<223> OTHER INFORMATION: Mammalian

<400> SEQUENCE: 188
agggcaccgg tctctaaaca ttactgatgt cttacttgcc ggtgaagagc gctcttctaa      60
cgaactattg gttggtgatg tcggtgagaa gaagtcaccc acag                     104

<210> SEQ ID NO 189
<211> LENGTH: 104
<212> TYPE: DNA
<213> ORGANISM: Artificial sequence
<220> FEATURE:
<223> OTHER INFORMATION: Mammalian

<400> SEQUENCE: 189
agggcaccgg tctctaaaca tcaccttagg tttcaccagc ggtgaagagc gctcttctaa      60
cggatcttca gctccatcag gcggtgagaa gaagtcaccc acag                     104

<210> SEQ ID NO 190
<211> LENGTH: 104
```

```
<212> TYPE: DNA
<213> ORGANISM: Artificial sequence
<220> FEATURE:
<223> OTHER INFORMATION: Mammalian

<400> SEQUENCE: 190
agggcaccgg tctctaaacg aacgcacccg gctcacctcc ggtgaagagc gctcttctaa      60
cacattgaca acatgaccat gcggtgagaa gaagtcaccc acag                      104

<210> SEQ ID NO 191
<211> LENGTH: 104
<212> TYPE: DNA
<213> ORGANISM: Artificial sequence
<220> FEATURE:
<223> OTHER INFORMATION: Mammalian

<400> SEQUENCE: 191
agggcaccgg tctctaaaca cgagagtgcc tacctctgtc ggtgaagagc gctcttctaa      60
cggccctgca gcacccctac tcggtgagaa gaagtcaccc acag                      104

<210> SEQ ID NO 192
<211> LENGTH: 104
<212> TYPE: DNA
<213> ORGANISM: Artificial sequence
<220> FEATURE:
<223> OTHER INFORMATION: Mammalian

<400> SEQUENCE: 192
agggcaccgg tctctaaacc cgagtgggat gaccgttccc ggtgaagagc gctcttctaa      60
cccgctcacc aggtctttga ccggtgagaa gaagtcaccc acag                      104

<210> SEQ ID NO 193
<211> LENGTH: 104
<212> TYPE: DNA
<213> ORGANISM: Artificial sequence
<220> FEATURE:
<223> OTHER INFORMATION: Mammalian

<400> SEQUENCE: 193
agggcaccgg tctctaaacg ccagcagcgt gtacatgatc ggtgaagagc gctcttctaa      60
ctcgcatgtc caggtggagc acggtgagaa gaagtcaccc acag                      104

<210> SEQ ID NO 194
<211> LENGTH: 104
<212> TYPE: DNA
<213> ORGANISM: Artificial sequence
<220> FEATURE:
<223> OTHER INFORMATION: Mammalian

<400> SEQUENCE: 194
agggcaccgg tctctaaaca ggagttgcca ccactgttgc ggtgaagagc gctcttctaa      60
cttaggagac aaggacggca gcggtgagaa gaagtcaccc acag                      104

<210> SEQ ID NO 195
<211> LENGTH: 104
<212> TYPE: DNA
<213> ORGANISM: Artificial sequence
<220> FEATURE:
<223> OTHER INFORMATION: Mammalian

<400> SEQUENCE: 195
agggcaccgg tctctaaacg aggatgatgg gagctgaagc ggtgaagagc gctcttctaa      60
```

```
cgcgcctatg atgtgagtgt ccggtgagaa gaagtcaccc acag            104
```

<210> SEQ ID NO 196
<211> LENGTH: 104
<212> TYPE: DNA
<213> ORGANISM: Artificial sequence
<220> FEATURE:
<223> OTHER INFORMATION: Mammalian

<400> SEQUENCE: 196

```
agggcaccgg tctctaaacg tgacaccgcg tgtgcaccgc ggtgaagagc gctcttctaa   60
ccgtacgagc cgtacctggc gcggtgagaa gaagtcaccc acag                   104
```

<210> SEQ ID NO 197
<211> LENGTH: 104
<212> TYPE: DNA
<213> ORGANISM: Artificial sequence
<220> FEATURE:
<223> OTHER INFORMATION: Mammalian

<400> SEQUENCE: 197

```
agggcaccgg tctctaaacg tgcacatctg cggagagagc ggtgaagagc gctcttctaa   60
cggccagctc cccacttgcc gcggtgagaa gaagtcaccc acag                   104
```

<210> SEQ ID NO 198
<211> LENGTH: 104
<212> TYPE: DNA
<213> ORGANISM: Artificial sequence
<220> FEATURE:
<223> OTHER INFORMATION: Mammalian

<400> SEQUENCE: 198

```
agggcaccgg tctctaaacg taaccacaca ctctaagttc ggtgaagagc gctcttctaa   60
cggactggat taaatttaag acggtgagaa gaagtcaccc acag                   104
```

<210> SEQ ID NO 199
<211> LENGTH: 104
<212> TYPE: DNA
<213> ORGANISM: Artificial sequence
<220> FEATURE:
<223> OTHER INFORMATION: Mammalian

<400> SEQUENCE: 199

```
agggcaccgg tctctaaact atcgacctca atcgcggcgc ggtgaagagc gctcttctaa   60
cgacccgaag tcgatgagct tcggtgagaa gaagtcaccc acag                   104
```

<210> SEQ ID NO 200
<211> LENGTH: 104
<212> TYPE: DNA
<213> ORGANISM: Artificial sequence
<220> FEATURE:
<223> OTHER INFORMATION: Mammalian

<400> SEQUENCE: 200

```
agggcaccgg tctctaaaca cacgggcgcc actagtactc ggtgaagagc gctcttctaa   60
cgccgcccgg ggtgaagctg gcggtgagaa gaagtcaccc acag                   104
```

<210> SEQ ID NO 201
<211> LENGTH: 104
<212> TYPE: DNA
<213> ORGANISM: Artificial sequence
<220> FEATURE:
<223> OTHER INFORMATION: Mammalian -continued

```
<400> SEQUENCE: 201
agggcaccgg tctctaaacc atgacggata cctggagtcc ggtgaagagc gctcttctaa      60
ctcttcgcag gacaccgcct ccggtgagaa gaagtcaccc acag                      104

<210> SEQ ID NO 202
<211> LENGTH: 104
<212> TYPE: DNA
<213> ORGANISM: Artificial sequence
<220> FEATURE:
<223> OTHER INFORMATION: Mammalian

<400> SEQUENCE: 202
agggcaccgg tctctaaacg tcagtaagag aaggccaagc ggtgaagagc gctcttctaa      60
cgcacgcgga tgctcatgat gcggtgagaa gaagtcaccc acag                      104

<210> SEQ ID NO 203
<211> LENGTH: 104
<212> TYPE: DNA
<213> ORGANISM: Artificial sequence
<220> FEATURE:
<223> OTHER INFORMATION: Mammalian

<400> SEQUENCE: 203
agggcaccgg tctctaaaca ggcggacaag gagagcttcc ggtgaagagc gctcttctaa      60
cgcacggcgc ccacctggta ccggtgagaa gaagtcaccc acag                      104

<210> SEQ ID NO 204
<211> LENGTH: 76
<212> TYPE: DNA
<213> ORGANISM: Artificial sequence
<220> FEATURE:
<223> OTHER INFORMATION: Mammalian

<400> SEQUENCE: 204
gttttagagc tagaaatagc aagttaaaat aaggctagtc cgttatcaac ttgaaaaagt      60
ggcaccgagt cggtgc                                                      76
```

METHODS FOR GENERATING LIBRARIES WITH CO-VARYING REGIONS OF POLYNULEOTIDES FOR GENOME MODIFICATION

CROSS-REFERENCE TO RELATED APPLICATIONS

The present application claims the benefit of U.S. 61/939,207 filed Feb. 12, 2014; U.S. 61/974,873 filed Mar. 3, 2014; and U.S. 62/075,601 filed Nov. 5, 2014, incorporated by reference in their entirety for all purposes.

REFERENCE TO A SEQUENCE LISTING

This application includes an electronic sequence listing in a file named "452339SEQLST.TXT" created on Feb. 10, 2015 and containing 68,557 bytes, which is hereby incorporated by reference.

BACKGROUND OF THE INVENTION

In the past decade, a great deal of progress has been made in the field of targeted genome engineering. Technologies such as designer zinc finger nucleases (ZFNs), transcriptional activator-like effector nucleases (TALENs), and homing meganucleases have made site-specific genome modifications a reality in many different model organisms ranging from zebrafish to mammalian cells. Based on the results to date, however, genome editing tools that are efficient, flexible, and cost-effective have remained elusive to the general research community. The recent discovery of the type II prokaryotic CRISPR (Clustered Regularly Interspaced Short Palindromic Repeats) system, originally discovered in the bacterium *Streptococcus pyogenes* as a mechanism to defend against viruses and foreign DNA, has provided yet another tool for targeted genome engineering, this time taking advantage of a system that uses small RNAs as guides to cleave DNA in a sequence-specific manner. With its ease in designing guide sequences to target specific sequences (unlike ZFNs and TALENs where construct assembly can be laborious and time-consuming), as well as its targeting efficiency, this system has the potential to be a disruptive technology in the field of genome-engineering.

The CRISPR/CRISPR-associated (Cas) system involves 1) retention of foreign genetic material, called "spacers", in clustered arrays in the host genome, 2) expression of short guiding RNAs (crRNAs) from the spacers, 3) binding of the crRNAs to specific portions of the foreign DNA called protospacers and 4) degradation of protospacers by CRISPR-associated nucleases (Cas). A well-characterized Type II CRISPR system has been previously described in the bacterium *Streptococcus pyogenes*, where four genes (Cas9, Cas1, Cas2, Csn1) and two non-coding small RNAs (pre-crRNA and tracrRNA) act in concert to target and degrade foreign DNA in a sequence-specific manner [Jinek et. al. 2012]. The specificity of binding to the foreign DNA is controlled by the non-repetitive spacer elements in the pre-crRNA, which upon transcription along with the tracrRNA, directs the Cas9 nuclease to the protospacer:crRNA heteroduplex and induces double-strand breakage (DSB) formation. Additionally, the Cas9 nuclease cuts the DNA only if a specific sequence known as protospacer adjacent motif (PAM) is present immediately downstream of the protospacer sequence, whose canonical sequence in *S. pyogenes* is 5'-NRG-3', where N refers to any nucleotide and R refers to A or G.

There are a myriad of examples in the art disclosing variations on themes of multiple promoters used in the same vector.

One potential problem with vectors designed to accommodate expression of two inserts under control of separate promoters is that insertion of both inserts may require sequential cloning and isolation steps as well as using of different selection markers for such inserts. The additional effort becomes even more of a concern if it is desired to introduce libraries of inserts rather than single inserts under control of each promoter and only select combinations of the inserts from the respective libraries are compatible with one another.

Therefore, there remains a need for new classes of expression vectors and related methods suitable for expression of multiple small guide RNA molecules or other nucleic acids intended to be expressed in a pair-wise fashion.

SUMMARY OF THE INVENTION

The invention provides methods of inserting a pair of nucleic acid segments into a vector. Such methods involve (a) synthesizing an oligonucleotide comprising the paired segments; (b) performing an assembly reaction between the oligonucleotide and a spacer oligonucleotide to form a nucleic acid in which the spacer oligonucleotide is to one side of the oligonucleotide comprising the paired segments; (c) circularizing the nucleic acid; (d) cleaving the circularized nucleic acid at a site that generates a linear nucleic acid in which the spacer oligonucleotide is flanked by the paired segments; and (e) inserting the linear nucleic acid into a vector.

Optionally the assembly reaction is a template-directed amplification performed with a template, a forward primer and a reverse primer, the spacer oligonucleotide being the template, and the oligonucleotide comprising the paired segments being the reverse primer. Optionally, the 5' ends of the forward and reverse primer are complementary and annealing of these 5' ends or their complements on opposing strands circularizes the nucleic acid. Optionally, the circularized nucleic acid is cleaved in at least one site between the paired segments such that the distance (by number of separating nucleotides) between the linked paired segments is greater in the linearized nucleic acid than in the circularized nucleic acid. Optionally the template is double-stranded and the forward and reverse primers are single-stranded. Optionally, the spacer oligonucleotide comprises a promoter, which is in operable linkage with one of the paired segments in the linear nucleic acids. Optionally, the promoter is an RNA pol III promoter. Optionally, the spacer further comprises a transcriptional terminator upstream of the promoter. Optionally, the paired nucleic acid segments encode guide RNAs and the spacer further encodes a scaffold RNA upstream from the terminator wherein one of the guide RNAs and the scaffold RNA are in operable linkage with one another. Optionally, wherein the spacer oligonucleotide comprises a promoter and encodes a scaffold RNA, and the vector comprises a promoter and encodes a scaffold RNA and the vector is adapted such that on insertion of the nucleic acid into the vector and one guide RNA is operably linked to a scaffold RNA encoded by the spacer and a promoter from the vector and the other guide RNA is operably linked to a scaffold RNA encoded by the vector and the promoter of the spacer. Optionally, the vector encodes a RNA-guided nuclease selected from Cas9, mutant Cas9 with nickase activity (Cas9n) and mutant Cas9 with no activity (dCas9). Optionally, the methods also involve introducing the vector resulting from such method into a host cell, wherein the vector modifies the genome of the host cell and, wherein the host cell is a eukaryotic cell or a bacterial cell.

The method can be performed in parallel for a plurality of pairs of nucleic acid segments; wherein step (a) comprising synthesizing a plurality of oligonucleotides comprising the plurality of paired segments; step (b) comprising performing the assembly reaction between the paired segments and the spacer segment to generate a plurality of nucleic acids in which the spacer oligonucleotide is to one side of the plurality of oligonucleotides comprising the paired segments; step (c) comprising circularizing the nucleic acids; step (d) comprising cleaving the nucleic acids; and step (e) comprising inserting the linear nucleic acids so that different molecules of the vector receive different linear nucleic acids. The plurality of pairs of nucleic acids can have 50 to 100,000 distinct linked guide RNAs.

In some embodiments, the synthesized paired segments have compatible ends to an expression vector and are inserted into the vector in a simple cloning step to generate a circular nucleic acid. Optionally, the circular nucleic acid is cleaved in at least one site between the paired segments such that a spacer oligonucleotide with compatible ends can be inserted between the paired segments. Optionally, the spacer oligonucleotide comprises a promoter, which is in operable linkage with one of the paired segments in the linear nucleic acids. Optionally, the promoter is an RNA pol III promoter. Optionally, the spacer further comprises a transcriptional terminator upstream of the promoter. Optionally, the paired nucleic acid segments encode guide RNAs and the spacer further encodes a scaffold RNA upstream from the terminator wherein one of the guide RNAs and the scaffold RNA are in operable linkage with one another. Optionally, wherein the spacer oligonucleotide comprises a promoter and encodes a scaffold RNA, and the vector comprises a promoter and encodes a scaffold RNA and the vector is adapted such that on insertion of the nucleic acid into the vector and one guide RNA is operably linked to a scaffold RNA encoded by the spacer and a promoter from the vector and the other guide RNA is operably linked to a scaffold RNA encoded by the vector and the promoter of the spacer. Optionally, the vector encodes a RNA-guided nuclease selected from Cas9, mutant Cas9 with nickase activity (Cas9n) and mutant Cas9 with no activity (dCas9). Optionally, the methods also involve introducing the vector resulting from such method into a host cell, wherein the vector modifies the genome of the host cell and, wherein the host cell is a eukaryotic cell or a bacterial cell.

The method can be performed in parallel for a plurality of pairs of nucleic acid segments; wherein step (a) comprising synthesizing a plurality of oligonucleotides comprising the plurality of paired segments; step (b) comprising inserting the plurality of oligonucleotides so that different molecules of vector receive different paired segments of nucleic acids to generate a plurality of circular nucleic acids; step (c) comprising linearizing the nucleic acids between the paired segments; step (d) comprising inserting the spacer oligonucleotide such that the paired segments are in operable linkage to a promoter in the vector and the other to the promoter in the spacer. The plurality of pairs of nucleic acids comprise 50 to 100,000 distinct linked guide RNAs.

In any of the methods described, the paired nucleic acid segments can encode guide RNAs wherein: a) the guide RNAs have partially overlapping sequences; and b) the guide RNAs are each 15-30 nucleotide long. Optionally, the guide RNAs comprise at least 50% of polynucleotides that are linked in a pre-determined way. The invention further provides kits comprising (a) a vector comprising: a promoter transcribed by RNA polymerase III and a nucleic acid sequence encoding a Cas9 nuclease operably linked to a second promoter; and (b) a spacer oligonucleotide comprising a third promoter transcribed by RNA polymerase III. The vector is adapted for insertion of a nucleic acid fragment comprising the spacer oligonucleotide flanked by paired nucleic acid segments, whereby one of the pair segments is expressible from the promoter of the vector transcribed by the polymerase III of the spacer oligonucleotide and the other of the paired segments is expressible from the third promoter of the spacer. Optionally, the paired segments encode guide RNAs, the spacer oligonucleotide comprises the second promoter, and upstream therefrom a transcriptional terminator and a segment encoding a scaffold RNA, and the vector further comprises a segment encoding a scaffold RNA, wherein the vector is adapted for insertion of the nucleic acid fragment, wherein one guide RNA is in operable linkage with the promoter of the vector and a guide RNA of the spacer oligonucleotide and the other guide RNA is in operable linkage with the promoter on the spacer oligonucleotide and the scaffold RNA of the vector. Optionally, such a kit also includes a primer for priming template directed synthesis from the spacer oligonucleotide. Optionally, the CAS9 is a mutant CAS9 with nickase activity (Cas9n) or no activity (dCas9). In one embodiment, two gRNAs are transcribed from a single construct wherein each gRNA is expressed using the U6 or H1 variants of the RNA pol III promoter wherein the two RNA pol III promoters can be placed in a tandem orientation driving expression of gsRNAs in the same direction (FIG. 1). In another embodiment, two gsRNAs are transcribed from a single construct wherein each gsRNA is expressed using the U6 or H1 variants of the RNA pol III promoter wherein the two RNA pol III promoters can be placed in opposite orientation driving expression of gsRNAs in opposite directions. The two gsRNAs are offset pairs that direct the Cas9n to opposite strands of the same genomic locus.

In a preferred embodiment, a genome modifying construct comprising two RNA pol III promoters U6.1 (SEQ ID NO: 3) and U6-8cc (SEQ ID NO: 1) are used to direct expression of two gRNA molecules from expression cassettes that are in tandem orientation in the same direction. Additionally, the genome modifying construct comprises an expression cassette capable of driving high protein expression, for example a promoter comprising the CMV immediate early enhancer such as a mammalian promoter selected from CMV, CAG and CBh or the EF1 alpha promoter. These promoters direct strong constitutive expression of Cas9n (nickase) or Cas9 (wild type) or dCas9 (nuclease inactive). Expression of Cas9 nuclease may be monitored by coupling its expression to that of a fluorescent reporter protein, for example via an IRES or 2A/CHYSEL element. The genome modifying construct may further comprise a bacterial resistance marker and a bacterial origin of replication.

In another preferred embodiment, a genome modifying vector comprising two prokaryotic promoters, either constitutive or inducible is used to direct expression of two gRNA molecules from expression cassettes that are in tandem orientation in the same direction in a bacterial cell. Additionally, the genome modifying vector comprises an expression cassette capable of driving high protein expression, for example an inducible promoter comprising the rhamnose inducible promoter rhaBAD, IPTG inducible promoters T5 or T7. In other embodiments, the promoter is constitutive. These promoters direct constitutive or inducible expression of Cas9n (nickase) or Cas9 (wild type) or dCas9 (nuclease inactive). Expression of Cas9 nuclease may be monitored by coupling its expression to that of a fluorescent reporter protein, for example via fusion. In preferred embodiments, the genome modifying vector may comprise a recombinase, for example the lambda red operon genes gam, exo and beta to facilitate recombination events and double strand break repair in *E. coli*. The genome modifying vector may further comprise a bacterial resistance marker, a counter-selectable marker and a bacterial origin of replication. In some preferred embodiments, the bacterial origin of replication is temperature sensitive. In some embodiments, donor insert fragment(s) to be introduced into the genome at sites of Cas9 mediated double stranded breaks are incorporated into the genome modifying vector. In other embodiments, the donor insert fragment(s) are introduced as a separate polynucleotide that is either linear or circular.

In another embodiment, two gRNAs are transcribed from a single construct wherein each gRNA is expressed using the U6 or H1 variants of the RNA pol III promoter wherein the gRNAs direct Cas9 or dCas9 to different genomic loci. In one embodiment, the RNA pol III promoters can be placed in a tandem orientation driving expression of two gRNAs in the same direction. In another embodiment, the RNA pol III promoters can be placed in opposite orientation.

In other embodiments, two gRNAs transcribed from a single construct using two RNA pol III promoters wherein the gRNA directs dCas9 to different genomic loci along the target gene. Multiple gRNAs can also be used simultaneously to regulate multiple genes or to synergistically control a single gene for enhanced repression. They can also be used for tuning silencing to achieve a moderate level of gene repression.

In additional embodiments, the Cas9 or Cas9n or 'inactive' dCas9 can be coupled to a reporter or selectable protein, for example any fluorescent or chromogenic protein. This serves as a positive readout for successful transfection and to determine transfection efficiency. In other embodiments, multiple gRNAs can be expressed in a single construct, as paired gRNAs directing Cas9n or dCas9 to different genomic loci.

Additional embodiments with three or more RNA pol III promoters that are either the same or different, directing expression of three or more gRNA molecules in the same genome modifying construct is within the scope of this invention.

It is frequently advantageous to link the expression of gRNAs so that two or more specific gRNAs may be expressed in the same cell at the same time. For example, it may be desirable to target two or more specific genes within the same cell using a construct expressing a cas9 nuclease that causes double-stranded breaks. In another application, it is frequently desirable to express two gRNAs targeted to the same gene using a cas9 nuclease that breaks only one strand of the genome (a Cas9 nickase). In these cases, a useful genome editing event will only occur if the two gRNAs can be expressed from the same construct. The reason for this can be appreciated from the following example. Consider a library of 20 gRNAs, consisting of 2 gRNAs targeted to each of 10 genes. If a cell takes up two constructs at random, the probability of the cell taking up 2 different gRNAs targeting a single gene is about 5%. If a library of constructs is created in which a sequence encoding a first gRNA targeting one of 10 genes is randomly joined with a second gRNA targeting one of 10 genes, the probability that the two gRNAs target the same gene is about 10%. For a library targeting 100 genes, the probability is about 1%; in other words, only 1% of the constructs in a library targeting 100 genes are functional if the two gRNAs are linked randomly and two specific gRNAs are required to edit a specific gene sequence. In general, members of larger libraries have a smaller chance of containing sequences encoding two or more specific gRNAs unless the sequences can be combined in a directed way.

The present invention provides a method for physically linking predetermined combinations of sequences encoding gRNAs, so that a library of genome editing constructs comprises at least 10%, at least 15%, at least 20%, at least 25%, at least 30%, at least 35%, at least 40%, at least 45%, at least 50%, at least 55%, at least 60%, at least 65%, at least 70% or more members where two or more gRNAs are targeted to: the same gene, two or more genes that are functionally related in the same pathway, two or more genes in different pathways. In some embodiments, a library of distinct linked gRNAs may be directed to a family of functionally related genes, for example calmodulin dependent protein kinases, mitogen activated protein kinases (MAP/ERK kinases) including Raf kinase (MAPKKK), MEK (MAPKK), MAPK (also known as ERK), JAK kinases, phosphatidylinositol kinases including phosphatidylinositol 3,4,5-triphosphate (PIPS) and phosphatidylinositol 3-phosphate (PI3P), cyclin-dependent kinases (CDK5), sphingosine kinases whose receptor is a GPCR and has the ability to regulate G-protein signaling, carbohydrate kinases including hexokinase and phosphofructokinase, riboflavin kinase, thymidine kinase; GPCRs include receptors for sensory signal mediators (example, light and olfactory stimulatory molecules); adenosine, bombesin, bradykinin, endothelin, γ-aminobutyric acid (GABA), hepatocyte growth factor (HGF), melanocortins, neuropeptide Y, opioid peptides, opsins, somatostatin, GH, tachykinins, members of the vasoactive intestinal peptide family, and vasopressin; biogenic amines (example, dopamine, epinephrine, norepinephrine, histamine, glutamate (metabotropic effect), glucagon, acetylcholine (muscarinic effect), and serotonin); chemokines; lipid mediators of inflammation (example, prostaglandins, prostanoids, platelet-activating factor, and leukotrienes); and peptide hormones (example, calcitonin, C5a anaphylatoxin, follicle-stimulating hormone (FSH), gonadotropin-releasing hormone (GnRH), neurokinin, thyrotropin-releasing hormone (TRH), cannabinoids, and oxytocin). GPCRs that act as receptors for stimuli that have not yet been identified, known as orphan receptors; phosphatases involved in signal transduction pathways including cyclin dependent phosphatases, tyrosine-specific phosphatases (example PTP1B), serine/threonine specific phosphatases (example PP2C, PPP2CA), dual specificity phosphatases (example VHR, DUSP1-DUSP-28), histidine phosphatase (PHP), lipid phosphatase; proteases including serine proteases chymotrypsin A, dipeptidase, signal peptidases, nucleoporins, lactoferrin, threonine proteases ornithine acetyl transferase, cysteine proteases TEV-protease, actinidain, bromolain, calpains, caspases, cathepsins, Mir1-CP, papain, aspartate proteases BACE, cathepsin D, cathepsin E, chymosin, napsin, nepenthesin, pepsin, plasmepsin, presenilin, renin, HIV-protease, metalloproteases MMPs collagenases, gelatinase, stromolysin 1-4, matrilysin or PUMP-1, matrilysin 2, neutrophil collagenase, macrophage metalloelastase, MT1-MMP, MT2-MMP, MT3-MMP, enamelysin, X-MMP, CA-MMP, epilysin; extracellular receptors including receptor tyrosine kinases (RTKs), integrin receptors, toll-like receptors (TLRs), ligand-gated ion channel receptors, intracellular receptors such as nuclear and cytoplasmic receptors that encode hormones, neurotransmitters, paracrine/autocrine agents. Such libraries of two or more linked gRNAs are advantageous for creating cell lines with enhanced expression properties, enhanced attachment properties, replication properties or any other desirable property and to determine functional effects of genome modifications associated with a specific class of targets.

In some embodiments, a library comprises constructs, wherein the two or more linked gRNAs in each construct are directed to the first exon of a genomic locus. In some embodiments the linked gRNAs in a construct are directed to the same genomic locus. In some embodiments the linked gRNAs in a construct are directed to different genomic loci. In some embodiments the linked gRNAs in a construct are directed to the same genomic locus; in some embodiments the construct further comprises a Cas9 nickase, such that nicking targeted by the linked gRNAs collectively causes a double-stranded break at the genomic locus. In some embodiments each construct comprises sequences expressing two gRNAs.

In some embodiments a library comprises linked gRNAs targeted to the first exons of a functionally related family of genes, for example the first exons of a family of kinases, the first exons of a family of GPCRs, the first exons of a family of phosphatases, the first exons of a family of proteases, the first exons of a family of receptors and the like. In some embodiments, each of the linked gRNAs in a construct is directed to different functionally linked genomic loci of interest. In some embodiments, each of the linked gRNAs in a construct is directed to the same genomic locus.

In some embodiments, a library of linked gRNAs is constructed in a single step, wherein linked gRNAs are transcribed from a single construct using two RNA pol III promoters. A library of linked gRNA constructs may comprise about at least 50 different constructs, about at least 200, different constructs, about at least 500 different constructs, about at least 1,000 different constructs, about at least 2,000 different constructs, about at least 5,000 different constructs, about at least 7,000 different constructs, about at least 10,000 different constructs, or about at least 20,000 different constructs. In some embodiments at least 30% of the gRNAs in the library are linked in a pre-determined way, in some embodiments at least 40% of the gRNAs in the library are linked in a pre-determined way, in some embodiments at least 50% of the gRNAs in the library are linked in a pre-determined way, in some embodiments at least 60% of the gRNAs in the library are linked in a pre-determined way, in some embodiments at least 70% of the gRNAs in the library are linked in a pre-determined way, in some embodiments at least 80% of the gRNAs in the library are linked in a pre-determined way. In some embodiments the linked gRNAs are pairs of gRNAs targeted to different strands of the same gene such that nicking by a Cas9 nickase that is targeted by the linked gRNA pair causes a double-stranded break at the genomic locus.

Methods to construct the library of linked gRNAs in a single step wherein each of the linked gRNAs are transcribed from a single construct are another aspect of this invention. These methods comprise producing a first linear polynucleotide, circularizing the first linear polynucleotide, and then linearizing the circular polynucleotide at a position other than the original join to produce a second linear polynucleotide. By doing so, sequences that were close together in the first linear polynucleotide may be far apart in the second linear polynucleotide. Such a procedure also permutates the sequences in the polynucleotide, for example sequence elements may be ordered A, B, C, D, E in the first linear polynucleotide, while the same elements are ordered B, C, D, E, A in the second linear polynucleotide (FIG. 4A).

In some embodiments sequences A and B are more than 100 nucleotides further apart in the second linear polynucleotide than in the first, in some embodiments sequences A and B are more than 200 nucleotides further apart in the second linear polynucleotide than in the first, in some embodiments sequences A and B are more than 300 nucleotides further apart in the second linear polynucleotide than in the first, in some embodiments sequences A and B are more than 400 nucleotides further apart in the second linear polynucleotide than in the first. In some embodiments, sequences A and B are chemically synthesized on the same oligonucleotide; in some embodiments the first linear polynucleotide is made using an oligonucleotide comprising sequences A and B as a primer in the polymerase chain reaction (FIG. 4B).

In some embodiments the first linear polynucleotide comprises first and second restriction sites at or near its ends to facilitate digestion and ligation to circularize the polynucleotide. In some embodiments the first and second restriction sites are sites recognized by type IIs enzymes, in some embodiments the first and second restriction sites are either BsaI or BbsI or SapI or BspQI or Bst6I or EarI, Eam1104I or Ksp632I or LguI or PciSI, in some embodiments the first and second restriction enzymes are the same, in some embodiments the first and second restriction enzymes are different. In some embodiments the first linear polynucleotide is digested by a restriction enzyme and circularized with a DNA ligase, in some embodiments the first linear polynucleotide is circularized by a DNA ligase without restriction digestion. In some embodiments, the first linear polynucleotide is circularized by ligation independent methods or recombination based methods. In some embodiments, the first and second ends of the first linear polynucleotide are overlapping ends.

In some embodiments the first circular polynucleotide comprises a third restriction site that is different from the first and second restriction sites, and digestion with a third restriction enzyme linearizes the first circular polynucleotide to the second linear polynucleotide. In some embodiments the first circular polynucleotide comprises a third and fourth restriction site that are different from the first and second restriction sites, and digestion with a third and fourth restriction enzyme linearizes the first circular polynucleotide to the second linear polynucleotide, in some embodiments the third and fourth restriction enzymes are the same, in some embodiments the third and fourth restriction enzymes are different.

In some embodiments the first circular polynucleotide is amplified using the polymerase chain reaction to produce the second linear polynucleotide.

The advantage of such a procedure may be exemplified by considering that in some embodiments sequence elements A and B are short gRNA targeting sequences, C is a chimeric portion of a gRNA, D is a transcriptional terminator and E is a polIII promoter. Cloning the second linear polynucleotide, but not the first linear polynucleotide, into a vector between a second pol III promoter and a second chimeric portion of a gRNA plus transcriptional terminator results in a construct capable of expressing two gRNAs.

One method comprises primers designed to have blunt ends or restriction sites (for example, six cutters, type II cutters and the like). In preferred embodiments, primers are designed to comprise a first restriction site at the first 5' end of the forward primer and a second restriction site at the second 3' end of the reverse primer. In addition, the reverse primer comprises the two linked gRNAs separated by a sequence with third and fourth restriction sites (for example, six cutters, type II cutters and the like) that are different from the first and second restriction sites, and that create compatible overhangs with the ends of the genome modifying vector expressing Cas9, Cas9n, dCas9, in some embodiments the vector does not express Cas9. Multiple reverse primers comprising different linked pairs of gRNAs are used along with the forward primers to amplify off a template comprising a scaffold RNA sequence for the first gRNA, terminator and a RNA pol III promoter (FIG. 5A). PCR Amplification gives a population of first polynucleotide fragments with a first end, a scaffold RNA sequence, terminator, RNA pol III promoter, associated gRNAs separated by a sequence fragment comprising third and fourth restriction sites, followed by the second end that is compatible to the first end. In preferred embodiments, type IIs enzyme BsaI is used to create compatible four base pair overhangs at the first and second ends. A ligation step creates first circular polynucleotide by ligation of the first and second ends (FIG. 5B). A second restriction digest with a second restriction enzyme linearizes the first circular polynucleotide by cleavage within the sequence region between the two linked gRNAs to form a second polynucleotide with third and fourth ends that are compatible to the ends of linearized genome modifying vector expressing Cas9 (FIG. 5C). In preferred embodiments, type IIs enzyme SapI is used to generate third and fourth ends or overhangs. A library of polynucleotides so constructed is cloned into a genome modifying vector expressing Cas9 to create a library of genome modifying constructs or second circular polynucleotide pool comprising distinct pairs of linked gRNAs that are operably linked to two RNA pol III promoters for genome modification. In preferred embodiments the cloning is performed in a single reaction comprising restriction endonuclease and DNA ligase. In some embodiments the cas9 gene encodes a cas9 nickase or dCas9. In some embodiments, the genome modifying vector does not encode Cas9. In some embodiments, each of the gRNAs in the linked pair is directed to different functionally linked genomic loci of interest. In other embodiments, each of the gRNAs in the linked pair is directed to the same genomic locus. Other embodiments using different type IIs enzymes or other restriction enzymes are expressly contemplated.

In other embodiments, a library of any desired polynucleotide sequences that need to be coupled can be generated using the method described herein above comprising two or more respective linked sub-sequences, wherein the linkage of the sub-sequences is pre-determined. In some embodiments, the linked polynucleotide sequences are transcription units. Other embodiments using different type IIs enzymes or other restriction enzymes are expressly contemplated.

A kit comprising a library of linked gRNAs as described herein and reagents' including buffers, restriction endonucleases is another embodiment. In some embodiments, the kit comprises a template sequence, a primer, restriction endonucleases, buffers and instructions for design of oligonucleotides with two or more linked gRNAs and instructions for generating a library comprising two or more linked gRNAs.

DETAILED DESCRIPTION OF THE INVENTION

Definitions

Figure 1A:
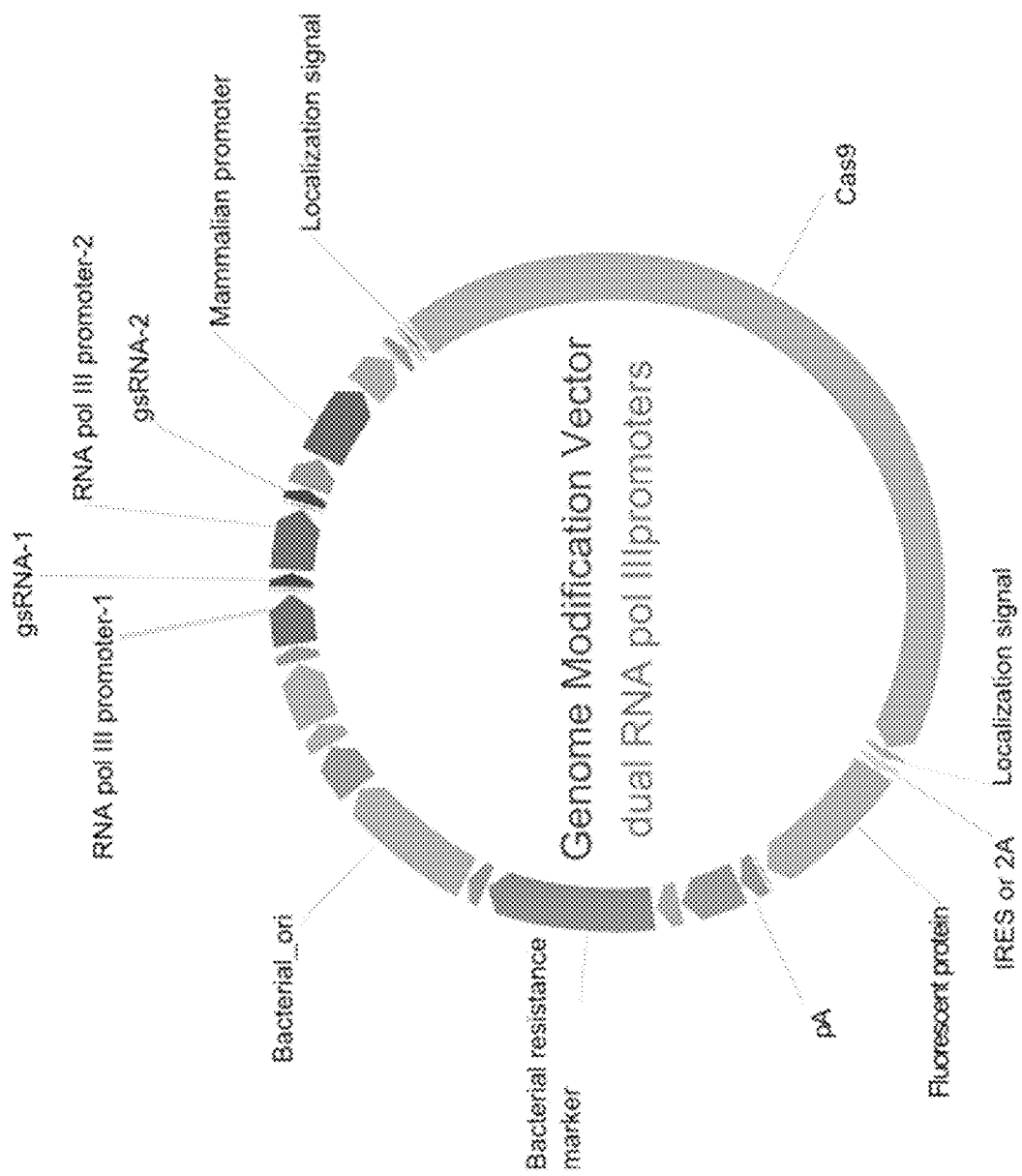
FIG. 1A: shows a plasmid map of a genome modifying construct with two RNA pol III promoters positioned to direct expression of two gsRNA molecules from adjacent expression cassettes in the same direction. Additionally a mammalian promoter directs expression of Cas9N (nickase), Cas9 wt (wild type) or dCas9 coupled to a reporter fluorescent protein via an IRES or 2A/CHYSEL element. The plasmid also comprises a bacterial origin of replication and a bacterial antibiotic resistance gene, shown. Similarly, other embodiments with three or more RNA pol III promoters directing expression of three or more gsRNA molecules from expression cassettes placed in tandem in the same or opposite directions is within the scope of this invention.

Use of the singular forms "a," "an," and "the" include plural references unless the context clearly dictates otherwise. Thus, for example, reference to "a polynucleotide" includes a plurality of polynucleotides, reference to "a substrate" includes a plurality of such substrates, reference to "a variant" includes a plurality of variants, and the like.

Terms such as "connected," "attached," "linked," and "conjugated" are used interchangeably herein and encompass direct as well as indirect connection, attachment, linkage or conjugation unless the context clearly dictates otherwise. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also within the scope of the invention. Where a combination is disclosed, each subcombination of the elements of that combination is also specifically disclosed and is within the scope of the invention. Conversely, where different elements or groups of elements are individually disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Unless defined otherwise herein, all technical and scientific terms used herein have the same meaning as commonly understood by one of ordinary skill in the art to which this invention belongs. Singleton, et al., *Dictionary of Microbiology and Molecular Biology*, 2nd Ed., John Wiley and Sons, New York (1994), and Hale & Marham, *The Harper Collins Dictionary of Biology*, Harper Perennial, NY, 1991, provide one of skill with a general dictionary of many of the terms used in this invention. Although any methods and materials similar or equivalent to those described herein can be used in the practice or testing of the present invention, the preferred methods and materials are described.

Unless otherwise indicated, nucleic acids are written left to right in 5' to 3' orientation; amino acid sequences are written left to right in amino to carboxy orientation, respectively.

The terms defined immediately below are more fully defined by reference to the specification as a whole.

The terms "polynucleotide," "oligonucleotide," "nucleic acid" and "nucleic acid molecule" and "gene" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, siRNA and mRNA, whether spliced or unspliced, any other type of polynucleotide which is an N- or C-glycoside of a purine or pyrimidine base, and other polymers containing nonnucleotidic backbones, for example, polyamide (for example, peptide nucleic acids ("PNAs")) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms are used interchangeably herein. These terms refer only to the primary structure of the molecule. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, and hybrids thereof including for example hybrids between DNA and RNA or between PNAs and DNA or RNA, and also include known types of modifications, for example, labels, alkylation, "caps," substitution of one or more of the nucleotides with an analog, internucleotide modifications such as, for example, those with uncharged linkages (for example, methyl phosphonates, phosphotriesters, phosphoramidates, carbamates, or the like) with negatively charged linkages (for example, phosphorothioates, phosphorodithioates, or the like), and with positively charged linkages (for example, aminoalkylphosphoramidates, aminoalkylphosphotriesters), those containing pendant moieties, such as, for example, proteins (including enzymes (for example, nucleases), toxins, antibodies, signal peptides, poly-L-lysine, or the like), those with intercalators (for example, acridine, psoralen, or the like), those containing chelates (of, for example, metals, radioactive metals, boron, oxidative metals, or the like), those containing alkylators, those with modified linkages (for example, alpha anomeric nucleic acids, or the like), as well as unmodified forms of the polynucleotide or oligonucleotide.

The terms "polynucleotide," "oligonucleotide," "nucleic acid" and "nucleic acid molecule" and "gene" refer to the entire sequence or gene or a fragment thereof. The fragment thereof can be a functional fragment. Where the polynucleotides are to be used to express encoded proteins, nucleotides that can perform that function or which can be modified (for example, reverse transcribed) to perform that function are used. Where the polynucleotides are to be used in a scheme that requires that a complementary strand be formed to a given polynucleotide, nucleotides are used which permit such formation.

The terms "nucleoside" and "nucleotide" include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, for example, where one or more of the hydroxyl groups are replaced with halogen, aliphatic groups, or is functionalized as ethers, amines, or the like. The term "nucleotidic unit" is intended to encompass nucleosides and nucleotides.

Standard A-T and G-C base pairs form under conditions which allow the formation of hydrogen bonds between the N3-H and C4-oxy of thymidine and the NI and C6-NH2, respectively, of adenosine and between the C2-oxy, N3 and C4-NH2, of cytidine and the $C2-NH_2$, N'—H and C6-oxy, respectively, of guanosine. Thus, for example, guanosine (2-amino-6-oxy-9-.beta.-D-ribofuranosyl-purine) may be modified to form isoguanosine (2-oxy-6-amino-9-.beta.-D-ribofuranosyl-purine). Such modification results in a nucleoside base which no longer effectively form a standard base pair with cytosine. However, modification of cytosine (1-.beta.-D-ribofuranosyl-2-oxy-4-amino-pyrimidine) to form isocytosine (1-.beta.-D-ribofuranosyl-2-amino-4-oxy-pyrimidine-) results in a modified nucleotide which does not effectively base pair with guanosine but forms a base pair with isoguanosine (U.S. Pat. No. 5,681,702 to Collins et al., hereby incorporated by reference in its entirety). Isocytosine is available from Sigma Chemical Co. (St. Louis, Mo.); isocytidine may be prepared by the method described by Switzer et al. (1993) Biochemistry 32:10489-10496 and references cited therein; 2'-deoxy-5-methyl-isocytidine may be prepared by the method of Tor et al., 1993, J. Am. Chem. Soc. 115:4461-4467 and references cited therein; and isoguanine nucleotides may be prepared using the method described by Switzer et al., 1993, supra, and Mantsch et al., 1993, Biochem. 14:5593-5601, or by the method described in U.S. Pat. No. 5,780,610 to Collins et al., each of which is hereby incorporated by reference in its entirety. Other non-natural base pairs may be synthesized by the method described in Piccirilli et al., 1990, Nature 343:33-37, hereby incorporated by reference in it entirety, for the synthesis of 2,6-diaminopyrimidine and its complement (1-methylpyra-zolo-[4,3]pyrimidine-5,7-(4H,6H)-dione. Other such modified nucleotidic units which form unique base pairs are known, such as those described in Leach et al. (1992) J. Am. Chem. Soc. 114:3675-3683 and Switzer et al., supra.

The phrase "DNA sequence" refers to a contiguous nucleic acid sequence. The sequence can be either single stranded or double stranded, DNA or RNA, but double stranded DNA sequences are preferable. The sequence can be an oligonucleotide of 6 to 20 nucleotides in length to a full length genomic sequence of thousands or hundreds of thousands of base pairs.

Host: is any prokaryotic or eukaryotic organism that can be a recipient of a nucleic acid. A "host," as the term is used herein, includes prokaryotic or eukaryotic organisms that can be genetically engineered. For examples of such hosts, see Maniatis et al., Molecular Cloning. A Laboratory Manual, Cold Spring Harbor Laboratory, Cold Spring Harbor, N.Y. (1982). As used herein, the terms "host," "host cell," "host system" and "expression host" can be used interchangeably.

When two elements are operably linked, they are in a functional relationship with one another. Functional linkage between a nucleic acid expression control sequence (such as a promoter, signal sequence, enhancer or array of transcription factor binding sites) and a second nucleic acid sequence means the expression control sequence affects transcription and/or translation of the nucleic acid corresponding to the second sequence when the appropriate molecules (for example, transcriptional activator proteins) are bound to the expression control sequence. The expression constructs of the invention comprising two or more RNA polymerase III promoters may comprise a nucleic acid sequence encoding an shRNA, dsRNA hairpin or microRNA operably linked to one, two, or to each of the promoters, or in one aspect the invention relates to an expression construct comprising two, three, four, five, or multiple RNA polymerase III promoter expression cassettes, designed for convenient insertion into each expression cassette of a selected sequence to be transcribed, for example, using appropriately selected cloning site(s), for example, comprising selected restriction sites. A guide RNA is operable linked to a scaffold RNA when the DNA segments encoding the two elements are adjacent to one other, such that the guide and scaffold RNAs are expressed as single contiguous RNA.

The term "Vector" or "DNA Vector" refers to a DNA sequence that is used to perform a "carrying" function for another polynucleotide. For example vectors are often used to allow a polynucleotide to be propagated within a living cell.

By "expression construct" is meant any double-stranded DNA or double-stranded RNA designed to transcribe an RNA of interest, for example, a construct that contains at least one promoter which is or may be operably linked to a downstream gene, coding region, or polynucleotide sequence of interest (for example, a cDNA or genomic DNA fragment that encodes a polypeptide or protein, or an RNA effector molecule, for example, an antisense RNA, triplex-forming RNA, ribozyme, an artificially selected high affinity RNA ligand (aptamer), a double-stranded RNA, for example, an RNA molecule comprising a stem-loop or hairpin dsRNA, or a bi-finger or multi-finger dsRNA or a microRNA, or any RNA of interest). An "expression construct" includes a double-stranded DNA or RNA comprising one or more promoters, wherein one or more of the promoters is not in fact operably linked to a polynucleotide sequence to be transcribed, but instead is designed for efficient insertion of an operably-linked polynucleotide sequence to be transcribed by the promoter. Transfection or transformation of the expression construct into a recipient cell allows the cell to express an RNA effector molecule, polypeptide, or protein encoded by the expression construct. An expression construct may be a genetically engineered plasmid, virus, recombinant virus, or an artificial chromosome derived from, for example, a bacteriophage, adenovirus, adeno-associated virus, retrovirus, lentivirus, poxvirus, or herpesvirus, or further embodiments described under "expression vector" below. An expression construct can be replicated in a living cell, or it can be made synthetically. For purposes of this application, the terms "expression construct", "expression vector", "vector", and "plasmid" are used interchangeably to demonstrate the application of the invention in a general, illustrative sense, and are not intended to limit the invention to a particular type of expression construct.

By "expression vector" is meant a DNA construct that contains at least one promoter which is or may be operably linked to a downstream gene, coding region, or polynucleotide sequence to be transcribed (for example, a cDNA or genomic DNA fragment that encodes a protein, optionally, operably linked to sequence lying outside a coding region, an antisense RNA coding region, or RNA sequences lying outside a coding region). An "expression construct" may also be a DNA construct comprising one or more promoters, wherein one or more of the promoters is not in fact operably linked to a polynucleotide sequence to be transcribed, but instead is designed for efficient insertion of an operably-linked polynucleotide sequence to be transcribed by the promoter. Transfection or transformation of the expression vector into a recipient cell allows the cell to express RNA encoded by the expression vector. An expression vector may be a genetically engineered plasmid, virus, or artificial chromosome derived from, for example, a bacteriophage, adenovirus, adeno-associated virus, retrovirus, poxvirus, or herpesvirus. Such expression vectors can include sequences from bacteria, viruses or phages. Such vectors include chromosomal, episomal and virus-derived vectors, for example, vectors derived from bacterial plasmids, bacteriophages, yeast episomes, yeast chromosomal elements, and viruses, vectors derived from combinations thereof, such as those derived from plasmid and bacteriophage genetic elements, cosmids and phagemids. Thus, one exemplary vector is a double-stranded DNA phage vector. Another exemplary vector is a double-stranded DNA viral vector. In one aspect, the invention relates to expression vectors, plasmids, and constructs as described herein, which are isolated and purified so as to be useful for any of a variety of applications, for example, as a reagent for scientific research, for human and/or veterinary use for therapeutic and/or prophylactic pharmaceutical purposes.

The term "Scar" refers to extra DNA sequences that are left as part of a polynucleotide construct that are an unavoidable consequence of the construction method rather than being incorporated because of their desirable functional properties. For example recombinases, integrases and restriction endonucleases often have recognition sequences that remain within the sequence of a polynucleotide that is constructed using the action of the recombinases, integrases and restriction endonucleases. The term "Scar Size" refers to the length of the extra DNA sequences. For example a scar size of 34 base pairs is left in a construct with a recognition sequence for Cre recombinase, a scar size of 25 base pairs is added on when attB integrase is used. Scars can interfere with the functions of other sequence elements within the construct.

Overhang or DNA Overhang refers to the single-stranded portion at the end of a double-stranded DNA molecule. Compatible overhangs are those which are mutually complementary (i.e., base-pair with each other) with sufficient stability to permit ligation of nucleic acids being the compatible end.

The term "Selectable marker" refers to a DNA segment that allows one to select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions. Examples of Selectable markers include but are not limited to: (1) DNA segments that encode products which provide resistance against otherwise toxic compounds (e.g., antibiotics); (2) DNA segments that encode products which are otherwise lacking in the recipient cell (e.g., tRNA genes, auxotrophic markers); (3) DNA segments that encode products which suppress the activity of a gene product; (4) DNA segments that encode products which can be readily identified (e.g., phenotypic markers such as beta-galactosidase, green fluorescent protein (GFP), and cell surface proteins); (5) DNA segments that bind products which are otherwise detrimental to cell survival and/or function; (6) DNA segments that otherwise inhibit the activity of any of the DNA segments described in Nos. 1-5 above (e.g., antisense oligonucleotides); (7) DNA segments that bind products that modify a substrate (e.g. restriction endonucleases); (8) DNA segments that can be used to isolate a desired molecule (e.g. specific protein binding sites); (9) DNA segments that encode a specific nucleotide sequence which can be otherwise non-functional (e.g., for PCR amplification of subpopulations of molecules); and/or (10) DNA segments, which when absent, directly or indirectly confer sensitivity to particular compounds.

The term "Counter Selectable Marker" refers to a DNA sequence that confers a selective disadvantage upon a host cell. Examples of counter-selectable markers include sacB, rpsL, tetAR, pheS, thyA, gata-1, ccdB, kid and barnase (Bernard, 1995, Journal/Gene, 162: 159-160; Bernard et al., 1994. Journal/Gene, 148: 71-74; Gabant et al., 1997, Journal/Biotechniques, 23: 938-941; Gababt et al., 1998, Journal/Gene, 207: 87-92; Gababt et al., 2000, Journal/Biotechniques, 28: 784-788; Galvao and de Lorenzo, 2005, Journal/Appl Environ Microbiol, 71: 883-892; Hartzog et al., 2005, Journal/Yeat, 22:789-798; Knipfer et al., 1997, Journal/Plasmid, 37: 129-140; Reyrat et al., 1998, Journal/Infect Immun, 66: 4011-4017; Soderholm et al., 2001, Journal/Biotechniques, 31: 306-310, 312; Tamura et al., 2005, Journal/Appl Environ Microbiol, 71: 587-590; Yazynin et al., 1999, Journal/FEBS Lett, 452: 351-354). Counter-selectable markers often confer their selective disadvantage in specific contexts. For example they may confer sensitivity to compounds that can be added to the environment of the host cell, or they may kill a host with one genotype but not kill a host with a different genotype. Conditions which do not confer a selective disadvantage upon a cell carrying a counter-selectable marker are described as "permissive". Conditions which do confer a selective disadvantage upon a cell carrying a counter-selectable marker are described as "restrictive".

The term "Recognition sequence" refers to particular DNA sequences which are recognized (and bound by) a protein, DNA, or RNA molecule, including a restriction endonuclease, a modification methylase, and a recombinase. For example, the recognition sequence for Cre recombinase is loxP which is a 34 base pair sequence comprised of two 13 base pair inverted repeats (serving as the recombinase binding sites) flanking an 8 base pair core sequence. See FIG. 1 of Sauer, B., Current Opinion in Biotechnology 5:521-527 (1994). Other examples of recognition sequences are the attB, attP, attL, and attR sequences which are recognized by the integrase of bacteriophage lambda. AttB is an approximately 25 base pair sequence containing two 9 base pair core-type Int binding sites and a 7 base pair overlap region. attP is an approximately 240 base pair sequence containing core-type Int binding sites and arm-type Int binding sites as well as sites for auxiliary proteins IHF, FIS, and Xis. See Landy, Current Opinion in Biotechnology 3:699-707 (1993). Such sites are also engineered according to the present invention to enhance methods and products.

The term "Recombinase" refers to an enzyme which catalyzes the exchange of DNA segments at specific recombination sites.

The term "Recombinational Cloning" refers to a method described herein, whereby segments of DNA molecules are exchanged, inserted, replaced, substituted or modified, in vitro or in vivo.

The term "Recombination proteins" includes excisive or integrative proteins, enzymes, co-factors or associated proteins that are involved in recombination reactions involving one or more recombination sites. See, Landy (1994), infra.

The term "expression system" refers to any in vivo or in vitro biological system that is used to produce one or more polypeptide encoded by a polynucleotide.

The term "annealing temperature" or "melting temperature" or "transition temperature" refers to the temperature at which a pair of nucleic acids is in a state intermediate between being fully annealed and fully melted. The term refers to the behavior of a population of nucleic acids: the "annealing temperature" or "melting temperature" or "transition temperature" is the temperature at which 50% of the molecules are annealed and 50% are separate. Annealing temperatures can be determined experimentally. There are also methods well known in the art for calculating these temperatures.

The term "translation" refers to the process by which a polypeptide is synthesized by a ribosome 'reading' the sequence of a polynucleotide.

The term "selectable protein" refers to a protein that provides a physical, chemical or biological method for selecting cells on the basis of how much of the selectable protein is expressed.

The term "coupling element" refers to a DNA sequence that allows the expression of a first polypeptide to be linked to the expression of a second polypeptide. Internal ribosome binding sites and cis-acting hydrolase elements are examples of coupling elements.

The phrase "predetermined time period" refers to a specified amount of time. A "predetermined period of time" can be on the order of seconds, minutes, hours, days, weeks, or months. For example, a "predetermined time period" can be between 1 and 59 minutes, or any increment between 1 and 2 hours, or any increment between 2 and 4 hours, or any increment between 4 and 6 hours, or any increment between 6 and 12 hours, or any increment between 12 and 24 hours, or any increment between 1 day and 2 days, or any increment between 2 days and 4 days, and any increment between 4 days and 7 days, and any increment between 1 week and 4 weeks, and any increment between 1 month and 12 months, or any combination of incremental time periods therein.

The term "type IIs restriction enzyme" is refers to any restriction enzyme that cleaves DNA at a defined distance outside its recognition sequence, and whose recognition sequence is non-palindromic.

The terms "ligatable ends" or "compatible ends" describe two ends of polynucleotide molecules that are both blunt or that both possess overhangs of the same length and directionality (ie both are 5'-overhangs, or both are 3'-overhangs) and with perfectly complementary sequences, such that the DNA ends form standard Watson-Crick base pairs (ie C with G and T or U with A) and can be joined by a DNA ligase.

The term "Daughter Vector" describes a polynucleotide comprising a first type IIs restriction site and a second type IIs restriction site, wherein cleavage of the Daughter Vector with the first and second type IIs restriction enzymes produces a first polynucleotide vector fragment, referred to herein as a "Daughter Vector Fragment", which comprises a selectable marker but lacks the first and second type IIs restriction sites, and a second polynucleotide fragment, referred to herein as a "Stuffer Fragment".

The term "Daughter Vector Fragment" describes a polynucleotide fragment produced by restriction digestion of a polynucleotide with one or more type IIs restriction enzymes, such that the Daughter Vector Fragment comprises a selectable marker but lacks recognition sites for the one or more type IIs restriction enzymes.

In the expression constructs or vectors of the invention, the RNA polymerase III promoters are "isolated" in the sense that they are not operably linked to a gene or RNA sequence with which they are operably linked in their normal cellular environment, for example, in the expression constructs of the invention the 7SK promoter is not operably linked to the 7SK gene, the U6 promoter is not operably linked to the U6 gene, and the H1 promoter is not operably linked to the H1 gene, or the like.

A genome modifying vector means a vector adapted for modification of a genome, such as by expression of a nuclease (e.g., Cas9) encoded by the vector, which nicks or cleaves the genome, or by inclusion of an insert flanked by homology arms that can undergo recombination with a genome, or both. The genome modifying vector can be an expression vector containing a promoter operably linked for expression of an insert nucleic acid. The insert nucleic acid can be gsRNA or a nucleic acid fragment to be inserted into the genome, or both A genome modifying vector including such an insert can also be referred as genome modifying construct.

An RNA-guided nuclease is a nuclease that recognizes a duplex of a guide RNA and one strand of a DNA molecule to be cleaved. Cleavage can be a double-stranded blunt ended, double-stranded staggered ends, or single-stranded as described further below. Cleavage is within the strand of the DNA molecule duplexed with the guide RNA or corresponding region of the complementary strand. The segment of the DNA molecule being cleaved that duplexes with a guide RNA is referred to as a target site. RNA guided nuclease typically have two activate sites, one for the strand of DNA molecule bound to the guide RNA, the other for the opposing strand. RNA-guided nucleases are also referred to as Cas enzymes for CRISPR-associated nuclease. Examples of Cas enzymes include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4, By "Cas9" is meant a nuclease, an enzyme specialized for cutting DNA, with two active sites, one for each strand of the double helix. Cas9 can function as a programmable RNA-guided endonuclease in heterologous organisms. Cas9 belongs to the best studied type II bacterial CRISPR/Cas system of *Streptococcus pyogenes* or *Streptococcus pneumoniae*, and is thought to be the sole protein responsible for small interfering CRISPR RNA (crRNA)-guided silencing of foreign DNA. An exemplary Cas9 amino acid sequence, that of *S. pyogenes* Cas9 protein, may be found in the SwissProt database under accession number Q99ZW2. Amino acids are numbered by this sequence are other sequence maximally with this sequence. Cas9 includes this sequence, naturally occurring variants in the same species, and species variants. Cas9 also includes induced variants having at least 90, 95, or 99% sequence identity with the exemplary sequence, and having cleaving, gene silencing or nicking activity. Sequence identity refers to two or more sequences having a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100).

In some embodiments, enzyme coding sequence encoding a CRISPR enzyme is codon optimized for expression in particular host cells, for example eukaryotic cells. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a CRISPR enzyme correspond to the most frequently used codon for a particular amino acid. CRISPR loci have been identified in more than 40 prokaryotes (See e.g., Jansen et al., Mol. Microbiol., 43:15654575 [2002]; and Mojica et al., [2005]) including, but not limited to *Aeropyrum, Pyrobaculum, Sulfolobus, Archaeoglobus, Halocarcula, Methanobacteriumn, Methanococcus, Methanosarcina, Methanopyrus, Pyrococcus, Picrophilus, Thernioplasnia, Corynebacterium, Mycobacterium, Streptomyces, Aquifrx, Porphvromonas, Chlorobium, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Myrococcus, Campylobacter, Wolinella, Acinetobacter, Erwinia, Escherichia, Legionella, Methylococcus, Pasteurella, Photobacterium, Salmonella, Xanthomonas, Yersinia, Treponema*, and *Thermotoga*.

A guide RNA or gRNA or targeting RNA means a short RNA (e.g., 15-30 or 17-25 nucleotides) complementary to a segment of a strand of DNA molecule being targeted for cleavage by an RNA guided nuclease, such as Cas9. The guide RNA directs the RNA guided nuclease to cut DNA within the segment forming the duplex region or complementary segment of the other strand. The designation gRNA can indicate a gRNA by itself or linked to a scaffold RNA.

A scaffold RNA (sRNA, which in the case of Cas9 is also known as a Cas9 binding hairpin or Cas9 handle, means a hairpin structure, which can bind to an RNA-guided nuclease such as Cas9. A scaffold RNA can have a length of for example, 15-80, 15-50, 15-40, 15-30 or 15-25 bases. Examples of sequences that can be included in scaffolds include SEQ ID NOs: 563-682 of US 20140068797. For brevity, a DNA molecule may be described as including a scaffold RNA sequence. This means the DNA molecule includes a DNA segment encoding the scaffold RNA.

A fusion of a guide RNA and a scaffold RNA can be referred to as a chimeric RNA or gsRNA. The guide RNA and scaffold RNA can be fused directly or via a short RNA linker (e.g, 3-10 bases). A short RNA linker can also be provided as an element of the scaffold (i.e., a stem).

Cas9 has two catalytic domains, the RuvC-like nuclease domain that cleaves the noncomplementary strand and the HNH nuclease domain that cleaves the complementary strand of DNA.

By "Cas9n or nickase" is meant a D10A point mutation in the RuvC-like nuclease domain of Cas9 nuclease or a point mutation H840A in the HNH nuclease domain (or other mutation, such as N854A and N863A having a similar effect. Other mutations may be useful; where the Cas9 or other CRISPR enzyme is from a species other than *S. pyogenes*, mutations in corresponding amino acids may be made to achieve similar effects. The Cas9n nicks single strands and combined with a pair of offset guide RNAs complementary to opposite strands of target genomic loci helps reduce off-target activity seen with wild type Cas9. Nicking of both DNA strands by a pair of Cas9 nickases leads to site-specific double stand breaks (DSBs) and NHEJ (non-homologous end joining). As a further example, two or more catalytic domains of Cas9 (RuvC I, RuvC II, and RuvC III) may be mutated to produce a mutated Cas9 substantially lacking all DNA cleavage activity. In some embodiments, a D10A mutation is combined with one or more of H840A, N854A, or N86:3A mutations to produce a Cas9 enzyme substantially lacking all DNA cleavage activity. In some embodiments, a CRISP enzyme is considered to substantially lack all DNA cleavage activity when the DNA cleavage activity of the mutated enzyme is less than about 25%, 10%, 5%, 1%, 0.1%, 0.01%, or lower with respect to its non-mutated form.

By "dCas9" is meant an inactive Cas9 nuclease that has point mutations in both the RuvC-like (D10A) and HNH (H840A) nuclease domains In *Escherichia coli* dCas9, when coexpressed with a gRNA designed with a 20-bp complementary region to any gene of interest, can efficiently silence a target gene with up to 99.9% repression.

By a "promoter" is meant a nucleic acid sequence sufficient to direct transcription of an operably linked nucleic acid molecule. Promoters may act with transcription control elements (for example, enhancers) that are sufficient to render promoter-dependent gene expression controllable in a cell type-specific, tissue-specific, or temporal-specific manner, or that are inducible by external signals or agents; such elements, may be found in a 5' or 3' region of a gene or within an intron. See, for example, Published U.S. Patent Application No. 2005/0130184 A1, 16 Jun. 2005, Xu et al., directed to modified polymerase III promoters which utilize polymerase II enhancer elements, as well as Published U.S. Patent Application No. 2005/0130919 A1, 16 Jun. 2005, Xu et al., directed to regulatable polymerase III and polymerase II promoters, the teaching of which is hereby incorporated by reference. Desirably, a promoter is operably linked to a nucleic acid sequence, for example, a cDNA or a gene sequence, or an effector RNA coding sequence, in such a way as to enable expression of the nucleic acid sequence, or a promoter is provided in an expression cassette into which a selected nucleic acid sequence to be transcribed can be conveniently inserted.

By "RNA polymerase promoter" or "RNA pol promoter" or "polymerase promoter" or "pol promoter" is meant any promoter that interact in a selected host cell with an RNA polymerase to transcribe an operably linked nucleic acid sequence encoding a non-protein encoding RNA, such as a guide RNA, more particularly promoters that interact with RNA polymerase III in eukaryotes.

By "RNA polymerase III promoter" or "RNA pol III promoter" or "polymerase III promoter" or "pol III promoter" is meant any invertebrate, vertebrate, or mammalian promoter, for example, human, murine, porcine, bovine, primate, simian, or the like, that, in its native context in a cell, associates or interacts with RNA polymerase III to transcribe its operably linked gene, or any variant thereof, natural or engineered, that interact in a selected host cell with an RNA polymerase III to transcribe an operably linked nucleic acid sequence. By U6 promoter (for example, human U6, murine U6), H1 promoter, or 7SK promoter is meant any invertebrate, vertebrate, or mammalian promoter or polymorphic variant or mutant found in nature to interact with RNA polymerase III to transcribe its cognate RNA product, U6 RNA, H1 RNA, or 7SK RNA, respectively. Preferred in some applications are the Type III RNA pol III promoters including U6, H1, and 7SK which exist in the 5' flanking region, include TATA boxes, and lack internal promoter sequences. Internal promoters occur for the pol III 5S rRNA, tRNA or VA RNA genes. The 7SK RNA pol III gene contains a weak internal promoter and a sequence in the 5' flanking region of the gene necessary for transcription. RNA pol III promoters include any higher eukaryotic, including any vertebrate or mammalian, promoter containing any sequence variation or alteration, either natural or produced in the laboratory, which maintains or enhances but does not abolish the binding of RNA polymerase III to the promoter, and which is capable of transcribing a gene or nucleotide sequence, either natural or engineered, which is operably linked to the promoter sequence. Pol III promoters for utilization in an expression construct for a particular application, for example, to express RNA effector molecules such as gRNA or hairpin dsRNAs against a fish, bird, or invertebrate virus may advantageously be selected for optimal binding and transcription by the host cell RNA polymerase III, for example, including avian pol III promoters in an expression construct designed to transcribe a plurality of hairpin dsRNAs against an avian virus such as West Nile Virus or avian influenza virus (H.sub.5N1) in avian host cells and utilizing instead human or other mammalian pol III promoters in an expression construct designed to transcribe a plurality of hairpin dsRNAs against an avian virus such as West Nile Virus or avian influenza virus (H.sub.5N1) in human host cells.

By "prokaryotic promoter" is meant any prokaryotic RNA polymerase promoter, for example, bacteria including *E. coli, Bacillus, Pseudomonas*, viruses that infect prokaryotes or the like.

By "multiple polymerase III promoter vector" or "multiple pol III promoter expression construct" or similar expressions, is meant any vector, plasmid, or expression construct which contains at least two polymerase III promoters. In one aspect, the multiple polymerase III promoter vector contains at least two different polymerase III promoters. By "different" polymerase III promoters is meant any two RNA polymerase III promoters, including variants such as polymorphisms and mutants thereof, which in a particular species drives transcription of different cognate transcripts, such as, for example, the human 7SK promoter, the human U6 promoter, and the human H1 promoter, which are considered three "different" polymerase III promoters. Corresponding polymerase III promoters from different species, such as, for example, a human U6 vs. a murine U6 promoter are different promoters; a human H1 vs. a murine H1 promoter are different; or a human 7SK promoter and a murine 7SK promoter are different promoters. Therefore, the various U6 promoter sequences shown in SEQ ID NOS: 1-5 are considered variants of the "same" promoter, the U6 promoter. In some aspects, multiple copies of the "same" polymerase III promoter may be included in a genome modifying construct of the invention so long as two "different" RNA polymerase III promoters are also included; for example, three U6 promoters (for example, U6.1, two U6-8cc promoters) and one H1 promoter; or four 7SK promoters (7SK 256 promoter, three 7SK 4A promoters) and one U6 promoter. In some aspects, the genome modifying constructs of the invention may contain multiple copies of the same polymerase III promoter without a "different" polymerase III promoter; for example, three, four, five, six or more 7SK promoters each operably linked to a sequence encoding a gRNA. Optionally, in some embodiments, other promoters may be included in addition to the two or more polymerase III promoters, for example, one or more polymerase I promoters and/or one or more polymerase II promoters, one or more mitochondrial promoters, or the like. In one aspect, an genome modifying construct comprising multiple polymerase III promoters (2, 3, 4, 5, or more) is engineered to express multiple gRNAs, in which case 2, 3, 4, 5, or more copies of the same pol III promoter may be used, irrespective of whether or not a "different" RNA polymerase III promoter is also included.

The term "linked gRNAs" is used to identify gRNAs that are produced from the same DNA construct

DESCRIPTION

CRISPR/Cas9 for Genome Modification

Precise and efficient genome-engineering technologies, including the custom-made zinc-finger nucleases (ZFNs) and transcription activator-like effectors (TALENs), have been successfully applied in a variety of mammalian cells and model organisms, including fruit fly, zebrafish, frog, mouse, rat and pig. A large body of investigations demonstrates that gene-specific alterations, including insertions or deletions (indels), can be generated via non-homologous end-joining (NHEJ) induced by ZFN- or TALEN-mediated double-stranded breaks (DSBs) in many mammalian cells and all model organisms tested. If a double- or single-stranded DNA donor is provided, precise nucleotide substitutions or insertions of up to ~8.0 kb at or near the break site are achieved via homology-directed repair (HDR) in mammalian cells and in zebrafish embryos, suggesting the room for improvement in target-specific gene knockin and knockout in vivo. Precise insertion of a reporter gene or mutant loxP (mloxP) site is especially important for investigating endogenous gene expression or generating conditional gene knockouts in model organisms.

Recent advances in the study of prokaryotic clustered regularly interspaced short palindromic repeats (CRISPR) adaptive immune system provide an alternative genome editing approach. The CRISPR/CRISPR-associated (Cas) system protects bacteria and archaea from invading viruses and plasmids. Three major types of CRISPR have been categorized on the basis of locus organization and gene conservation. Cas9 belongs to the best studied type II bacterial CRISPR/Cas system of *Streptococcus pyogenes*, and is thought to be the sole protein responsible for small interfering CRISPR RNA (crRNA)-guided silencing of foreign DNA. A transactivating crRNA (tracrRNA) that is complementary to the repeat sequences in pre-crRNA is required for the silencing. Several studies have demonstrated that Cas9 guided by chimeric gsRNA that comprises the fusion of crRNA to tracrRNA is sufficient to execute in vitro sequence-specific cleavage of target DNA and site-specific DNA cleavage in mammalian cells as reported most recently. Cas9 can function as an RNA-guided endonuclease in heterologous organisms.

CRISPR systems offer an advantage to zinc finger and transcription activator-like effector DNA binding proteins, as the site specificity in nucleotide binding CRISPR-Cas proteins is governed by a RNA molecule instead of the DNA-binding protein, which can be more challenging to design and synthesize. To express RNA without modifications added by the RNA polymerase II transcription system, RNA polymerase III regulatory elements have been used for transcription of functional gRNA in human cells. Cas9 endonuclease from *Streptococcus pyogenes* type II CRISPR/Cas system can be programmed to produce sequence-specific double-strand breaks in vitro by providing a synthetic single RNA (gsRNA) comprising a fusion of gRNA and sRNA (Jinek et al., 2012). More intriguingly, Cas9 and gsRNA are the only components necessary and sufficient for induction of targeted DNA cleavage in cultured human cells (Cho et al., 2013; Cong et al., 2013; Mali et al., 2013) as well as in zebrafish (Chang et al., 2013; Hwang et al., 2013).

Recent studies of Cas9 specificity have shown that, although each base within the guide RNA contributes to overall specificity, multiple mismatches between the guide RNA and its complementary target DNA sequence can be tolerated, leading to potential off-target double strand breaks (DSBs) and indel formation. These unwanted mutations can potentially limit the utility of Cas9 for genome editing applications, especially ones requiring high levels of precision, for example generation of isogenic cell lines for testing causal genetic variations. A paired nickase strategy that combines the D10A mutant of Cas9 (Cas9n) with a pair of offset gRNAs complementary to the opposite strands of the target site helps ameliorate off-target activity. Nicking of both DNA strands by a pair of Cas9 nickases leads to site-specific double stand breaks (DSBs) and NHEJ (non-homologous end joining), individual nicks are predominantly repaired by the high fidelity base excision repair pathway (BER) (Dianov and Hubscher, 2013). In a manner analogous to dimeric zinc finger nucleases (ZFNs) and transcription-activator-like effector nucleases (TALENs) wherein DNA cleavage requires synergistic interaction of two independent specificity-encoding DNA-binding molecules directing FokI nuclease monomers, this double-nicking strategy using Cas9n minimizes off-target mutagenesis by each individual Cas9n-gRNA complex while maintaining on-target modification rates similar to those of wild-type Cas9.

The CRISPR system can be repurposed as a new RNA-guided DNA-binding platform to repress the transcription of any gene. This CRISPR interfering system, called the CRISPRi utilizes a catalytically inactive version of Cas9 (dCas9) that lacks endonucleolytic activity can also be used for transcriptional regulation. The dCas9 contains two point mutations in both its RuvC-like (D10A) and HNH nuclease (H840A) domains, and is deficient in nucleolytic activity in vitro (Jinek et al., 2012. Science 337, 816-821). In *Escherichia coli* dCas9, when coexpressed with a gRNA designed with a 20-bp complementary region to any gene of interest, can efficiently silence a target gene with up to 99.9% repression. When the gRNA targets the promoter region, it can sterically prevent the association between key cis-acting DNA motifs and their cognate trans-acting transcription factors, leading to repression of transcription initiation. The silencing is inducible and fully reversible and is highly specific in bacterial cells as measured by RNA-seq. Repression efficiencies can be tuned by introducing single or multiple mismatches into the gRNA base-pairing region or by targeting different loci along the target gene. Multiple gRNAs can be used simultaneously to regulate multiple genes, to synergistically control a single gene for enhanced repression or for tuning silencing to achieve a moderate level of gene repression. One embodiment of the present invention facilitates dCas9 mediated silencing directed by a pair of gRNAs in a single construct.

Expression of a single chimeric crRNA: tracrRNA transcript, which normally is expressed as two different RNAs in the native type II CRISPR system, is sufficient to direct the Cas9 nuclease to sequence-specifically cleave target DNA sequences. The single chimeric crRNA: tracrRNA transcript or its separate components have been expressed using RNA polymerase III (pol III) promoters. Variants of the U6 and H1 RNA pol III promoters have been developed to control expression of small RNAs.

The present vectors and methods are particularly useful in combination with a Cas9 nickase. Expression of the Cas9 nickase with two overlapping guide RNAs complementary to opposing strands of a target locus allows nicking of the strands at proximate but different sites resulting in a complete break of a double stranded target generating cohesive ends. The use of two guide RNAs increases specificity compared with use of a single guide RNA and a Cas9 with double stranded cleavage activity. The present vectors and methods can also be used with a Cas9 with double-stranded cleavage activity. In this case, two guide RNAs can be used to direct double stranded cleavages to two distinct locations within a genome. The present vectors and methods can also be used with dCas9 to repress transcription at two separate sites, e.g., in two genes within a genome.

Multiple RNA polymerase Promoter Expression Construct

A huge variety of vectors, expression constructs, and expression systems including circular plasmids, linearized plasmids, cosmids, viral genomes, recombinant viral genomes, artificial chromosomes have been developed for use in prokaryotes and/or eukaryotes. Among the tremendous variety of expression vectors and expression systems that have been developed in the field of biotechnology and molecular biology are expression systems containing multiple promoters on the same vector. One such type of multiple promoter expression system utilizes vectors containing multiple promoters (two or more promoters) that are active in a prokaryote or in the same subcellular compartment of a eukaryotic cell. For example, such multiple promoter systems in the art have been developed to permit expression of more than one sequence in the same compartment of the same cell (for example, two distinct sequences or a sense and antisense sequence designed to form a dsRNA), or they may be used to express the same sequence within different cells or organisms (example, a prokaryote and a eukaryote) or to obtain more efficient transcription of a single operably linked sequence. Frequently seen are, for example, multiple RNA polymerase II promoters or bacteriophage promoters on the same plasmid, such as, for example, two polymerase II promoters-such as CMV and SV40, or a bacteriophage T7 promoter and a bacteriophage SP6 promoter.

Further, such multiple promoters can be arranged within the vector in any number of orientations and configurations. For example, two promoters can direct transcription both, from the same or from the opposite strands of the vector. If oriented on the same strand, they drive transcription in the same direction within the vector. Alternatively, multiple promoters may be encoded on opposite strands and arranged either convergently or divergently with respect to each other in the same vector, in which case, transcription proceeds in opposite directions within the vector. Further, a variety of terms have been developed in the art to describe the relative position of multiple promoters within a single vector. The term "tandem" has been used to describe multiple promoters that all reside on, and are all operably linked to, the 5' end of the sequence to be transcribed. Tandem promoters can be the same or different promoters. The term "flanking" promoters describes the orientation of multiple promoters in which the sequence to be transcribed is flanked on both the 5' and the 3' end by a promoter in such a manner that each promoter, when transcriptionally active, is capable of transcribing one strand of the sequence to be transcribed. The flanking promoters can be the same or different promoters. Example, a set of bacteriophage T7 RNA polymerase promoters flanking the 5' and 3' ends of a sequence is a common method for expressing separate sense and antisense strands to form duplex dsRNA (WO99/32619, Fire et al., published Jul. 1, 1999).

Multiple tandem promoters are described, for example, in U.S. Pat. No. 5,547,862, which discloses a DNA vector which comprises an RNA transcription sequence positioned downstream from two or more tandem promoters which are recognized by distinct RNA polymerases and are each capable of promoting expression of the RNA transcription sequence.

A method for making mammalian collagen or procollagen in yeast is disclosed in U.S. Pat. No. 6,472,171 using a construct comprising, in opposite orientations, two mammalian collagen genes operably linked to a single or dual, divergent heterologous promoter(s). The promoter(s) driving the two collagen genes may be the same promoter, or different promoters, and may be used to provide for the coordinate, preferably simultaneous, expression of the two collagen genes.

Expression vectors containing dual bacterial promoters arranged in tandem and operably linked to a heterologous nucleic acid encoding a desired polypeptide are disclosed in U.S. Pat. No. 6,117,651. The dual promoter comprises a first component derived from a tac-related promoter (which is itself a combination of the lac and trp promoters) and a second promoter component obtained from a bacterial gene or operon that encodes an enzyme involved in galactose metabolism. The dual bacterial promoter system acts synergistically to provide a high level of transcription of the linked sequence in a prokaryotic cell such as E. coli.

U.S. Pat. No. 5,874,242 discloses a vector which provides for the translation of an inserted coding sequence in both eukaryotic and prokaryotic host cells. Specifically, such vectors include either a bifunctional promoter (functional in both eukaryotes and prokaryotes) or dual promoters (promoters separately functional in eukaryotes and prokaryotes) for efficient expression in both prokaryotic and eukaryotic cells.

It is well-established that vector-directed expression of short RNA effector molecules including short hairpin dsRNAs is most efficient when under the control of one of the mammalian promoter types which the cell naturally employs for expression of normally occurring small RNA molecules. These promoters typically comprise the family of RNA Polymerase III promoters. There are further defined in the literature as three main subclasses of RNA polymerase III promoters, Type 1, Type 2 and Type 3. Prototypical examples of promoters in each class are found in genes encoding 5s RNA (Type 1), various transfer RNAs (Type 2) and U6 small nuclear RNA (Type 3). Another promoter family (transcribed by RNA Polymerase I) is also dedicated in the cell to transcription of small structural RNAs; however, this family appears to be less diverse in sequence than the RNA Polymerase III promoters. Finally, RNA Polymerase II promoters are used in the transcription of the protein-coding messenger RNA molecules, as distinguished from the small structural and regulatory RNA mentioned above. The majority of promoter systems known in the art utilize RNA Polymerase II promoters, which are not optimal for production of small RNAs.

RNA polymerase III promoter-based vectors containing one promoter have been described in the art (see, example, U.S. Pat. No. 5,624,803, Noonberg et al., "In vivo oligonucleotide generator, and methods of testing the binding affinity of triplex forming oligonucleotides derived therefrom"), and a description of U6-based vector systems can be found in Lee et al., Nat. Biotechnol. 20:500-05 (2002). Yu et al., Proc. Natl. Acad. Sci. USA 99:6047-52 (2002), describe an expression system for short duplex siRNAs comprising a T7 and U6 promoter. Miyagishi and Taira, Nat. Biotechnol. 20:497-500 (2002), describe expression plasmids for short duplex siRNAs comprising expression cassettes containing tandem U6 promoters, each transcribing either the sense or the antisense strand of an siRNA, which are then annealed to form duplex siRNAs. Also described are expression plasmids including two such U6 based siRNA expression cassettes.

To express RNA without modifications added by the RNA polymerase II transcription system, RNA polymerase III regulatory elements have been used for transcription of functional gRNA in human cells. The single chimeric crRNA:tracrRNA transcript along with the gRNA has been expressed using RNA polymerase III (pol III) promoters. The most abundant cellular RNAs transcribed from a type III RNA pol III promoter are the U6 small nuclear RNA which play a crucial role in the processing of premature RNA; the 7SK RNA, a negative regulator of RNA polymerase II elongation factor TEFb; and H1 RNA, a component of RNAse P. Variants of the U6 and H1 RNA pol III promoters have been developed to control expression of small RNAs, for example synthesis of siRNA and shRNA in cells are often driven by RNA polymerase III (pol III) promoters. There are several advantages to using RNA pol III systems. siRNA transcription is high, and the fact that it is driven by cis-acting elements found exclusively in the 5'-flanking region, results in uniform RNA molecules containing defined 5' and 3' ends. Other pol III promoters that rely both on internal and upstream sequences for efficient expression include the silkworm tRNA$^{Ala}$, human 7SL, EBER RNAs and Xenopus tRNA$^{Sec}$ genes. The best characterized type III promoter belongs to the snRNAU6 genes including other transcription units such as the 7SK, Y and MRP RNA genes that have similar type III basal promoter elements. Several inducible promoter systems based on variants of the U6 and H1 RNA pol III promoters have been developed to control expression of small RNAs. The use of different strategies to make these promoters respond to external signals is expressly contemplated, for example the Cre-loxP system, the ecdysone-inducible system, the lac-repressor system and the tet-repressor system.

In the general practice and use of recombinant DNA and synthetic vectors for RNA expression in eukaryotic cells, the majority of engineering efforts have been directed towards expression of protein-coding RNA molecules. With the advent of antisense RNA and, more recently, the phenomenon of gene silencing by RNA interference (via double-stranded RNA, abbreviated "dsRNA") as well as guide RNA for genome modifications, expression systems suitable for generating short, non-protein encoding RNA molecules that are essentially catalytic in nature have been developed. This has required the adaptation of several classes of natural promoters that have evolved to generate natural, small RNA molecules (such as ribosomal RNAs, spliceosome RNAs, RNAse P structural RNA components et al.), and these promoters are generally classed as RNA Polymerase I and RNA Polymerase III ("Pol III") promoters. The RNA polymerase III promoters are admirably adapted to expression of such short RNA transcripts, up to a maximum of about 400 to 500 nucleotides in length. Within the RNA Pol III family, there is further subdivision of natural promoters into 3 subtypes (1, 2 and 3) which are structurally distinct, but also reflect specialization as to which subcellular compartment their products are utilized in. For example, the U6 genes encode small nuclear RNAs which function in the nucleus during RNA splicing, whereas various tRNA genes encode tRNA molecules which function in the cytoplasm during protein synthesis. Thus, one aspect of the present invention is the use and construction of vectors containing multiple Pol III promoters comprising one or more representatives of the type 3 promoters (for example, U6, H1, 7SK, as well as sequence variants thereof) and members of the type 1 or type 2 subclasses (for example, various tRNA gene promoters). Such combinations of promoters provide a means for regulating the relative distribution (nucleus vs. cytoplasm) of shRNA and/or microRNA products and gRNA within the cell. Experimental examples of this localization has been described in several publications, for example lives et al., Gene 171:203-08 (1996); Kawasaki and Taira, Nucleic Acids Res. 31:700-07 (2003); and Boden et al., Nucleic Acids Res. 31:5033-38 (2003).

Vertebrate U6 small nuclear RNA (snRNA) gene promoters are among the founding members of those recognized by RNA polymerase III in which all control elements for initiation are located in the 5'-flanking region. One human U6 gene (U6-1) has been studied extensively and a total of nine full-length U6 loci have been identified in the human genome. Unlike human U1 and U2 snRNA genes, most of the full-length U6 loci are dispersed throughout the genome. Vertebrate U6 and 7SK genes were the first examples of a distinct subclass of pol III promoters that do not contain intragenic control regions, but instead have control elements located in their 5'-flanking regions (type 3 genes). All such type 3 promoters contain OCT, an octamer element located in the distal, or enhancer-like region located approximately 220 base pairs upstream of the start site; SPH, an element adjacent to OCT that is bound by the zinc finger transcription factor SBF/Staf; PSE, a promoter-specific proximal sequence element and TATA-element which directs pol III specificity; although the sequences of these elements are variable. Furthermore, these five full length U6 genes are transcribed to different extents in vitro or after transient transfection of human 293 cells. Of the nine full-length U6 loci, only U6-7 and U6-8 are closely linked and contain highly conserved 5'-flanking regions. However, due to a modest sequence difference in the proximal sequence elements for U6-7 and U6-8, these genes are transcribed at very different levels in transfected cells. Much current interest is focused on this promoter class because they can be employed to produce relatively high levels of synthetic RNAs in cultured cells, for example small interfering RNAs used to induce RNAi-mediated knock-down of specific mRNA targets. One embodiment of the current invention uses different forms of the U6 promoters (SEQ ID NOS: 1-5) to direct expression of chimeric gRNA.

Another embodiment uses H1 promoter variants to direct expression of chimeric gRNA. The human H1 and the 7SK promoters displayed no non-specific interferences compared to the murine and human U6 promoters. Unlike the +1 nucleotide of the U6-like promoters which is always guanosine, the +1 for H1 promoters is adenosine. Interestingly, changing the +1 adenosine to uridine, cytidine or guanosine does not affect gene silencing, indicating that H1 promoters may be more flexible than U6 promoters in regard to +1 sequence changes.

Additional embodiments with RNA pol III promoters, for example silkworm tRNA$^{Ala}$, human 7SL, EBER RNAs and *Xenopus* tRNA$^{Sec}$, 7SK, Y and MRP RNA to drive expression of gRNAs are within the scope of this invention.

Much of the current work has been done expressing a single gRNA and a Cas9 or Cas9n in a single vector construct. Vectors expressing a single gRNA along with Cas9 or Cas9n have been developed in the art to direct Cas9 nucleases to a genomic locus. The double-nicking strategy using Cas9n utilizes a pair of offset gRNAs complementary to the opposite strands of the target site. Offset refers to the number of bases between the most proximate 5' end of one gRNA and 3' end of the other when both are maximally aligned with the nucleic acid being cleaved. For example an offset of 5 bases between two guide RNAs each of 20 nucleotides means that the two guide RNAs, each complementary to a region of the nucleic acid being cleaved are spaced 5 base pairs apart between the 5' end of one gRNA and the 3' end of the other. The offset gRNAs overlap if they have at least one pair of complementary bases when both are maximally aligned with the nucleic acid being cleaved. Depending on whether 5' or 3' overhangs are created following Cas9 cleavage, the offset distances can range from −200 to 200 base pairs. Studies characterizing spacing parameters or gRNA offset between paired gRNAs governing successful Cas9 double-nickase-mediated gene targeting reveal an effective offset window of greater than 100 base pairs long, allowing for a high degree of flexibility in the selection of gRNA pairs (Zhang et. al., 2013). The offset can be for example, 1-200, 1-20 or 5-15 base pairs.

Previous computational analyses have revealed an average targeting range of every 12 base pairs for the *Streptococcus pyogenes* Cas9 in the human genome based on the 5' NGG PAM (Cong et. al., 2013) suggesting that appropriate gRNA pairs are readily identifiable for most loci within the genome. Another aspect that contributes to specificity of the gRNA target sequence is its length. Adjusting the length of the gRNA target sequence can substantially reduce the occurrence of off-target mutations. Based on the natural CRISPR system in *Streptococcus pyogenes*, gRNA target sequence lengths most commonly used are 20-nucleotides in length. Studies have shown that gRNAs with targeting segments of 17- or 18-nucleotides were as or more efficient than full length gRNA target sequences in reaching their targets, those with 15 or 16-nucleotide targeting segments had reduced or no targeting activity (Joung et. al., 2013). In some embodiments the gRNA target sequence lengths are 17- to 30-nucleotides in length. In preferred embodiments the gRNA target sequence lengths are 17- to 20-nucleotides in length. The offset pair of gRNAs needs to be co-transfected into mammalian cells which can lead to lowered or variable transfection efficiencies and result in a heterogeneous population expressing only one gRNA, thereby leading to inefficient genome modification. Additionally, insertion of a single-stranded or double-stranded insert with compatible ends to overhangs created by gRNA-guided Cas9n nicking requires co-transfection of a vector with the desired insert along with the gRNAs. This further increases the variability of the transfection requiring three plasmids to be incorporated into each cell for successful genome modification. Therefore, there exists a need in the art for expression of two or more gRNAs in a single vector construct, thereby reducing the inherent variability and increasing efficiency of transfection.

The present invention provides vectors, kits and associated methods for efficient introduction of inserts encoding two guide RNAs into a single vector, which typically also expresses a Cas9 enzyme, preferably a Cas9 nickase. Introduction by sequential cloning steps is laborious as well as typically requiring use of two selection markers. Such would be even more laborious for screening libraries of paired RNAs in that introduction of each pair would require sequential cloning steps. Synthesizing a single nucleic acid containing DNA segments encoding guide RNA molecules separated by a promoter operably linked to one of the guide RNA molecules and other regulatory sequences would allow the two guide RNAs to be introduced on a single construct in a single step. However, such would require synthesis of a nucleic acid of the order of 400 nucleotides, which is at or beyond the limits of what can readily be accomplished by solid phase synthesis. In the case of libraries, such synthesis would have to be repeated for each paired fragment being introduced.

The invention provides more efficient methods for introducing paired segments of nucleic acids into a vector. Although the methods are exemplified for paired segments encoding paired guide RNA's, the same strategy and principles apply for paired segments encoding other RNAs or proteins that can operate as pair, such as heterodimeric proteins)). For example, the methods can be used to screen pairs of random peptides for a binding activity against a target; screen pairs of RNAi or shRNA for binding activity against a target; to study effects of mutations in subunits of proteins upon co-expression of subunits to form functional heteromeric complexes, for example 5'-AMP-activated protein kinase (AMPK) that plays a critical role in the regulation of cellular energy homeostasis, is a heterotrimer composed of a catalytic subunit (alpha) and two regulatory subunits (beta and gamma). Solid phase synthesis can be used to synthesize an oligonucleotide encoding two guide RNAs. Such a fragment can be of the order of 50 nucleotides long (e.g., 30-100, or 35-60 nucleotides). Such a length is within what is readily accompanied by solid phase synthesis. The oligonucleotide can then be assembled with a spacer nucleic acid encoding a promoter, and elements desired to be placed between the segments encoding the two guide RNAs. Initially after assembly the spacer nucleic acid is to one side of the oligonucleotide encoding the guide RNAs. However, on circularization of the assembled nucleic acid and cleavage between the DNA segments encoding the two guide RNAs, the spacer oligonucleotide and its components now occur between the segments encoding the two guide RNAs. In other words, more nucleotides separate these segments after cleavage than in the circularized nucleic acid. The resulting nucleic acid can now be cloned into a vector with a single cloning step, such that one guide RNA is placed in operable linkage with a promoter already in the vector and the other guide RNA is in operable linkage with the promoter introduced by the spacer oligonucleotide. Thus, two inserts under control of different promoters have been introduced in the same step into a vector. The present method can readily be extended to library screening without proportionately increasing the effort with the number of paired guide RNAs being screened. In this case, multiple oligonucleotides encoding multiple paired guide RNAs are synthesized initially. Then the multiple oligonucleotides can be assembled in the same reaction with the same spacer oligonucleotide. The remaining circularization, cleavage and introduction into vector steps proceed in parallel for all of nucleic acids encoding different paired guide RNAs. Thus, libraries of large numbers of paired guide RNAs can be introduced into a vector without substantially increased effort relative to screening a single pair. Libraries can include for example, at least 2, 5, 10, 100, 1000, 10,000, 100,000 or 1,000,000 paired segments. Some libraries include 50-100,000 paired segments.

In some preferred embodiments, the oligonucleotide encoding two guide RNAs has compatible ends to a genome modifying vector such that the oligonucleotide can be inserted into the vector by a simple cloning step to generate a circular nucleic acid. The spacer oligonucleotide and its components can now be inserted between the two guide RNAs by a simple cloning step wherein the spacer oligonucleotide has compatible ends to the ends generated by cleavage in the region between the two guide RNAs, such that one guide RNA is in operable linkage with a promoter already in the vector and the other guide RNA is in operable linkage with the promoter introduced by the spacer oligonucleotide. In some preferred embodiments the ends are generated by type IIs restriction endonucleases. The present method can easily be extended to generating libraries, wherein multiple oligonucleotides encoding multiple guide RNAs are synthesized initially. Then the multiple oligonucleotides can be inserted into a genome modifying vector in a simple cloning step. The remaining linearization and introduction of spacer oligonucleotide proceeds in parallel for all of the nucleic acids encoding the paired guide RNAs. Thus, libraries of large numbers of paired guide RNAs can be introduced into a vector without substantially increased effort relative to screening a single pair. Libraries can include for example, at least 2, 5, 10, 100, 1000, 10,000, 100,000 or 1,000,000 paired segments. Some libraries include 50-100,000 paired segments.

The assembly reaction between the synthesized oligonucleotide containing the paired segments and spacer oligonucleotide can be a PCR amplification in which the spacer oligonucleotide is the template, the synthesized oligonucleotide is a reverse primer and an additional forward primer is supplied. The forward and reverse primers have complementary segments to the template and primer amplication from it. Complementarity means either perfect complementarity by Watson Crick pairing rules or at least sufficient complementarity to permit hybridization and template directed amplification under conditions of use. In one format, the spacer oligonucleotide is double stranded and the primers are single stranded. Alternatively, each of these molecules can be single stranded. The designation of forward and reverse primers can be reversed. In one format, the forward and reverse primers have mutually complementary 5' overhangs (noncomplementary to the template) that allows circularization of the amplification product. Alternatively, cohesive ends can be generated by restriction digestion after application. In a further variation, the amplification product can be circularized by blunt end ligation.

In an alternative format for the assembly reaction, the synthesized oligonucleotide and spacer oligonucleotide are mutually complementary at their 3' ends and each serves as a template for replication of the other in a sewing type assembly reaction. This reaction results in a double-stranded molecule in which the synthesized oligonucleotide and spacer oligonucleotide are sewn together. Such a molecule can be circularized by annealing of cohesive ends at the 5's of the respective oligonucleotides (i.e., present as synthesized or formed by restriction digestion after assembly) or by blunt end ligation.

As noted, the spacer oligonucleotide as well as providing a promoter to express one of the paired nucleic acids on the synthesized oligonucleotides may provide additional elements. One such additional element is a transcriptional terminator. The transcriptional terminator serves to terminate transcription of the paired nucleic acid segment to be expressed from the vector supplied promoter. The transcriptional terminator is thus preferably position upstream or 5' to the promoter present on the spacer oligonucleotide. Another element is DNA encoding a scaffold RNA (SEQ ID NO: 204). This scaffold RNA is positioned upstream or 5' of the terminator element such that on circularization of the amplification product it can be placed in operable linkage with DNA encoding a guide RNA on the synthesized fragment. Optionally DNA encoding a short RNA linker can be positioned adjacent the DNA encoding the scaffold RNA on the spacer so it is between the DNA encoding the guide and scaffold RNAs on circulation of the amplification product.

After recircularization, the amplification product is linearized by cleavage at one or more different sites to generate distinct ends than those joined by circularization. Preferably, the linearization proceeds by cleavage at one more sites between the paired segments of the original synthesized oligonucleotide.

The resulting linearized nucleic acid now has the promoter originally present on the spacer fragment between the paired nucleic acid segments, such that one of the segments downstream from the promoter is in operable linkage with it. In a preferred format, such a linearized nucleic acid includes from 5'-3' one of the paired nucleic acid segments encoding a guide RNA (contributed by the synthesized oligonucleotide), a DNA segment encoding a scaffold RNA (contributed by the spacer oligonucleotide), a transcriptional terminator (contributed by the spacer oligonucleotide), a promoter (contributed by the spacer oligonucleotide) and the other paired nucleic acid segment encoding a guide RNA (contributed by the synthesized oligonucleotide).

The linear nucleic acid can now be introduced into an expression vector so that both of the paired nucleic acids can be expressed. Introduction is preferably orientated such that the linear nucleic acid can only be ligated in the desired orientation into the vector. Such can be arranged by providing the linear nucleic acid with different cohesive ends, each of which joins with its complementary end in a linearized form of the vector. The linearized nucleic acid is introduced into the vector such that a promoter supplied by the vector and 5' to the insertion, is placed in operable linkage with the 5' paired nucleic acid segment on the linearized nucleic acid. In some formats, the vector also supplies a DNA segment encoding a guide scaffold RNA and a transcription termination site 3' to insertion of the linearized nucleic acid. Optionally the vector also supplies a DNA segment encoding an RNA linker 5' of the DNA encoding the scaffold RNA. Accordingly after insertion of the linearized nucleic acid, the DNA segment encoding the scaffold RNA (SEQ ID NO: 204) is placed in operable linkage with the 3' most of the paired segments on the linearized nucleic acid, and the transcriptional terminator terminates transcription from the promoter supplied by the linearized nucleic acid.

The end result is that after insertion of the linearized nucleic acid into the vector each of the paired segments can be expressed from its own transcriptional unit. One paired segment is expressed from a promoter supplied by the vector ending at a transcriptional terminator supplied by the linearized nucleic acid. The other paired segment is expressed from a promoter supplied on the linearized nucleic acid ending at a transcriptional terminator supplied by the vector. When the paired nucleic acid segments encode guide RNA's, each of the guide RNAs is preferably expressed as a fusion with a scaffold RNA 3' to the guide RNA, the DNA encoding one scaffold RNA being supplied by the vector, and the other from the linearized nucleic acid, and originally from the spacer oligonucleotide.

Two or more gRNA expression cassettes directed by a U6 RNA pol III promoter in one expression construct have been recently described in the art (Larson et al. 2013. *Nature Protocols*, Vol. 8 No. 11, 2190-2196) wherein the gRNA expressing vector is Co-transfected with a mutated inactive form of Cas9 expressed on a separate plasmid for CRISPR interference (CRISPRi) studies. The present invention describes a single genome modifying construct with multiple gRNA expression cassettes along with a Cas9, Cas9n (nickase) or dCas9 for genome modification or transcriptional regulation.

In a preferred embodiment, a genome modifying vector comprising two RNA pol III promoters U6.1 (SEQ ID NO: 3) and U6-8cc (SEQ ID NO: 1) are used to direct expression of two gRNA molecules from expression cassettes that are in tandem orientation in the same direction. Additionally, the genome modifying vector comprises an expression cassette capable of driving high protein expression, for example a promoter comprising the CMV immediate early enhancer such as a mammalian promoter selected from CMV, CAG and CBh or the EF1 alpha promoter. These promoters direct strong constitutive expression of Cas9n (nickase) or Cas9 (wild type) or dCas9 (nuclease inactive). Expression of Cas9 nuclease may be monitored by coupling its expression to that of a fluorescent reporter protein, for example via an IRES or 2A/CHYSEL element. The genome modifying vector may further comprise a bacterial resistance marker and a bacterial origin of replication.

Figure 2A:
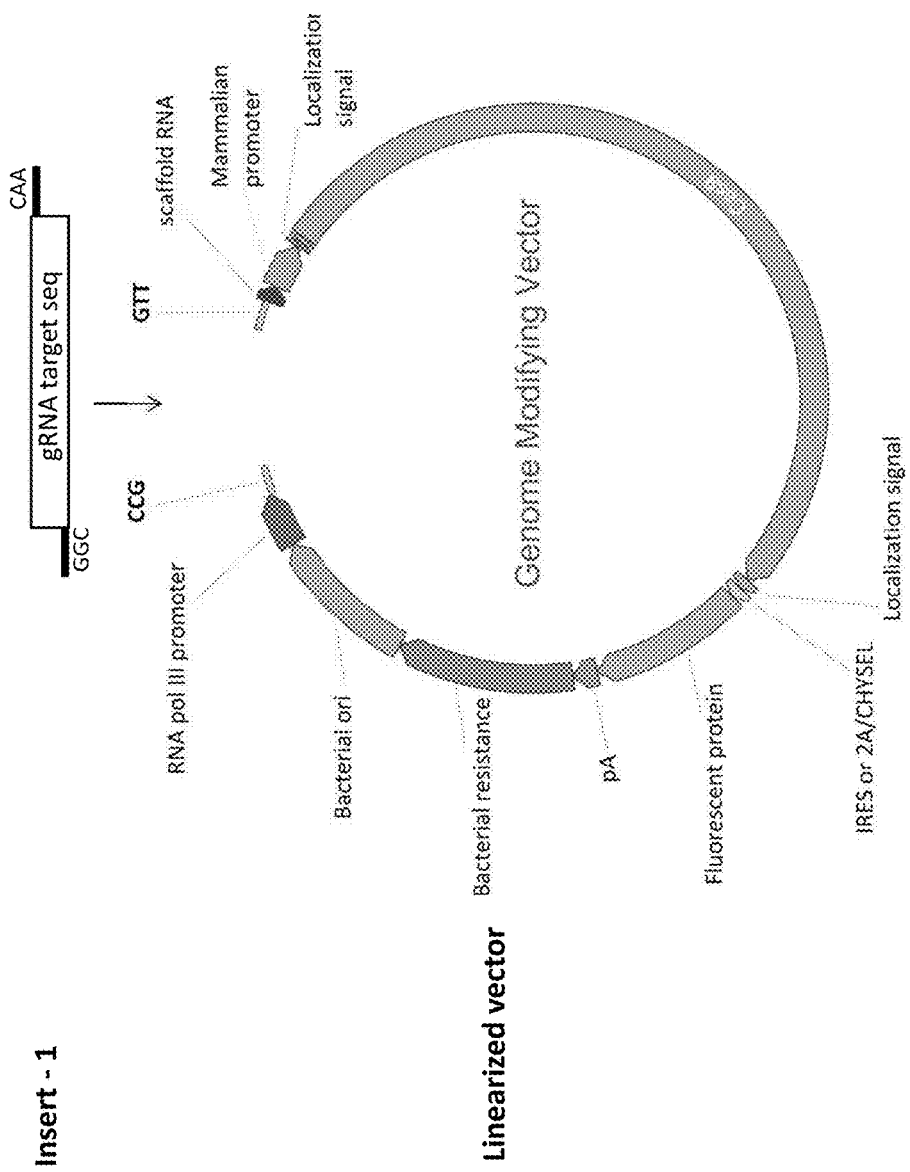
FIG. 2A: shows a plasmid map of a genome modifying vector that has been linearized with type IIs restriction endonuclease SapI to leave overhangs 5'-CCG-3' at one end and 5'-GTT-3' at the other end. A gRNA sequence, Insert 1 is cloned into a genome modification vector comprising a cas9 gene coupled to a fluorescent protein via an IRES or 2A/CHYSEL element, a pol III promoter, a pol III terminator and an RNA scaffold sequence, thereby producing a genome modification construct comprising a cas9 gene, a pol III promoter, a pol III terminator and complete gsRNA sequence. In preferred embodiments the cloning is performed in a single reaction comprising restriction endonuclease and DNA ligase. In some embodiments the cas9 gene encodes a cas9 nickase or dCas9.
Figure 2B:
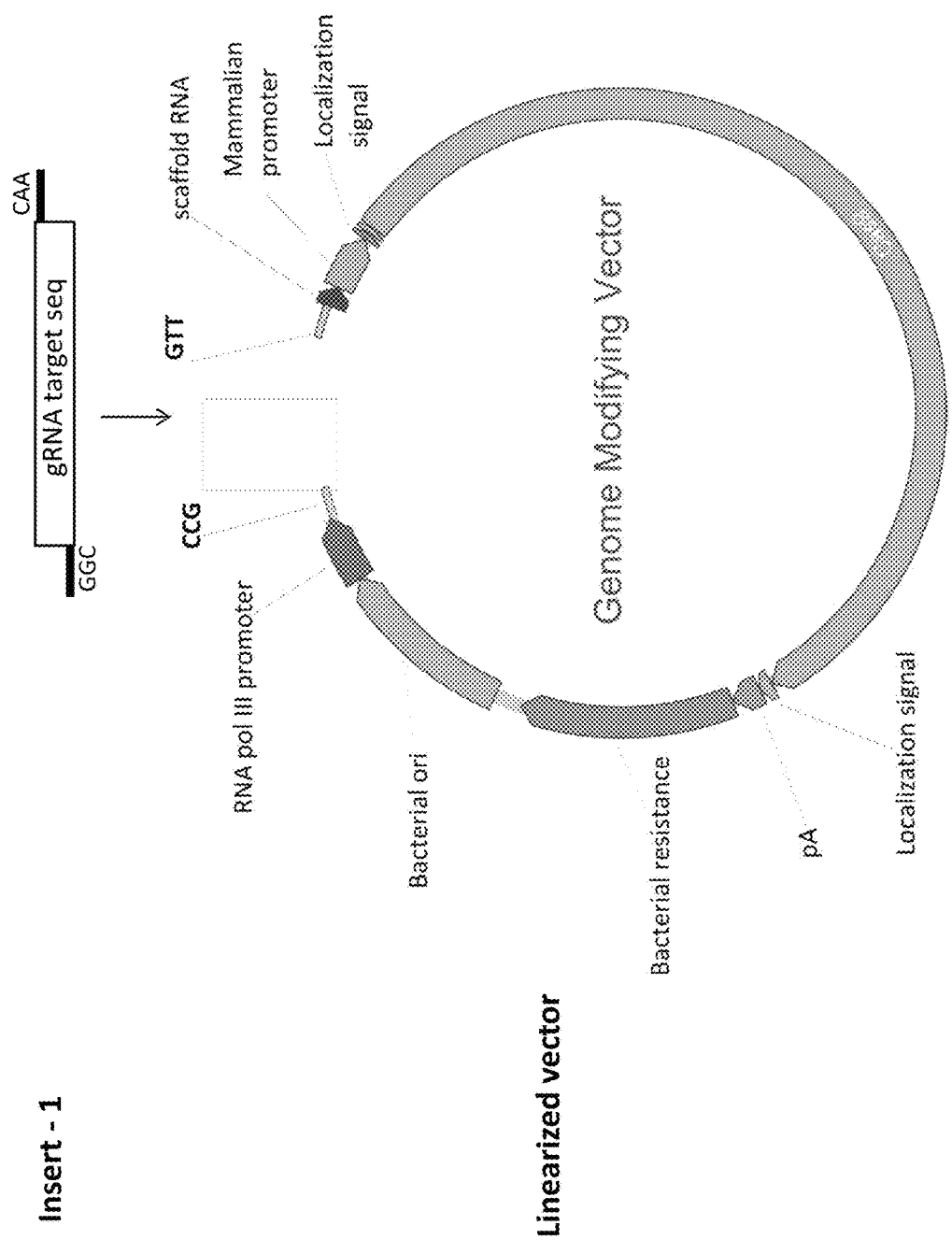
FIG. 2B: shows a plasmid map of a genome modifying vector that has been linearized with type IIs restriction endonuclease SapI to leave overhangs 5'-CCG-3' at one end and 5'-GTT-3' at the other end. A gRNA sequence, Insert 1 is cloned into a Genome Modification Vector comprising a cas9 gene, a pol III promoter, a pol III terminator and a scaffold RNA sequence, thereby producing a genome modification construct comprising a cas9 gene, a pol III promoter, a pol III terminator and complete gsRNA sequence. In preferred embodiments the cloning is performed in a single reaction comprising restriction endonuclease and DNA ligase. In some embodiments the cas9 gene encodes a cas9 nickase or dCas9.
Figure 2C:
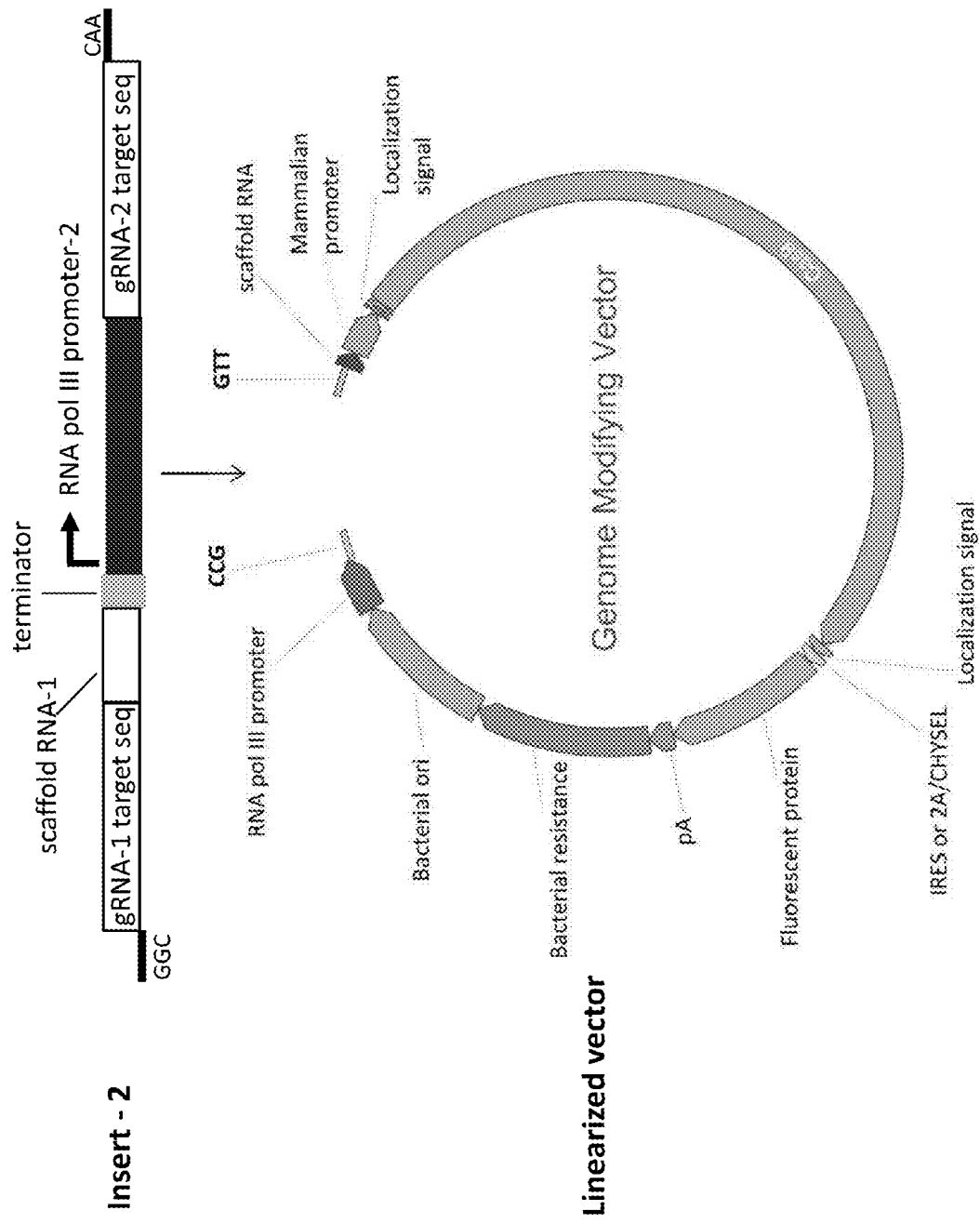
FIG. 2C: shows a plasmid map of a genome modifying vector that has been linearized with type IIs restriction endonuclease SapI to leave overhangs 5'-CCG-3' at one end and 5'-GTT-3' at the other end. Insert 2 comprises from left to right a first gRNA sequence, a scaffold RNA sequence, a terminator, a promoter, a second gRNA sequence. Insert 2 is cloned into a genome modification vector comprising a cas9 gene coupled to a fluorescent protein via a IRES or 2A/CHYSEL element, a pol III promoter, a pol III terminator and RNA scaffold sequence, thereby producing a genome modification construct comprising a cas9 gene, two polIII promoters, two polIII terminators and two complete gs RNA sequences. The resulting product nucleotide is a construct that expresses two gsRNAs that are operably linked to two RNA pol III promoters. In preferred embodiments the cloning is performed in a single reaction comprising restriction endonuclease and DNA ligase. In some embodiments the cas9 gene encodes a cas9 nickase or dCas9.
Figure 2D:
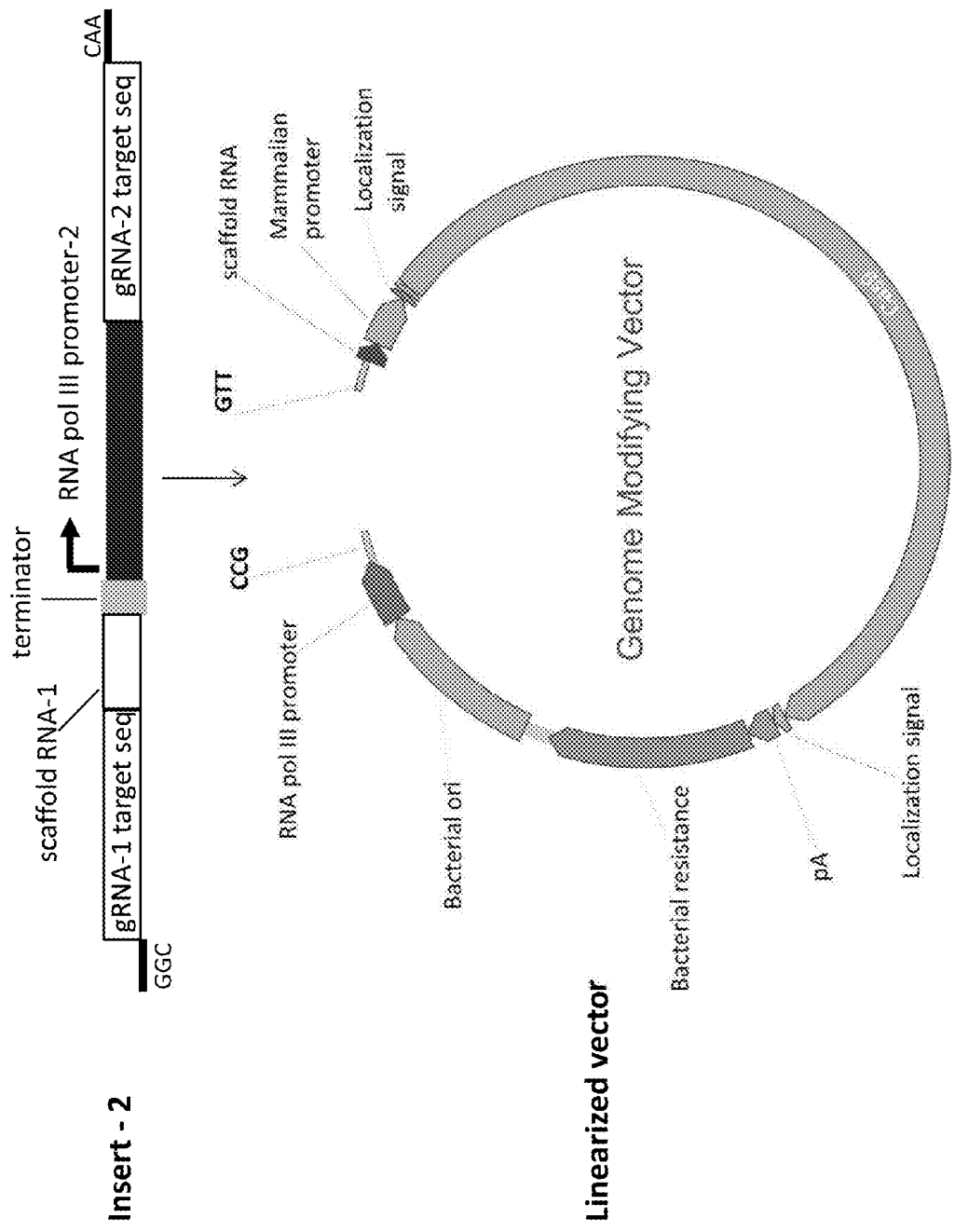
FIG. 2D: shows a plasmid map of a genome modifying vector that has been linearized with type IIs restriction endonuclease SapI to leave overhangs 5'-CCG-3' at one end and 5'-GTT-3' at the other end. Insert 2 comprising a complete gRNA sequence (including the RNA scaffold sequence) a pol III terminator, a pol III promoter, and a second gRNA sequence is cloned into a genome modification vector comprising a cas9 gene, a pol III promoter, a pol III terminator and an RNA scaffold sequence, thereby producing a genome modification construct comprising a cas9 gene, two pol III promoters, two pol III terminators and two complete gsRNA sequences. The resulting product nucleotide is a construct that expresses two gsRNAs that are operably linked to two RNA pol III promoters. In preferred embodiments the cloning is performed in a single reaction comprising restriction endonuclease and DNA ligase. In some embodiments the cas9 gene encodes a cas9 nickase or dCas9.
Figure 2E:
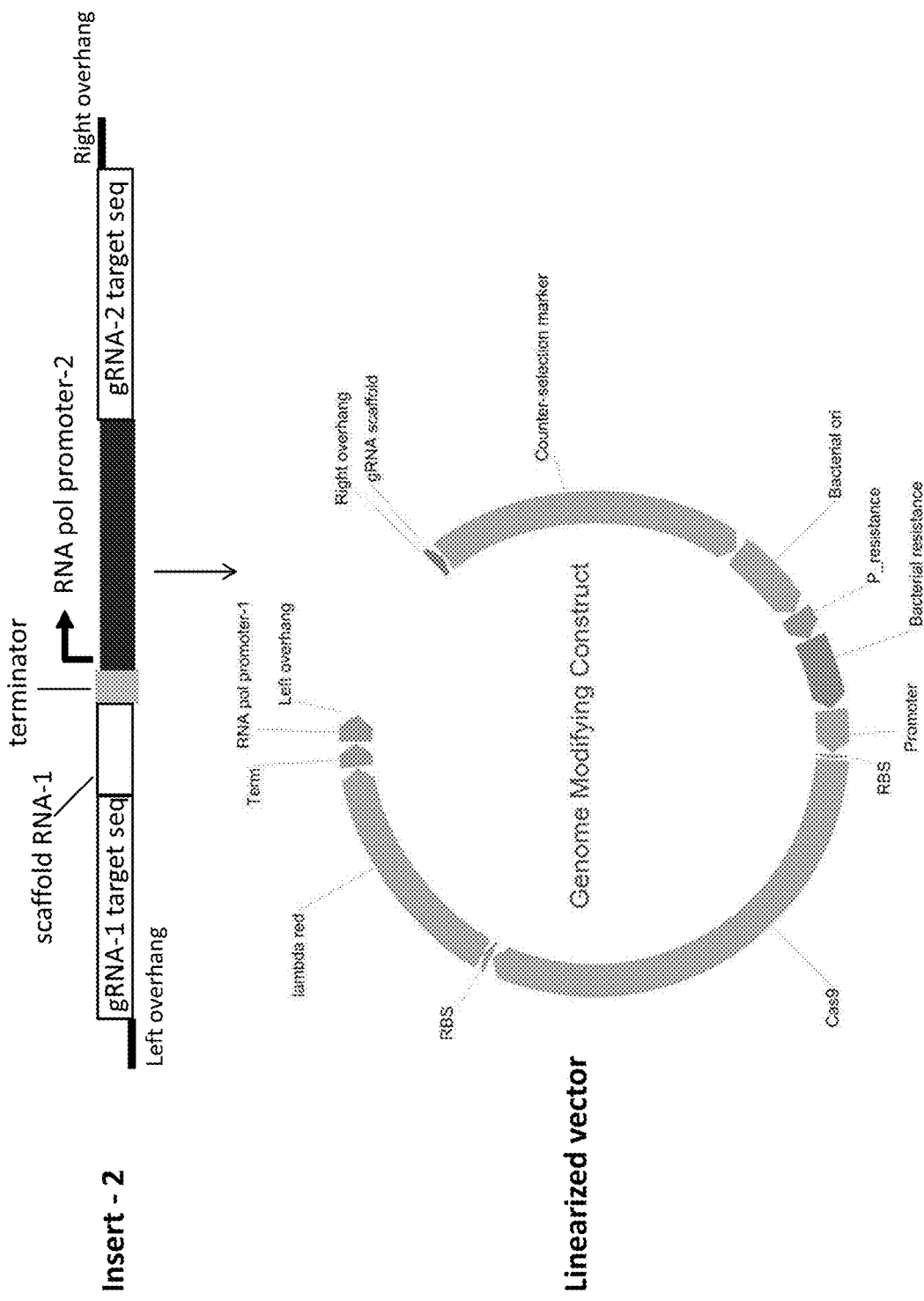
FIG. 2E: shows a plasmid map of a genome modifying vector that has been linearized with type IIs restriction endonuclease SapI to leave overhangs. Insert 2 comprising a complete gRNA sequence (including the RNA scaffold sequence) a pol terminator, a prokaryotic promoter, and a second gRNA sequence is cloned into a genome modifying vector comprising a cas9 gene, a prokaryotic promoter, a pol terminator and an RNA scaffold sequence, thereby producing a genome modifying construct comprising a cas9 gene, two prokaryotic promoters, two pol terminators and two complete gsRNA sequences. The resulting product nucleotide is a construct that expresses two gsRNAs that are operably linked to two RNA pol promoters. In preferred embodiments the cloning is performed in a single reaction comprising restriction endonuclease and DNA ligase. In some embodiments the cas9 gene encodes a cas9 nickase or dCas9.

In another preferred embodiment, a genome modifying vector comprising two constitutive prokaryotic promoters are used to direct expression of two gRNA molecules from expression cassettes that are in tandem orientation in the same direction (FIG. 2E). Additionally, the genome modifying vector comprises an expression cassette capable of driving high protein expression, for example an inducible promoter selected from the rhamnose inducible promoter rhaBAD, IPTG inducible promoters T5 or T7 and tetracycline inducible promoter ptet. In some other embodiments, the promoter is constitutive. These promoters direct inducible or constitutive expression of Cas9n (nickase) or Cas9 (wild type) or dCas9 (nuclease inactive). Expression of Cas9 nuclease may be monitored by coupling its expression to that of a fluorescent reporter protein, for example via fusion. In some preferred embodiments, the genome modifying vector comprises a recombinase, for example the lambda red operon that includes genes beta, exo and gam to facilitate homologous recombination events in *E. coli*. Lambda red recombinase system from bacteriophage lambda enhances the recombination of linear DNA in the *E. coli* chromosome, as it promotes efficient double strand break repair (HDR) recombination. These aspects facilitate use of a single vector for genome modification without the need to co-transform or use multiple growth and editing hosts, advantages that have been described herein. The genome modifying vector may further comprise a bacterial resistance marker, a counter-selectable marker and a bacterial origin of replication. In some preferred embodiments, the bacterial origin of replication SC101 ori is temperature sensitive. Use of a temperature sensitive origin of replication has the advantage that the host cells can be easily cured of any residual plasmid by temperature selection. Donor nucleic acid, either linear or circular comprising one, two, three, four or more insert fragments can be inserted by homology directed repair (HDR) for insertion at Cas9 mediated double stranded breaks. The donor insert fragments have flanking ends comprising homology arms to facilitate insertion of insert fragments at the site of Cas9 mediated double stranded breaks. The homology arms undergo homologous recombination with corresponding segments in a genome such that a portion of the genome modifying vector between the points of homologous recombination in the vector replaces a genomic segment between the points of homologous recombination in the genome. In preferred embodiments, the insert fragments have flanking ends comprising homology arms and Cas9 cleavage sites such that the insert fragments are cut by Cas9 to generate ends compatible to ends flanking the Cas9 mediated double stranded breaks. In other embodiments, the insert fragments have flanking ends comprising homology arms and restriction cleavage sites such that the insert fragments are cut by the restriction enzyme to generate ends compatible to ends flanking the Cas9 mediated double stranded breaks. In some embodiments, the one, two, three, four or more donor insert fragments are present on the same genome modifying construct. In other embodiments, the one, two, three, four or more donor insert fragments are present on a separate plasmid or as a linear polynucleotide. Multiple donor fragments can be introduced with different homology arms that allow insertion at multiple Cas9-mediated double-stranded breaks especially when using multiple guides. A donor nucleic acid with insert fragments or insert fragments incorporated in the genome modifying construct allows simultaneous double-stranded breaks and insertion of desired fragments at sites of Cas9 cleavage in the genome.

In other embodiments, two gRNAs transcribed from a single construct using two different or same RNA polymerase promoters wherein the gRNA directs dCas9 to different genomic loci along the target gene for transcriptional regulation and/or gene silencing. Multiple gRNAs expressed in a single construct can also be used simultaneously to regulate multiple genes or to synergistically control a single gene for enhanced repression. They can also be used for tuning silencing to achieve a moderate level of gene repression.

In one embodiment, an offset pair of gRNAs complementary to opposite strands of a target genomic locus are expressed using U6 promoter variants (SEQ ID NOS: 1-5) placed in a tandem orientation. Another embodiment expresses an offset pair of gRNAs using different H1 promoter variants placed in a tandem orientation wherein the two gRNAs direct Cas9n to opposite strands of nucleic acid being cleaved. Other embodiments include the U6 or H1 promoter variants that are placed in opposite orientation driving expression of two gRNAs. Use of different orientations of the U6 or H1 promoter variants, either as combinations of U6 variants, H1 variants or combinations of U6 and H1 variants directing expression of two or four gRNAs is expressly contemplated. Other embodiments include two gRNAs that are complementary and directed to different target loci operably linked to either the U6 variants or the H1 RNA pol III promoters in tandem or opposite orientation and expressed along with Cas9 in the same vector construct. Additional embodiments include expression of Cas9 coupled to reporter proteins, using 2A (SEQ ID NOS: 10) or IRES elements.

Messenger RNA molecules in eukaryotic cells are generally monocistronic, that is, they usually encode a single polypeptide. This is because translation in eukaryotes generally occurs by a process in which the ribosome binds to a structure at the 5' end of the mRNA and then "scans" down the mRNA until it finds an initiation codon (generally AUG) where it begins translation. It then translates the mRNA, producing the encoded polypeptide, until it reaches a termination codon (generally UAA, UAG or UGA) which causes the ribosome to end translation and dissociate from the mRNA. Certain eukaryotic viruses have evolved mechanisms by which they can express more than one polypeptide from a single mRNA. These include internal ribosome entry sites (IRES), and cis-acting hydrolase element (CHYSEL) sequences. An IRES provides a structure to which the ribosome can bind that does not need to be at the 5' end of the mRNA. It can therefore direct a ribosome to initiate translation at a second initiation codon within an mRNA, allowing more than 1 polypeptide to be produced from a single mRNA. A CHYSEL sequence causes a translating eukaryotic ribosome to release the growing polypeptide chain that it is synthesizing without dissociating from the mRNA. The ribosome continues translating, and therefore produces a second polypeptide. A single genetic construct can contain more than one IRES or CHYSEL sequence, and it can contain both IRES and CHYSEL sequences, so can therefore encode 2 or 3 or 4 or 5 or 6 or more than 6 polypeptides on a single mRNA.

IRES or CHYSEL sequences can therefore be used as coupling elements, to link the expression of a gene of interest to the expression of a selectable protein that provides a physical, chemical or biological method for selecting cells on the basis of how much of the selectable protein is expressed. The use of certain selectable proteins to indicate the status or functionality of a genetic construct within an organism is an aspect of the invention. The combining of selectable proteins with IRES or CHYSEL sites to indicate the status or functionality of Cas9, Cas9n or dCas9, or to indicate the level of expression of Cas9, Cas9n or dCas9 is another aspect of the invention.

In some embodiments, a genome modifying vector has restriction endonuclease sites between the RNA pol III promoter and the RNA pol III terminator sequence that facilitate cloning of different guide sequences. In preferred embodiments, these restriction endonuclease sites are type IIs restriction sites. Type IIs restriction endonucleases recognize asymmetric DNA sequences and cleave both DNA strands at fixed positions, typically several base pairs away from the recognition sites. This property makes type IIs restriction endonucleases particularly useful for assembling DNA fragments, where fragments with matching type IIs-generated ends are annealed and ligated, leaving an assembled DNA product without restriction recognition sequence scars at the ligation junctions. Type IIs restriction endonucleases that recognize non-palindromic sequences of 5, 6 or 7 base pairs, are found at an average frequency of one in 512, 2048 or 8192 base pairs respectively. It is therefore, relatively easy to identify type IIs restriction endonucleases that do not cut inside a typical gene-sized DNA fragment or a gRNA fragment.

A genome modifying vector can be constructed to permit cloning using type IIs restriction endonucleases and ligase by incorporating a Stuffer, comprising a counter-selectable marker and flanked by type IIs restriction sites, into a vector comprising a selectable marker. It is advantageous if the type IIs restriction sites are chosen such that cleavage of the genome modifying vector with one or more type IIs restriction enzymes yields a linear Nucleic Acid Fragment comprising a selectable marker and with ends that are not compatible with each other. This design allows directional insertion of an insert DNA fragment that has cohesive ends compatible with the linear Nucleic Acid Fragment of the genome modifying vector. The insert DNA fragment may be prepared by annealing a pair of oligonucleotides, or more preferably by PCR amplification and restriction digestion. In preferred embodiments the genome modifying vector ends are also not pseudo-compatible with each other; that is they do not anneal with each other by forming at least one non-standard Watson-Crick base pair (i.e., T or U with G) in a way that can be joined by a DNA ligase with reasonable efficiency.

In some embodiments compatible ends are produced from one or more of the type IIs enzymes that produce a 1 bp 5'-overhang selected from the group consisting of AlwI, BccI, PleI, AsuC2I, BceFI, BcnI, BisI, Bme1390I, BmrFI, BseBI, BsiLI, Bst2UI, BstOI, CauII, Fsp4HI, GluI, ItaI, MspR9I, MvaI, SatI, AspI, PsyI, TelI, and BstENI. In some embodiments compatible ends are produced from one or more of the type IIs enzymes that produce a 2 bp 5'-overhang is selected from the group consisting of BceAI, FauI, EcoP15I, Hpy188III, SmuI, and Hpy178III. In some embodiments compatible ends are produced from one or more of the type IIs enzymes that produce a 3 bp 5'-overhang selected from the group consisting of BspQI, Bst6I, EarI, Eam1104I, Ksp632I, LguI, PciSI, and SapI. In some embodiments compatible ends are produced from one or more of the type IIs enzymes that produce a 4 bp 5'-overhang selected from the group consisting of AarI, Acc36I, AceIII, AspBHI, Alw26I, BbvI, BcoDI, BsmAI, BsmFI, BbsI, BfuAI, BsaI, Bsa-HF, BsmBI, Btg2I, BmsI, BseXI, BsIFI, BsoMAI, Bst71I, BstMAI, BstV1I, BbvII, BpiI, BpuAI, Bso31I, BspTNI, BstV2I, BveI, Eco31I, Esp3I, FspEI, FokI, FaqI, LpnPI, LweI, MspJI, R9896, SfaNI, SgeI, SgrTI, and Sth132I. In some embodiments compatible ends are produced from one or more of the type IIs enzymes that produce a 5 bp 5'-overhang is CseI or HgaI. In some embodiments compatible ends are produced from one or more of the type IIs enzymes that produce a 6 bp 5'-overhang is CjeI or CjePI. In some embodiments compatible ends are produced from one or more of the type IIs enzymes that produce a 7 bp 5'-overhang including TscAI.

In some embodiments compatible ends are produced from one or more of the type IIs enzymes that produce a 1 bp 3'-overhang selected from the group consisting of MnII, HphI, HpyAV, MboII, BciVI, BmrI, BlsI, Hin4II, BmeRI, AspEI, and NruGI. In some embodiments compatible ends are produced from one or more of the type IIs enzymes that produce a 2 bp 3'-overhang selected from the group consisting of BspCNI, BtsCI, BtsIMutI, AcuI, BpmI, BpuEI, BseRI, BsgI, BsrDI, BtsI, EciI, MmeI, NmeAIII, BcgI, CspCI, DrdI, BseGI, BseMII, BstF5I, TspDT1, TspGWI, ApyPI, Bce831, BsbI, Bse3DI, BseMI, CchII, CchIII, CdpI, CjeNIII, CstMI, DrdIV, Eco571, Eco57MI, GsuI, NlaCI, PlaDI, PspPRI, RdeGBII, RdeGBIII, SdeAI, TaqII, TsoI, Tth111II, WviI, AquII, AquIV, DraRI, MaqI, PspOMII, RceI, RpaB5I, RpaBI, RpaI, SstE37I, NgoAVIII, AasI, AlfI, BdaI, and DseDI. In some embodiments compatible ends are produced from one or more of the type IIs enzymes that produce a 3 bp 3'-overhang selected from the group consisting of AlwNI, DraIII, DraIII-HF, BglI, BsaXI, BsII, BstAPI, MwoI, Pf1MI, SfiI, RleAI, AdeI, CaiI, PstNI, AccB71I, AfiI, BasI, Bsc4I, BseLI, BsiYI, BstMWI, HpyF10VI, Pf1BI, and Van91I. In some embodiments compatible ends are produced from one or more of the type IIs enzymes that produce a 4 bp 3'-overhang including BstXI. In some embodiments compatible ends are produced from one or more of the type IIs enzymes that produce a 5 bp 3'-overhang selected from the group consisting of BaeI, ApaBI, BplI, FalI, HaeIV, Hin4I, Bsp24I, PpiI, TstI, AloI, ArsI, BarI, PsrI, and AjuI.

A genome modifying vector can be joined with an insert comprising a sequence-targeting portion of a gRNA can be constructed by mixing into a single reaction: the genome modifying vector, the insert, at least one type IIs restriction enzyme that recognizes sites in the insert, and a DNA ligase.

In a preferred embodiment, the type IIs restriction endonuclease is SapI. Because the sequence of the cleaved end of the DNA is not contained within the recognition sequence, any compatible overhangs may be selected. Thus it is possible to completely control the sequence of the genome modifying construct, without being forced to incorporate restriction sites or recombination sequences. In preferred embodiments one overhang in the genome modifying vector comprises sequences complementary to the last bases of the pol III promoter and the first transcribed base; in some embodiments one overhang in the genome modifying vector comprises 5'-CGG-3'. In preferred embodiments one overhang in the genome modifying vector comprises sequences in the chimeric tracr sequence; in some embodiments one overhang in the genome modifying vector comprises 5'-GTT-3'.

Figure 1B:
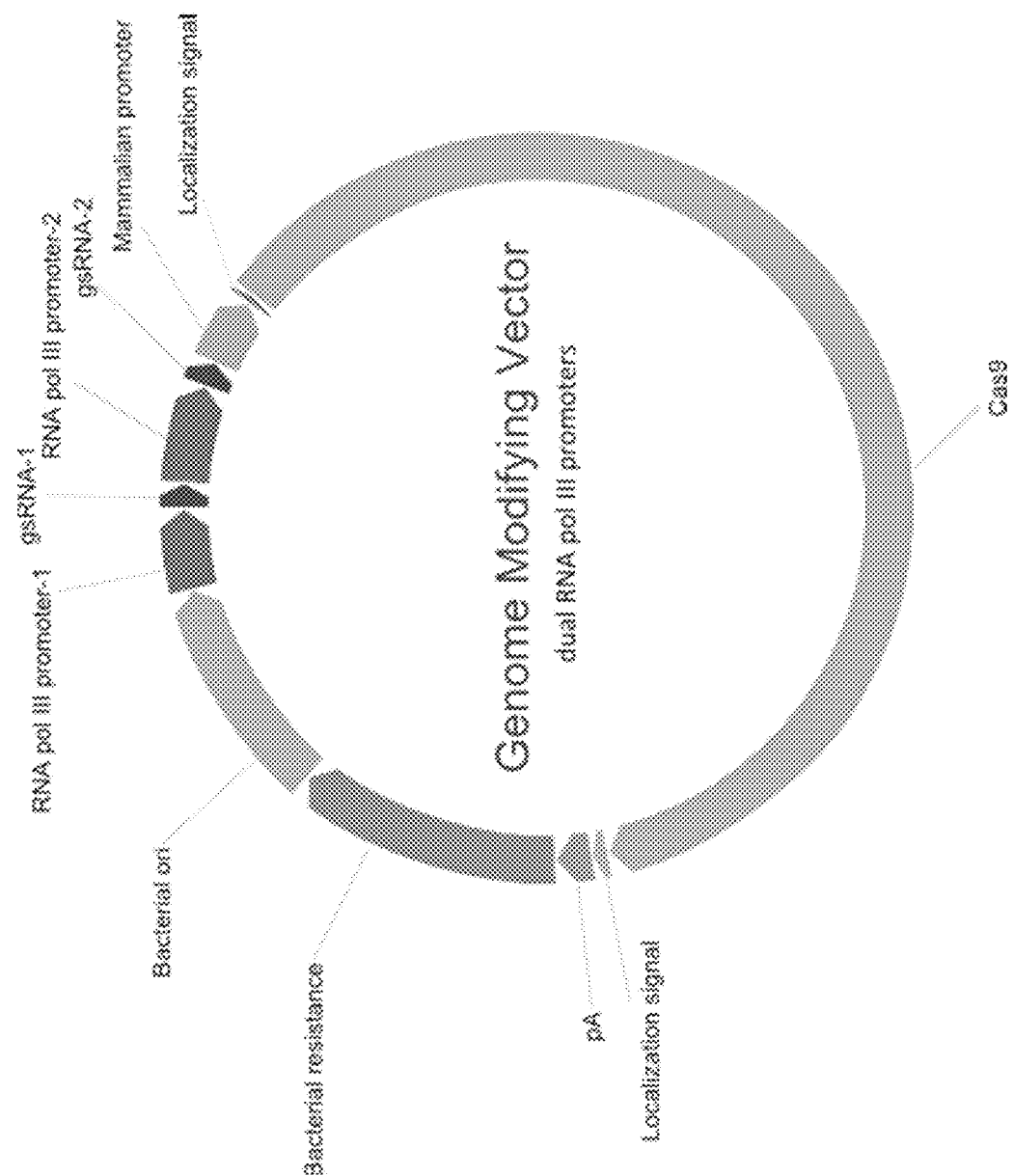
FIG. 1B: shows a plasmid map of a genome modifying construct with two RNA pol III promoters positioned to direct expression of two gsRNA molecules from adjacent expression cassettes in the same direction. Additionally a mammalian promoter directs expression of Cas9N (nickase), Cas9 wt (wild type) or dCas9. The plasmid also comprises a bacterial origin of replication and a bacterial antibiotic resistance gene, shown. Similarly, other embodiments with three or more RNA pol III promoters directing expression of three or more gsRNA molecules from expression cassettes placed in tandem in the same or opposite directions is within the scope of this invention.

In some embodiments, an insert comprising a partial gRNA sequence is cloned into a genome modifying vector comprising a cas9 gene, a pol III promoter, a pol III terminator and part of a chimeric tracr sequence (SEQ ID NO: 204), thereby producing a genome modifying construct comprising a cas9 gene, a pol III promoter, a pol III terminator and complete gRNA sequence. In preferred embodiments the cloning is performed in a single reaction comprising restriction endonuclease and DNA ligase (FIGS. 1A and 1B).

In some embodiments, an insert comprising a complete gRNA sequence (including the chimeric tracr sequence) a pol III terminator, a pol III promoter, and part of a gRNA sequence is cloned into a genome modifying vector comprising a cas9 gene, a pol III promoter, a pol III terminator and part of a chimeric tracr sequence, thereby producing a genome modification construct comprising a cas9 gene, two pol III promoters, two pol III terminators and two complete gRNA sequences (FIGS. 2A and 2B). In preferred embodiments the cloning is performed in a single reaction comprising restriction endonuclease and DNA ligase. In some embodiments the cas9 gene encodes a cas9 nickase. In some embodiments the insert is generated by PCR using a template with part of a chimeric tracr sequence and an RNA pol III promoter. The resulting genome modifying construct expresses two gRNAs, each of which is operably linked to a RNA pol III promoter. In a preferred embodiment, the genome modifying vector fragment has the U6-1 (SEQ ID NO: 3) RNA pol III promoter and the template for PCR contains the U6-8cc (SEQ ID NO: 1) RNA pol III promoter.

In some other preferred embodiments, the genome modifying vector fragment has one constitutive prokaryotic promoter and the template for PCR contains the second constitutive prokaryotic promoter for genome modification in a bacterial host.

In some embodiments the genome modifying vector further comprises a double-stranded DNA break or a dephosphorylated double-stranded DNA break, or a counter-selectable marker within the Stuffer Fragment, in some embodiments the counter-selectable marker is sacB, rpsL, tetAR, pheS, thyA, lacY, gata-1, ccdB, kid or barnase. In specific embodiments, the antibiotic resistant gene is a gene selected from the group consisting of an ampicillin resistant gene, a kanamycin resistant gene, a chloraphenicol resistant gene, and a zeocin resistant gene.

Additional embodiments include expression constructs with two or more gRNA offset pairs that allow directed genome modification with Cas9n (nickase) at 'safe harbor' genomic loci. 'Genomic safe harbors' are chromosomal locations where therapeutic transgenes can integrate and function in a predictable manner, the locus is considered to be both transcriptionally active and the disruption of which does not lead to discernible phenotypic effects across cell types. There are a number of known safe harbor genomic loci including AAVS1 which is found in the $PPP_1R_{12}C$ gene, human Rosa26 and CCR5. The AAVS1 site in chromosome 19 (position 19q13, 42) was identified as a repeatedly recovered site of integration of wild type AAV in the genome of cultured human cell lines that had been infected with AAV. Integration in the AAVS1 locus disrupts the gene phosphatase 1 regulatory subunit 12C ($PPP_1R_{12}C$; also known as MBS85), which encodes a protein with a function that is not clearly delineated. CCR5 located on chromosome 3 (position 3p21, 31) encodes the major co-receptor for HIV-1 and disruption of this locus is not associated with any major pathology. The human Rosa26 locus was first identified by means of homology to mouse Rosa26 in chromosome 2 (position 3p25, 3). Endogenous transcripts are detected in multiple adult human tissues at variable levels, but their role is presently unknown.

Figure 3A:
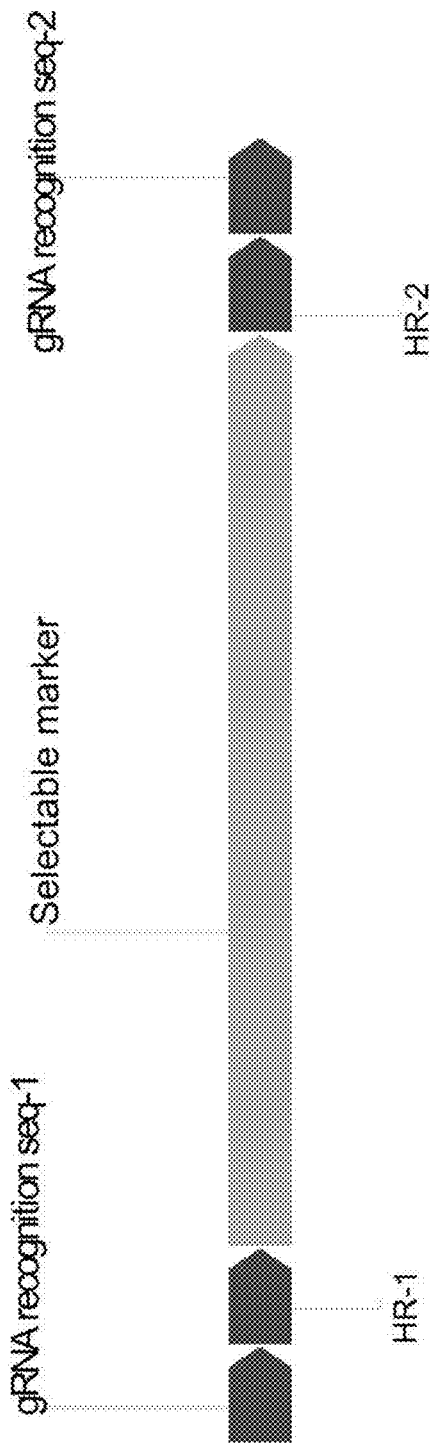
FIG. 3A: shows a linear fragment or polynucleotide comprising two sequences that are homologous to two sequences in the genome of the target organism near the target sequence for the guide RNAs called gRNA recognition sequence 1 and 2; two homologous sequences HR1 and HR2 on either side of a selectable marker that get integrated into the gRNA-directed Cas9 cleavage site in the genome. This fragment can be independently cotransfected to mediate insertion into genomic sites cleaved by gRNA directed Cas9.
Figure 3B:
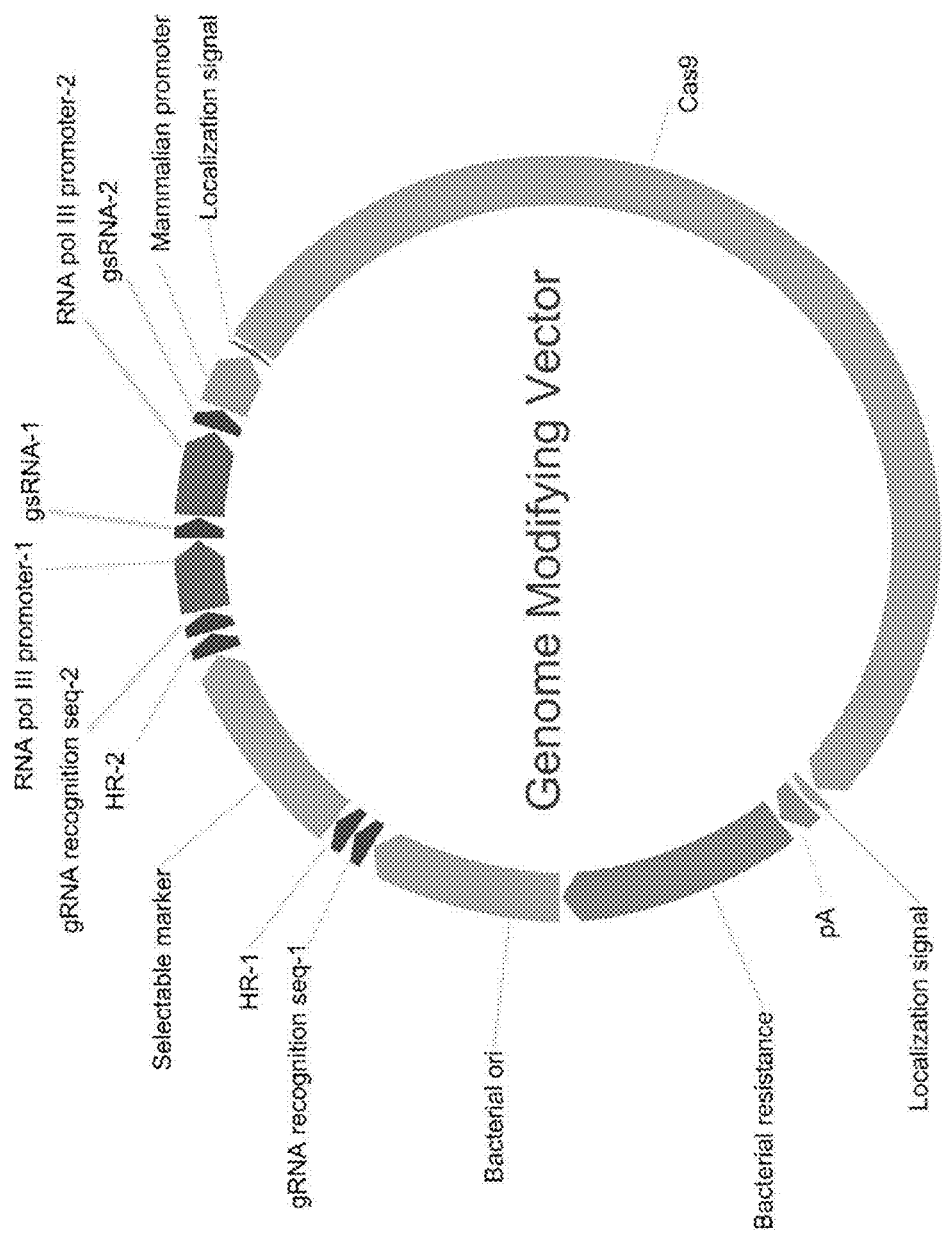
FIG. 3B: shows a plasmid map of a genome modifying construct with two RNA pol III promoters positioned to direct expression of two gsRNA molecules from adjacent expression cassettes in the same direction; a mammalian promoter directs expression of Cas9N (nickase), Cas9 wt (wild type) or dCas9 that may be coupled to a fluorescent protein via an IRES or 2A/CHYSEL element (not shown); a bacterial origin of replication and a bacterial antibiotic resistance gene, shown. Additionally, the genome modifying vector may comprise a cassette with two gRNA recognition sequences (i.e., target sites for gRNA-1 and gRNA-2) that can be cleaved by the gRNA target sequence; two homologous regions HR-1 and HR-2 that flank a selectable marker and serve as recognition sites upon integration into a Cas9 cleaved genomic locus. This genome modifying construct allows genome modification as well as integration of a selectable marker with homologous ends in a single transfection.

Additional embodiments include a second polynucleotide with recognition sequences surrounding a selectable marker to be integrated into genomic loci via gRNA directed Cas9 genome modification. This is achieved by incorporation of recognition or homologous sequences on either side of a selectable marker. This cassette with the selectable marker flanked by homologous sequences is further flanked by the gRNA target sequences (FIGS. 3A and 3B). Cleavage of the target sequences by gRNA directed Cas9 nuclease in the same expression construct produces a linear DNA fragment which comprises the homologous sequences on either side of the selectable marker. The homologous or recognition sequences serve as 'landing pads' for integration of a gene of interest with compatible recognition sequence flanks. There are several recognition sequences that are known in the art to direct transgenes into specific genomic locations, for example DNA flanked by lox sites oriented in the same direction is deleted, whereas DNA flanked by lox sites oriented in the opposite direction is inverted upon recombination mediated by Cre-recombinase. Other recognition sites include FLP-recombination target sites and 'safe harbor' recognition sequences as described herein (above) can be introduced flanked with gRNA target sequences. The gRNA directed Cas9 introduces double stranded breaks in the genomic locus as well as cuts the expression vector at the gRNA target sites allowing efficient integration of the linearized fragment with flanking recognition sequences into a genomic locus by non-homologous recombination events. The resulting cells have the optional ability to have DNA reproducibly and repetitively inserted into and/or recovered from the host cell and/or organism.

A "Selectable marker" refers to a DNA segment that allows one to select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions. Examples of Selectable markers include but are not limited to: (1) DNA segments that encode products which provide resistance against otherwise toxic compounds (e.g., antibiotics); (2) DNA segments that encode products which are otherwise lacking in the recipient cell (e.g., tRNA genes, auxotrophic markers); (3) DNA segments that encode products which suppress the activity of a gene product; (4) DNA segments that encode products which can be readily identified (e.g., phenotypic markers such as beta-galactosidase, green fluorescent protein (GFP), and cell surface proteins); (5) DNA segments that bind products which are otherwise detrimental to cell survival and/or function; (6) DNA segments that otherwise inhibit the activity of any of the DNA segments described in Nos. 1-5 above (e.g., antisense oligonucleotides); (7) DNA segments that bind products that modify a substrate (e.g. restriction endonucleases); (8) DNA segments that can be used to isolate a desired molecule (e.g. specific protein binding sites); (9) DNA segments that encode a specific nucleotide sequence which can be otherwise non-functional (e.g., for PCR amplification of subpopulations of molecules); and/or (10) DNA segments, which when absent, directly or indirectly confer sensitivity to particular compounds.

In another embodiment, the overall rates of efficiency of the Cas9 system may be aided indirectly through proteins such as bacterial RecA or its mammalian homolog Rad51 which have been shown to increase the rates of homologous recombination of artificial targeting constructs. The protein may be expressed in the same cell as the Cas9 through separate transduction, or as a direct fusion to Cas9. Expression of RecA or its mammalian homolog Rad51 may also be translationally coupled to Cas9, Cas9n or dCas9 via coupling elements, for example an IRES or 2A/CHYSEL element.

Additionally, the RecA or its mammalian homolog Rad51 may be linked to a localization signal, for example a nuclear localization signal to facilitate transport and localization to the nucleus and site of genome modification. Nuclear localization signals (NLS) are stretches of residues in proteins that mediate their import into the nucleus. A NLS peptide can direct a protein to be imported into the nucleus by acting as a signal for anchoring proteins to specialized transporter molecules found on the pore complex or in the cytoplasm.

Construction of gRNA Libraries

Figure 4A:
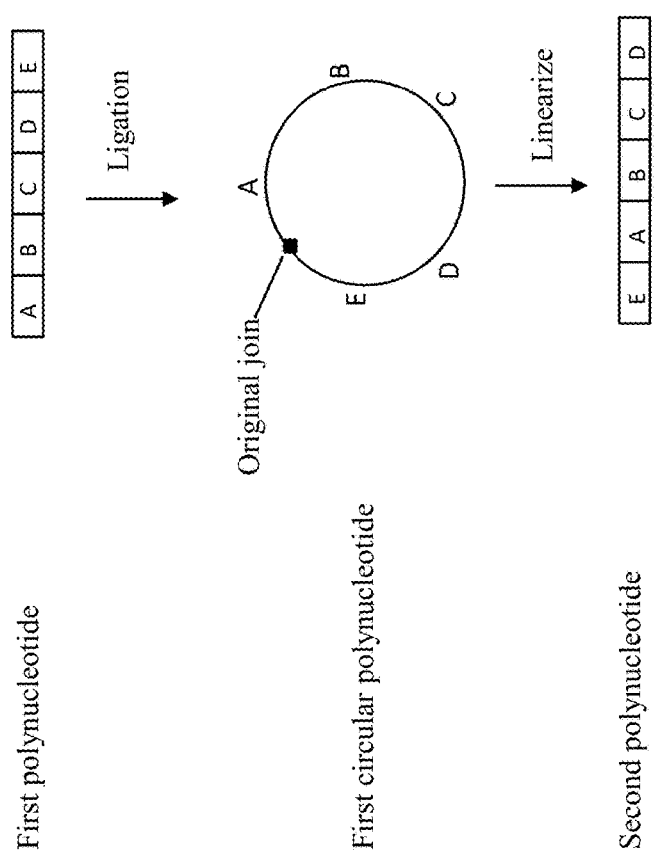
FIG. 4A: shows construction of a library of linked polynucleotides in a single step wherein each of the linked polynucleotides are transcribed from a single construct. These methods comprise producing a first linear polynucleotide, circularizing the first linear polynucleotide, and then linearizing the circular polynucleotide at a position other than the original join to produce a second linear polynucleotide. By doing so, sequences that were close together in the first linear polynucleotide may be far apart in the second linear polynucleotide. Such a procedure also permutates the sequences in the polynucleotide, for example sequence elements may be ordered A, B, C, D, E in the first linear polynucleotide, while the same elements are ordered B, C, D, E, A in the second linear polynucleotide. In some embodiments sequences A and B are more than 100 nucleotides further apart in the second linear polynucleotide than in the first, in some embodiments sequences A and B are more than 200 nucleotides further apart in the second linear polynucleotide than in the first, in some embodiments sequences A and B are more than 300 nucleotides further apart in the second linear polynucleotide than in the first, in some embodiments sequences A and B are more than 400 nucleotides further apart in the second linear polynucleotide than in the first.
Figure 4B:
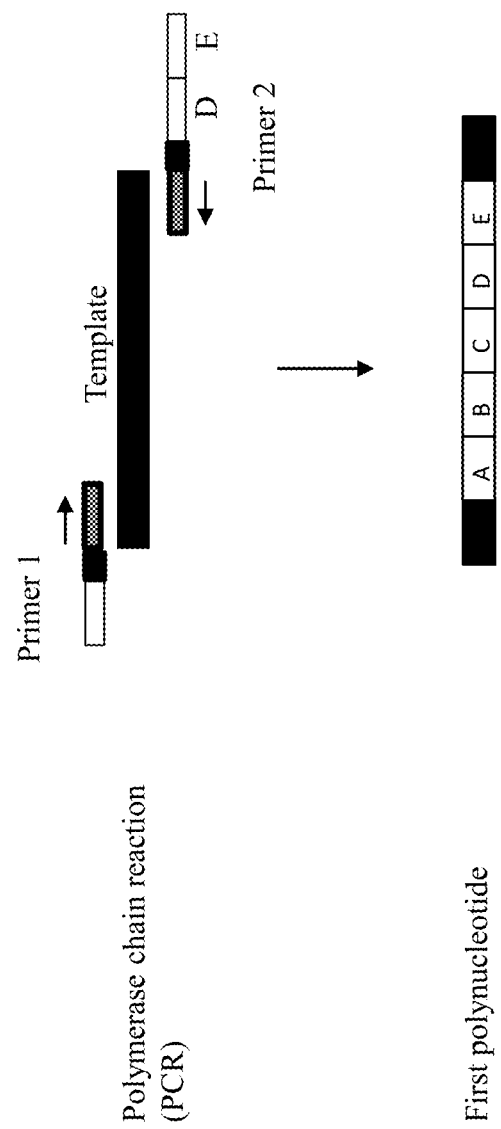
FIG. 4B: shows one method for generation of a first polynucleotide by polymerase chain reaction (PCR) wherein sequences A and B are chemically synthesized on the same oligonucleotide. In some embodiments, sequences A and B are chemically synthesized on the same oligonucleotide; in some embodiments the first linear polynucleotide is made using an oligonucleotide comprising sequences A and B as a primer in the polymerase chain reaction.

It is frequently advantageous to link the expression of gRNAs so that two or more specific gRNAs may be expressed in the same cell at the same time. For example, it may be desirable to target two or more specific genes within the same cell using a construct expressing a cas9 nuclease that causes double-stranded breaks. In another application, it is frequently desirable to express two gRNAs targeted to the same gene using a cas9 nuclease that breaks only 1 strand of the genome (a Cas9 nickase). In these cases, a useful genome editing event only occurs if the two gRNAs can be expressed from the same construct. Methods to construct the library of linked gRNAs in a single step wherein each of the linked gRNAs are transcribed from a single construct are another aspect of this invention. These methods comprise producing a first linear polynucleotide, circularizing the first linear polynucleotide, and then linearizing the circular polynucleotide at a position other than the original join to produce a second linear polynucleotide. By doing so, sequences that were close together in the first linear polynucleotide may be far apart in the second linear polynucleotide. Such a procedure also permutates the sequences in the polynucleotide, for example sequence elements may be ordered A, B, C, D, E in the first linear polynucleotide, while the same elements are ordered B, C, D, E, A in the second linear polynucleotide (FIG. 4A). In some embodiments sequences A and B are more than 100 nucleotides further apart in the second linear polynucleotide than in the first, in some embodiments sequences A and B are more than 200 nucleotides further apart in the second linear polynucleotide than in the first, in some embodiments sequences A and B are more than 300 nucleotides further apart in the second linear polynucleotide than in the first, in some embodiments sequences A and B are more than 400 nucleotides further apart in the second linear polynucleotide than in the first. In some embodiments, sequences A and B are chemically synthesized on the same oligonucleotide; in some embodiments the first linear polynucleotide is made using an oligonucleotide comprising sequences A and B as a primer in the polymerase chain reaction (FIG. 4B).

Figure 5A:
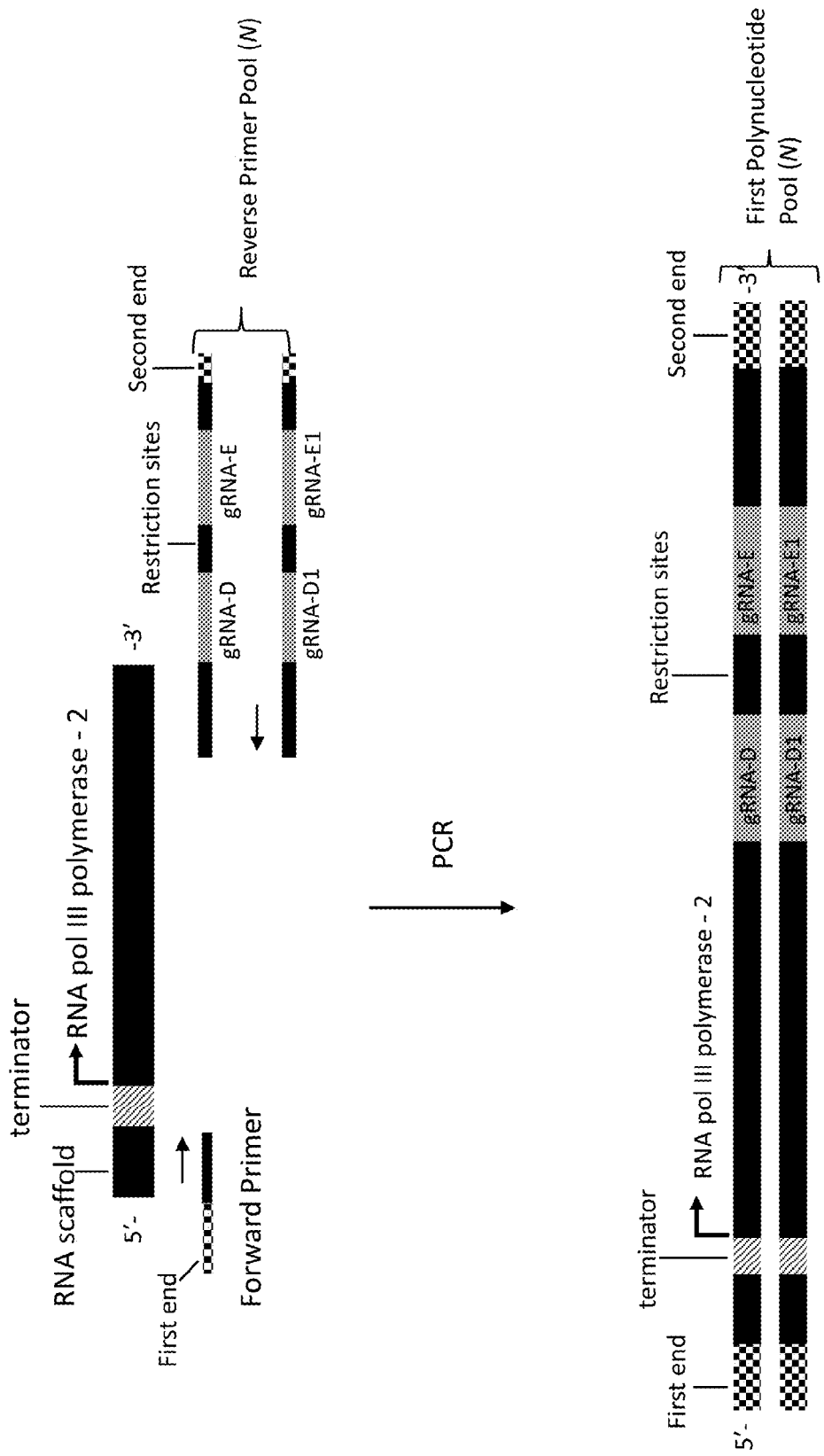
FIG. 5A: shows one method of generating a linked gRNA library using PCR amplification of a spacer oligonucleotidetemplate. The spacer oligonucleotide contains from left to right a RNA scaffold sequence, a terminator, and an RNA pol III promoter. A forward primer has a first end extending beyond the template and a segment that can duplex with and prime amplification from the 5' end of template. A pool of reverse primers each has the following components from right to left as shown, a second end segment, different linked gRNAs separated by a sequence fragment with third and fourth restriction sites and a segment that can duplex with and prime replication from the 3' end of the template. The resulting first polynucleotide pool has a first end, RNA scaffold sequences, a terminator, RNA pol III promoter, second gRNA, first gRNA and a second end that is compatible to the first end.
Figure 5B:
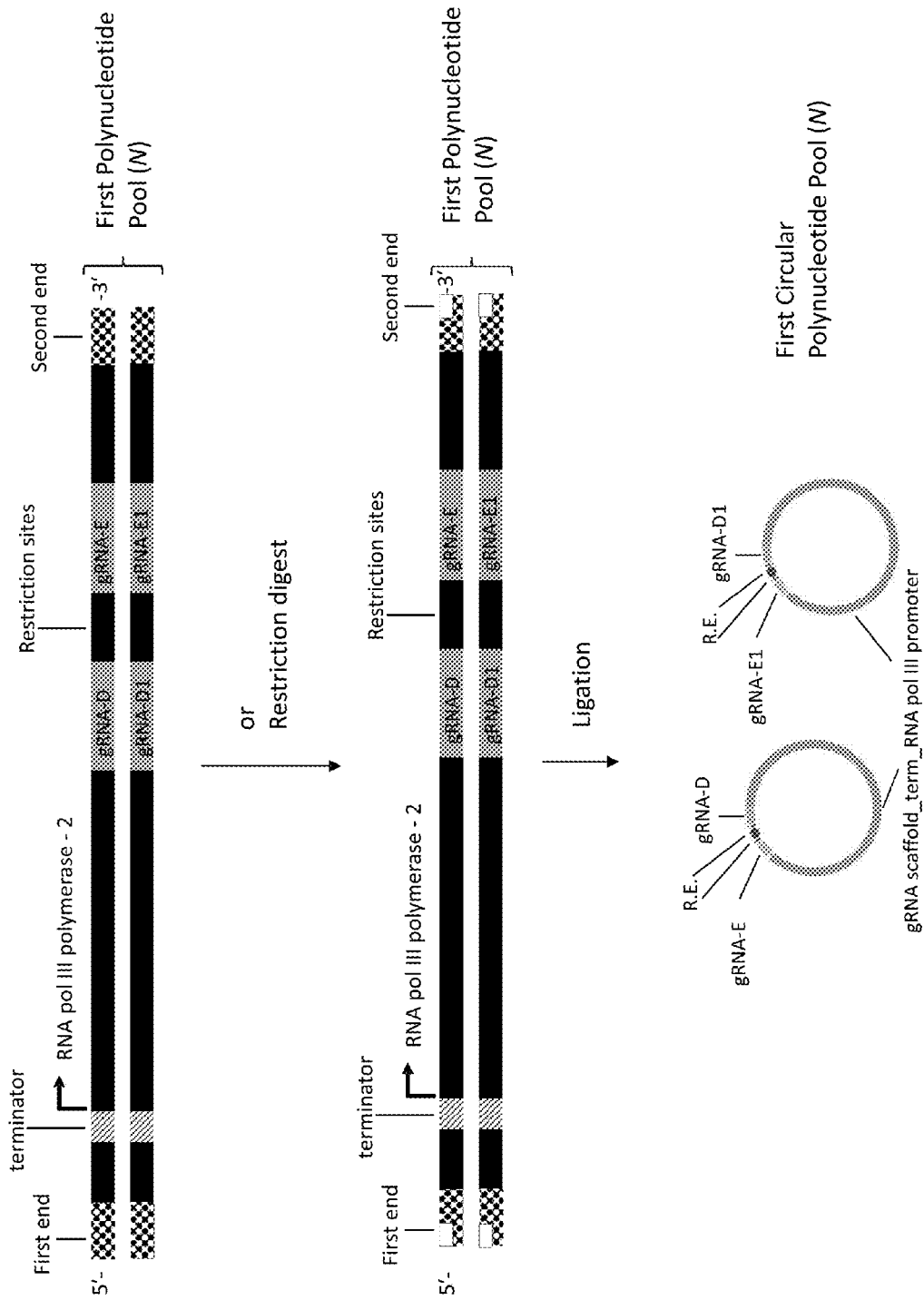
FIG. 5B: shows the first polynucleotide pool generated in FIG. 5A (above) with blunt first and second ends or cleaved to generate compatible first and second ends. Upon ligation of the compatible first and second ends, the polynucleotides circularize to generate first circular polynucleotide pools with linked gRNAs separated by a nucleotide sequence comprising third and fourth restriction sites and the RNA scaffold sequence, terminator and RNA pol III promoter regions. In preferred embodiments the cloning is performed in a single reaction comprising restriction endonuclease and DNA ligase.
Figure 5C:
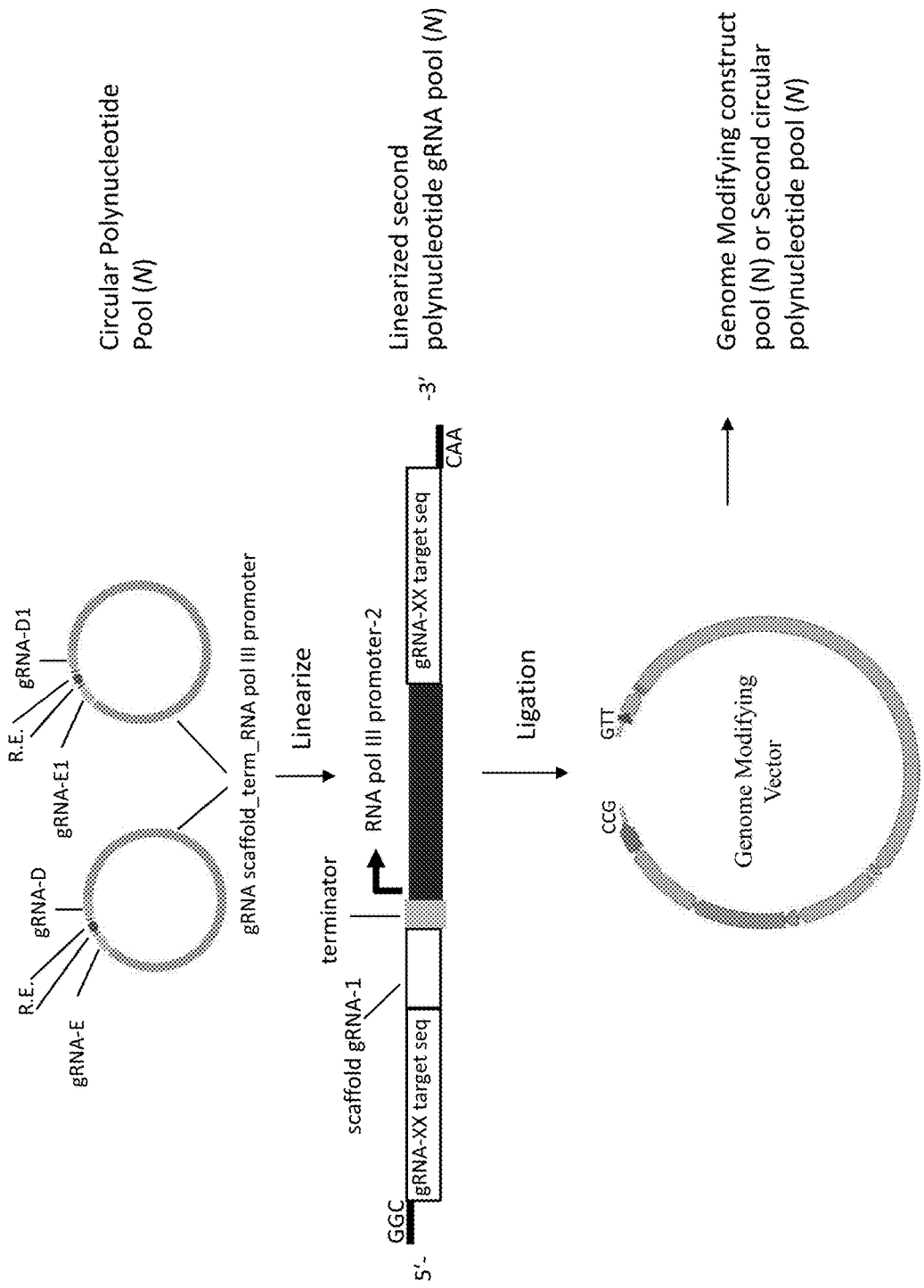
FIG. 5C: shows cleavage of the circularized linked gRNA pool with a second restriction endonuclease. The sequence separating the linked gRNAs is cleaved at the third and fourth restriction sites to generate overhangs 5'-CGG-3' and 5'-CAA-3' that are compatible with the linearized genome modifying vector with 5'-CCG-3' and 5'-GTT-3' overhangs. Ligation of this pool of linear second polynucleotides into the genome modifying vector generates a genome modifying construct pool or second circular polynucleotide pool with linked gRNAs, each operably linked to a RNA pol III promoter and transcribed from the same construct. In preferred embodiments the cloning is performed in a single reaction comprising restriction endonuclease and DNA ligase. In some embodiments the cas9 gene in the genome modifying vector encodes a cas9 nickase (SEQ ID NO: 10) or dCas9. In some embodiments the vector does not encode Cas9. In some embodiments, each of the linked gRNAs targets different genomic loci. In some embodiments, each of the linked gRNAs targets the same genomic locus.

In some embodiments, a library of two or more linked gRNA inserts is generated by PCR amplification using a template with a segment encoding a scaffold RNA, terminator and a RNA pol III promoter. One method used to construct the library of linked gRNAs wherein each of the linked gRNAs is transcribed from a single genome modifying construct is another aspect of this invention. The method comprises designing primers with blunt ends or compatible restriction sites (for example, six cutters, type II cutters and the like). In a preferred embodiment, primers are designed with a first restriction site at the first end (5' end) of the forward primer and a second restriction site at the second end (3' end) of the reverse primer to generate compatible overhangs at the first and second ends. In a preferred embodiment, the first and second restriction sites are type IIs enzyme, BsaI. In preferred embodiments, the reverse primer comprises the two linked gRNAs separated by third and fourth restriction sites that are different from the first and second restriction sites, for example SapI sites placed in opposite orientation and that create compatible overhangs to the ends of the genome modifying vector. Multiple (at least 2, at least 5, at least 10, at least 15, at least 20, at least 25, at least 30, at least 40, at least 60, at least 100, at least 200, at least 500, at least 800, at least 2000, at least 5000, at least 8000, at least 10000 or more) reverse primers comprising distinct linked pairs of gRNAs are used along with a single forward primer to PCR amplify off a template (SEQ ID NO: 12) with part of a chimeric tracr sequence or gRNA scaffold (SEQ ID NO: 204), terminator and a RNA pol III promoter (FIG. 5A). PCR Amplification generates a population of first polynucleotides with a first restriction site at the first 5' end, scaffold RNA sequence, terminator, RNA pol III promoter, linked gRNAs separated by a sequence comprising third and fourth restriction sites, followed by the second restriction site at the second or 3' end that creates compatible overhangs to the first restriction site, for example, in a preferred embodiment, type IIs enzyme BsaI is used to create compatible four base pair overhangs at the first and second ends. A ligation step creates first circular polynucleotides by ligation of the first and second ends keeping the linked gRNAs together on the same first circular polynucleotide (FIG. 5B). Methods such as polymerase chain reaction (PCR) or restriction endonuclease cleavage or rolling circle amplification (RCA) followed by restriction endonuclease cleavage can be used to linearize the circular polypeptide to generate linearized second polypeptide. In a preferred embodiment, a second restriction with a second restriction enzyme cuts between the two linked gRNAs to form a linearized second polynucleotide with compatible overhangs to the genome modifying vector with Cas9, for example, type IIs enzyme SapI is used to generate overhangs 5'-CGG-3' at the 5' end and 5'-CAA-3' at the 3' end that are compatible with the genome modifying vector ends (FIG. 5C). A library of linearized second polynucleotides so generated can be cloned into a genome modifying vector expressing Cas9 to create a library of genome modifying constructs with distinct linked gRNAs, each operably linked to a RNA pol III promoter for genome modification (FIG. 5C) as described herein (above). In preferred embodiments the cloning is performed in a single reaction comprising restriction endonuclease and DNA ligase. In some embodiments the Cas9 gene encodes a Cas9 nickase or dCas9. In some embodiments the vector does not encode Cas9. In preferred embodiments, the restriction enzymes are type IIs endonucleases. Other embodiments include restriction enzymes that are six cutters. In some embodiments, the first linear polynucleotide is circularized by ligation independent methods or recombination based methods. In some embodiments, the first and second ends of the first linear polynucleotide are overlapping ends.

In some embodiments, a library of oligonucleotides including paired segments encoding paired guide RNA's have compatible ends to a vector are inserted into the vector in a simple cloning step to generate a plurality of circular nucleic acid molecules encoding different pairs of linked guide RNAs. The circular nucleic acids are then linearized in at least one site between the DNA encoding the paired guide RNAs to allow insertion of a spacer oligonucleotide (SEQ ID NO: 12) with compatible ends to the ends generated between the DNA encoding the paired guide RNAs such that each of the guide RNAs is in operable linkage to a promoter, one from the vector and the other promoter from the spacer. The spacer and vector can include additional elements in similar manner to described for insertion of a nucleic acid formed by template-directed assembly. For example, the spacer can include a transcriptional terminator and encode an RNA scaffold (SEQ ID NO: 204), as can the vector. Accordingly, one guide RNA operably linked to a scaffold RNA encoded by the vector and expressed from a promoter on the vector is transcriptionally terminated at the terminator provided by the spacer. The other guide RNA operably linked to a scaffold RNA encoded by the spacer is expressed from a promoter on the spacer and transcriptionally terminated at a terminator in the vector. Such methods can be performed in parallel with large numbers of different paired nucleic acids being inserted into the vector, and each vector then being supplied with the same spacer fragment supplying the same elements (e.g., terminator, promoter and RNA scaffold).

A library of linked gRNA constructs may comprise about at least 50 different constructs, about at least 200, different constructs, about at least 500 different constructs, about at least 1,000 different constructs, about at least 2,000 different constructs, about at least 5,000 different constructs, about at least 7,000 different constructs, about at least 10,000 different constructs, or about at least 20,000 different constructs. In some embodiments at least 30% of the gRNAs in the library are linked in a pre-determined way, in some embodiments at least 40% of the gRNAs in the library are linked in a pre-determined way, in some embodiments at least 50% of the gRNAs in the library are linked in a pre-determined way, in some embodiments at least 60% of the gRNAs in the library are linked in a pre-determined way, in some embodiments at least 70% of the gRNAs in the library are linked in a pre-determined way, in some embodiments at least 80% of the gRNAs in the library are linked in a pre-determined way. In some embodiments the linked gRNAs are pairs of gRNAs targeted to different strands of the same gene such that nicking by a Cas9 nickase that is targeted by the linked gRNA pair causes a double-stranded break at the genomic locus.

In some embodiments, the library of distinct linked gRNAs is directed to multiple genomic loci. In other embodiments, the library of distinct linked gRNA pairs is directed to linked functional groups of genetic loci, for example, a library of distinct linked gRNA pairs directed to a family of kinases, GPCRs, phosphatases, proteases, receptors as described herein. A targeted library so generated is advantageous for creating cell lines with desirable properties, for example enhanced expression characteristics, superior attachment properties, faster propagation or improved growth characteristics and; to determine functional effects of genome modifications associated with a specific class of targets.

In some embodiments, the library of two or more linked gRNAs is targeted to the first exon of a genomic locus that belongs to functionally related families of genes, for example the first exon of a family of kinases, the first exon of a family of GPCRs, the first exon of a family of phosphatases, the first exon of a family of proteases, the first exon of a family of receptors and the like. In some embodiments, each of the linked gRNAs is directed to different functionally linked genomic loci of interest. In other embodiments, each of the gRNAs in the linked pair is directed to the same genomic locus.

In other embodiments, a library of two or more linked polynucleotides other than gRNA can be generated using the method described above comprising two or more respective linked sub-sequences, wherein the linkage of the sub-sequences is pre-determined. In some embodiments, the linked polynucleotides are transcription units. Other embodiments using different type IIs enzymes or other restriction enzymes are expressly contemplated. In some embodiments, the linked polynucleotides are separated by a sequence comprising of restriction sites. As described in the method above, the circularized polynucleotide with the two or more linked polynucleotide sub-sequences can be linearized to generate the first linear polynucleotide by i) restriction endonuclease cleavage; ii) by PCR amplification or; iii) by rolling circle amplification (RCA) followed by restriction endonuclease cleavage. Other embodiments using different type IIs enzymes or other restriction enzymes are expressly contemplated.

Kits

A kit comprising a library of linked gRNAs as described herein and reagents' including buffers, restriction endonucleases is another embodiment. In some embodiments, the kit comprises a template sequence, a primer, restriction endonucleases, buffers and instructions for design of oligonucleotides with two or more linked gRNAs and instructions for generating a library comprising two or more linked gRNAs.

A preferred kit supplies a user with components of the vector and methods described herein that are constant independent of guide RNAs or (other linked nucleic acids being screened). These components can include a) a vector comprising a promoter transcribed by a RNA polymerase and a nucleic acid sequence encoding a Cas9 nuclease operably linked to a promoter (e.g that of having SEQ ID NO: 10) and b) a spacer oligonucleotide comprising a second promoter transcribed by a RNA polymerase (e.g that of having SEQ ID NO: 12). A use of the kit uses the spacer oligonucleotide in an assembly reaction to generate a linearized nucleic acid including paired nucleic acid segments as previously described, and such linearized nucleic acid is then inserted into the vector. Preferably, the vector can be linearized to have compatible ends for insertion of a nucleic acid fragment comprising the spacer oligonucleotide flanked by paired nucleic acid fragments, whereby one of the pair segments is expressible from the polymerase promoter of the spacer nucleotide and the other of the paired segments is expressible from the polymerase promoter of the spacer. In one embodiment, the paired segments encode guide RNAs, the spacer oligonucleotide comprises the second RNA polymerase promoter with a transcriptional terminator and a segment encoding a scaffold RNA (SEQ ID NO: 204) upstream of the RNA polymerase promoter. The vector can have compatible ends for insertion of the nucleic acid fragment wherein one guide RNA is in operable linkage with the pol promoter of the vector and guide RNA of the spacer oligonucleotide and the other guide RNA is in operable linkage with the pol promoter on the spacer oligonucleotide and scaffold RNA of the vector. The kit can also include a primer for priming template directed synthesis from one end of the spacer oligonucleotide as described above. In some embodiments the Cas9 is a mutant Cas9 with nickase activity. In other embodiments the Cas9 is a mutant Cas9 with lowered or no activity (dCas9). In some embodiments, expression of Cas9 can be monitored by a fluorescent reporter coupled to Cas9 via coupling elements selected from IRES and CHYSEL elements. In some embodiments, the RNA polymerase III promoters are selected from U6, H1 and 7SK or prokaryotic promoters T5, T7 and SP6. In some embodiments, the RNA polymerase promoters are selected from U6 variants (SEQ ID NOS: 1-5). In some embodiments, the RNA polymerase promoters are the same, in some other embodiments the RNA polymerase promoters are different. In some preferred embodiments, the RNA polymerase III promoters include U6.1 (SEQ ID NO: 3) and U6-8cc (SEQ ID NO: 1). A kit can also include one or more of type IIs restriction endonucleases, ligase and buffers to facilitate library construction.

EXAMPLES

The following examples are intended to illustrate the methods, compositions and kits disclosed herein and should not be construed as limiting in any way. Various equivalents will be apparent from the following examples; such equivalents are also contemplated to be part of the invention disclosed herein.

Expression of Two gRNAs (Guide RNAs) in a Single Expression Vector Construct

We show expression of two gRNAs and Cas9n in a single construct is more efficient and gave a higher frequency of indel formation than co-transfection with constructs expressing single gRNAs and Cas9n. Additionally, expression of the D10A nickase mutant form of Cas9 nuclease (Cas9n), with expression of two offset gRNAs complementary to opposite strands of the target site gave comparable or higher frequencies of indel formation compared to wild type Cas9 with a single gRNA.

gRNAs were designed as a offset pair complementary to opposite strands of the EMX-1 locus in the genome and adjacent to a PAM sequence that direct a pair of Cas9 nucleases to opposite strands of the target locus to cause nicking and double stranded breaks (DSBs) (SEQ ID NOS: 6-9). A construct expressing a pair of offset gRNAs, 1a (SEQ ID NO: 6) and 1b (SEQ ID NO: 7) directed by two U6 variants of RNA pol III promoter U6.1 (SEQ ID NO: 3) and 8cc (SEQ ID NO: 1) in vector (SEQ ID NO: 10) with a CMV promoter directing expression of Cas9N coupled via 2A element to a fluorescent reporter in a single vector construct were made; a construct expressing a pair of offset gRNAs, emx-1-1 (SEQ ID NO: 8) and emx-1-9 (SEQ ID NO: 9) directed by two U6 variants of RNA pol III promoter U6.1 (SEQ ID NO: 3) and 9cc (SEQ ID NO: 2) in vector (SEQ ID NO: 10) with a CMV promoter directing expression of Cas9N coupled via 2A element to a fluorescent reporter in a single vector construct were made; additionally constructs with a single RNA pol III promoter U6.1 (SEQ ID NO: 3) expressing single gRNA complementary to the top or bottom strand of targeted EMX-1 locus in vector (SEQ ID NO: 10) expressing Cas9N and coupled via 2A element to a fluorescent reporter were made and co-transfected in parallel.

HEK 293a cells (from ATCC) were grown in EMEM (from ATCC)+10% FBS (from ATCC)+1% Penicillin-streptomycin (from ATCC) at 37° C., 5% $CO_2$ to 80% confluence, 1E+05 cells were plated in 24-well tissue culture plates and incubated at 37° C., 5% $CO_2$ for 24 hours prior to transfection. Each transfection used 0.5 µg DNA with Lipofectamine 2000 as per manufacturer's protocol. For constructs expressing single gRNAs, two plasmids were co-transfected using 0.25 µg DNA per plasmid for a total DNA concentration of 0.5 µg. Cells were harvested 72 hours post transfection and genomic DNA extracted from cells using DNeasy Blood and Tissue Kit (Qiagen, Cat. No. 69504) as per manufacturer's protocol. Extracted genomic DNA was amplified at the EMX-1 locus using the following PCR primers:

For SEQ ID NOS: 6 and 7, the following PCR primers were used

```
SeqF2:      CTCATTTGCATGTCCCAC
SeqR2:      TTGGGAGAATTTCATGCAACG
```

For SEQ ID NOS: 8 and 9, the following PCR primers were used:

```
SeqF3:      TTGCATACGACCATTTCCA
SeqR3:      CTATTCCAATGTGTAATGCAACT
```

PCR products were sequenced and analysed for indel frequencies using the primers shown above.

Upon transfection and expression of the offset pair of gRNAs and Cas9n, binding of the offset pair of gRNAs complementary to opposite strands of the EMX-1 target site direct Cas9N to cause single stranded breaks in opposite strands. Nicking of both DNA strands by a pair of Cas9 nickases causes site-specific double stand breaks (DSBs) and NHEJ (non-homologous end joining) leading to indels.

Table 1 shows the indel frequencies observed for co-transfected constructs expressing single gRNAs and transfection with a single construct expressing two gRNAs transcriptionally controlled by RNA pol III promoters U6.1 (SEQ ID NO: 3) and 8cc (SEQ ID NO: 1) or U6.1 and 9cc (SEQ ID NO: 2). Single gRNA expressing constructs with U6.1 RNA pol III promoter and Cas9N were transfected as background controls. We observed an indel frequency of 51% in cells transfected with gRNAs 1a and 1b (targeting the EMX-1 locus) expressed in a single construct with two RNA pol III promoters U6.1 and U6-8cc compared to a 40% indel frequency in singly expressing co-transfected gRNA constructs. The RNA pol III promoter combination of U6.1 and U6-8cc gave the highest indel frequency of 51% compared to 24% indel frequency observed for U6.1 and U6-9cc RNA pol III promoter combination. Similarly, the RNA pol III promoter combination of U6.1 and U6-8cc controlling expression of two gRNAs emx1-1 and emx1-9 (targeting the EMX-1 locus) shows an indel frequency of 47%, that is higher than the 19% indel frequency with U6.1 and U6-9cc RNA pol III promoter combination or the 35% indel frequency observed upon co-transfection with the two singly expressed emx1-1 and emx1-9 gRNA constructs.

TABLE 1

| Replicate | Construct | Promoter | Cas9 | RNA pol III -1 | RNA pol III -2 | target gRNA 1 | target gRNA 2 | No. seq | # indel | Frequency (%) | Mean Frequency |
|---|---|---|---|---|---|---|---|---|---|---|---|
| 1 | Co-transf SEQ ID NO: 6 and 7 | CMV | D10A | U6.1 | | 1a | 1b | 19 | 3 | 16 | 40 |
| 2 | | CMV | D10A | U6.1 | | 1a | 1b | 18 | 8 | 44 | |
| 3 | | CMV | D10A | U6.1 | | 1a | 1b | 18 | 10 | 56 | |
| 4 | | CMV | D10A | U6.1 | | 1a | 1b | 18 | 8 | 44 | |
| 1 | Single construct, tandem (SEQ ID NO: 6 and 7 in SEQ ID NO: 10) | CMV | D10A | U6.1 | U6-8cc | 1a | 1b | 18 | 9 | 50 | 51 |
| 2 | | CMV | D10A | U6.1 | U6-8cc | 1a | 1b | 17 | 9 | 53 | |
| 1 | Single construct, tandem (SEQ ID NOS: 6 and 7 in SEQ ID NO: 10) | CMV | D10A | U6.1 | U6-9cc | 1a | 1b | 19 | 5 | 26 | 24 |
| 2 | | CMV | D10A | U6.1 | U6-9cc | 1a | 1b | 19 | 4 | 21 | |
| 1 | Co-transf SEQ ID NOS: 8 and 9 | CMV | D10A | U6.1 | | 1_1 | 1_9 | 20 | 6 | 30 | 35 |
| 2 | | CMV | D10A | U6.1 | | 1_1 | 1_9 | 17 | 4 | 24 | |
| 3 | | CMV | D10A | U6.1 | | 1_1 | 1_9 | 19 | 11 | 58 | |
| 4 | | CMV | D10A | U6.1 | | 1_1 | 1_9 | 16 | 4 | 25 | |
| 1 | Single construct, tandem (SEQ ID NOS: 8 and 9 in SEQ ID NO: 10) | CMV | D10A | U6.1 | U6-8cc | 1_1 | 1_9 | 19 | 10 | 53 | 47 |
| 2 | | CMV | D10A | U6.1 | U6-8cc | 1_1 | 1_9 | 19 | 8 | 42 | |
| 1 | Single construct, tandem (SEQ ID NOS: 8 and 9 in SEQ ID NO: 10) | CMV | D10A | U6.1 | U6-9cc | 1_1 | 1_9 | 20 | 2 | 10 | 19 |
| 2 | | CMV | D10A | U6.1 | U6-9cc | 1_1 | 1_9 | 16 | 5 | 31 | |

Transfection with single gRNA and Cas9n expressing constructs showed a zero percent indel frequency (data not shown). Expression of the Cas9n and transfection efficiencies were monitored by a fluorescent reporter, DasherGFP in the dual gRNA expressing constructs. Constructs used for co-transfection had different fluorescent reporters, with DasherGFP (SEQ ID NO: 10) or PaprikaRFP (SEQ ID NO: 11) to monitor percentage of transfection of both constructs per cell. Transfection efficiencies for the single vector construct expressing two gRNAs and co-transfection with singly expressing gRNA vectors showed similar transfection efficiencies (data not shown).

Transfection with a single gRNA and Cas9 expressing construct showed an indel frequency of 36% or 24% compared to 51% or 47% indel frequency observed upon transfection with two sets of dual expressing gRNAs directing Cas9n to different regions within the EMX-1 locus.

We have shown that a paired nickase strategy that combines the D10A mutant of Cas9 (Cas9n) with a pair of offset gRNAs complementary to the opposite strands of the target site expressed in a single vector construct shows nicking of both DNA strands by a pair of Cas9 nickases leading to site-specific double stand breaks (DSBs) and NHEJ (non-homologous end joining) as seen by the frequency of indel formation. This indel frequency is more efficient and more reproducible compared to indel frequency observed by co-transfection of gRNAs expressed from two vector constructs. This is probably because it avoids the variability of different transfection efficiencies for a pair of co-transfected plasmids. Additionally, the U6.1 and U6-8cc RNA pol III promoters in a single construct are a preferred embodiment.

Construction of a Library of Linked gRNA Pairs Targeting Different Regions of a Genomic Locus A library of linked gRNAs was created using the method described herein. A forward primer, a pool of three reverse primers and template are shown below:

```
Forward primer (SEQ ID NO: 13):
5'-
GATGGGATGGTCTCAGTTTTAGAGCTAGAAATAGCAAGTTAAAATAAGGC

TAG-3'

Reverse primers:
gRNA pair 1: EMX1-9-R (SEQ ID NO: 14)
5'-
AGGGCACCGGTCTCTAAACTTCTTCTTCTGCTCGGACTCCGGTGAAGAGC

GCTCTTCTAACGAGGACAAAGTACAAACGGCCGGTGAGAAGAAGTCACCC

ACAG-3' gRNA pair 2: PGNL-EMX1-20-22 (SEQ ID NO: 15)
5'-
AGGGCACCGGTCTCTAAACATGGGGAGGACATCGATGTCCGGTGAAGAGC

GCTCTTCTAACTCGTGGGTTTGTGGTTGCCCCGGTGAGAAGAAGTCACCC

ACAG-3' gRNA pair 3: PGNL-EMX1-15-21 (SEQ ID NO: 16)
5'-
AGGGCACCGGTCTCTAAACTCACATCAACCGGTGGCGCACGGTGAAGAGC

GCTCTTCTAACCCCTAGTCATTGGAGGTGACCGGTGAGAAGAAGTCACCC

ACAG-3'
```

The forward and reverse primers with linked gRNA pairs targeting different regions of the EMX-1 genomic locus (shown above) were used to PCR amplify off a template (SEQ ID NO: 12) with sRNA (SEQ ID NO: 204), terminator and RNA pol III promoter to create a first polynucleotide pool with a first end, a gRNA scaffold region (sRNA), terminator, RNA pol III promoter (SEQ ID NO: 1), two linked gRNAs separated by a polynucleotide sequence with third and fourth restriction sites and a second end (FIG. 5A). The three reverse primers incorporate three distinct linked gRNA pairs that are targeted to the EMX-1 genomic locus, each linked gRNA pair targeting different regions of the EMX-1 genomic locus.

A 100 µl PCR reaction was set up with 20 ng (0.2 ng/µl) template, mixed with 1 µM each of forward primer and reverse primer pool and amplified in a thermal cycler as follows: 96° C. for 2 minutes, 25 cycles of 96° C. 30 seconds, 60° C. 30 seconds and 72° C. for 30 seconds followed by an extension at 72° C. for 1 minute, hold at 10° C. PCR product was purified with the AccuPrep® PCR purification kit spin columns (Bioneer) to isolate band of expected size. 25 ng of purified PCR product was cleaved with type IIs restriction endonuclease BsaI to generate first and second compatible ends. Ligation with T4 DNA ligase joins the first and second ends to generate first circularized polynucleotides (FIG. 5B). Restriction digest and ligation were carried out in the same reaction in a 100 µl reaction volume with 1 µl BsaI, 1 µl T4 DNA ligase and 10 µl Electra buffer (Universal buffer (New England Biolabs)+ATP mix from DNA2.0) at room temperature for 1 hour. Cleaved PCR product was precipitated with 1/10 volume 3M NaOAc, 1 volume isopropanol and incubated at −20° C. for 1 hour. Samples were centrifuged at 12000×g for 30 minutes and DNA pellet rinsed with 500 µl 70% ethanol. Centrifugation was repeated at 12000×g and supernatant discarded. DNA pellet was air dried and then resuspended in 10 µl sterile water.

A second restriction endonuclease cleavage and ligation was carried out with type IIs restriction endonuclease SapI to generate second polynucleotides with third and fourth ends that are compatible with the genome modifying vector (SEQ ID NO: 10) as shown in FIG. 5C. 7 µl of precipitated and resuspended first circularized polynucleotide from above was mixed with 1 µl Electra Enzyme mix (SapI and T4 DNA ligase mix, cat # EKT-02 kit, DNA2.0), 1 µl Electra buffer mix (with 10×Universal buffer (New England Biolabs)+10 mM ATP, cat # EKT-02 kit, DNA2.0)), 1 µl of linearized 20 ng/µl genome modifying vector pD1401-AD (SEQ ID NO: 10) from DNA2.0. Reaction was incubated at room temperature for 1 hour. Transformed the entire 10 µl into competent DH10B cells and plated on to LB plates with 100 µg/ml kanamycin. 18 transformants were picked, plasmids isolated from cultures and analyzed by sequencing.

We observed a ratio of 16:1:1 for the three linked gRNA pairs showing that all three linked gRNA pairs were incorporated and represented at least once in this library. No concatamers or unintended linked gRNA pairs were observed. Further optimization to generate larger libraries and to increase the incorporation efficiency of linked gRNA pairs is expressly contemplated. This demonstrates that it is possible to generate linked gRNA or other linked polynucleotide fragments using the method described herein.

Construction of a Library of Linked Unique gRNA Pairs

A pool of 190 reverse primers comprising the two linked guide RNAs (SEQ ID NOS: 14-204), a forward primer (SEQ ID NO: 13) and template comprising the sRNA (SEQ ID NO: 204), promoter and terminator (SEQ ID NO: 12) were used to generate a 190 member library of linked gRNA pairs, each pair coding for a unique pair of offset gRNAs, using the method described herein.

The forward and reverse primers with unique linked gRNA pairs (SEQ ID NOS: 14-204) were used to PCR amplify off a spacer template (SEQ ID NO: 12) with sRNA (SEQ ID NO: 204), terminator and RNA pol III promoter to create a first polynucleotide pool with a first end, a gRNA scaffold region (sRNA), terminator, RNA pol III promoter (SEQ ID NO: 1), two linked gRNAs separated by a polynucleotide sequence with third and fourth restriction sites and a second end (FIG. 5A). The 190 reverse primers incorporate 190 distinct linked gRNA pairs.

A 100 µl PCR reaction was set up with 20 ng (0.2 ng/µl) template SEQ ID NO: 12), mixed with 1 µM each of forward primer and reverse primer pool and amplified in a thermal cycler as follows: 95° C. for 2 minutes, 25 cycles of 95° C. 30 seconds, 60° C. 30 seconds and 72° C. for 20 seconds followed by an extension at 72° C. for 2 minute, hold at 10° C. PCR product was cleaved with type IIs restriction endonuclease BsaI in a 120 µl reaction volume with 6 µl BsaI (120 units) to generate first and second compatible ends. Digested PCR product was gel purified with the AccuPrep® PCR purification kit spin columns (Bioneer) to isolate band of expected size.

200 ng of digested purified PCR product was ligated with 1 µl T4 ligase and 10 µl Electra buffer (Universal buffer (New England Biolabs)+ATP mix from DNA2.0) in a 100 µl reaction at room temperature for 1 hour. Ligation with T4 DNA ligase joins the first and second ends to generate first circularized polynucleotides (FIG. 5B).

A second restriction endonuclease cleavage and ligation was carried out with type IIs restriction endonuclease SapI to generate second polynucleotides with third and fourth ends that are compatible with the genome modifying vector (SEQ ID NO: 10) as shown in FIG. 5C. 7 µl of first circularized polynucleotide from above was mixed with 1 µl Electra Enzyme mix (SapI and T4 DNA ligase mix, cat # EKT-02 kit, DNA2.0), 1 µl Electra buffer mix (with 10× Universal buffer (New England Biolabs)+10 mM ATP, cat # EKT-02 kit, DNA2.0)), 1 µl of linearized 20 ng/µl genome modifying vector pD1401-AD (SEQ ID NO: 10) from DNA2.0. Reaction was incubated at room temperature for 1 hour. Transformed the entire 10 µl into competent DH10B cells and plated on to LB plates with 100 µg/ml kanamycin. 11 transformants were picked, plasmids isolated from cultures and analyzed by sequencing.

We observed incorporation of nine expected gRNA pairs, one unexpected pair with deletion of 1 base pair at the vector end and one transformant with no insert. Overall, an incorporation rate of 82% was demonstrated for expected gRNA pairs. Further optimization to generate larger libraries and to increase the incorporation efficiency of linked gRNA pairs is expressly contemplated. This demonstrates that it is possible to generate linked gRNA or other linked polynucleotide fragments using the method described herein.

REFERENCES

All references cited herein are incorporated herein by reference in their entirety and for all purposes to the same extent as if each individual publication or patent or patent application was specifically and individually indicated to be incorporated by reference in its entirety for all purposes.

All websites, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Many modifications and variations of this invention can be made without departing from its spirit and scope The specific embodiments described herein are offered by way of example only, and the invention is to be limited only by the terms of the appended claims, along with the full scope of equivalents to which such claims are entitled.

Any feature, step, element, embodiment, or aspect of the invention can be used in combination with any other unless specifically indicated otherwise.

---

The invention claimed is:

1. A method of inserting a plurality of paired nucleic acid segments into molecules of a vector so that different molecules of the vector receive different paired segments, the method comprising
   (a) chemically synthesizing a plurality of oligonucleotides, each comprising paired segments encoding paired guide RNAs, the paired guide RNA's differing among the oligonucleotides;
   (b) performing an assembly reaction between the oligonucleotides and a spacer oligonucleotide comprising a promoter to form nucleic acids in which the spacer oligonucleotide is to one side of the oligonucleotides comprising the paired segments, wherein the assembly reaction is a template-directed amplification performed with a template, forward primer and reverse primers, the spacer oligonucleotide being the template, and the oligonucleotides comprising the paired segments being the reverse primers;
   (c) circularizing the nucleic acids;
   (d) cleaving the circularized nucleic acids at a site that generates linear nucleic acids in each of which the spacer oligonucleotide is flanked by the paired segments with the promoter of the spacer oligonucleotide in operable linkage with one of the paired segments; and
   (e) inserting the linear nucleic acids into molecules of a vector so that different molecules of the vector receive different linear nucleic acids encoding different paired guide RNAs, one of which is in operable linkage with the promoter of the spacer oligonucleotide and the other of which is in operable linkage with a promoter of the vector.

2. The method of claim 1, wherein the 5' ends of the forward and reverse primers are complementary and annealing of these 5' ends or their complements on opposing strands circularizes the nucleic acid.

3. The method of claim 1, wherein the circularized nucleic acids are cleaved in at least one site between the paired segments such that the distance between the paired segments is greater in the linearized nucleic acid than in the circularized nucleic acid.

4. The method of claim 2, wherein the template is double-stranded and the forward primer and reverse primers are single-stranded.

5. The method of claim 1, wherein the promoter of the spacer oligonucleotide is an RNA pol III promoter.

6. The method of claim 5, wherein the spacer further comprises a transcriptional terminator upstream of the promoter.

7. The method of claim 6, wherein the spacer further encodes a scaffold RNA upstream from the terminator wherein one of the guide RNAs and the scaffold RNA are in operable linkage with one another.

8. The method of claim 7, wherein the spacer oligonucleotide comprises a promoter and encodes a scaffold RNA, and the vector comprises a promoter and encodes a scaffold RNA and the vector is adapted such that on insertion of the nucleic acid into a molecule of the vector one guide RNA is operably linked to a scaffold RNA encoded by the spacer and a promoter from the vector and the other guide RNA is operably linked to a scaffold RNA encoded by the vector and the promoter of the spacer.

9. The method of claim 1, wherein the vector encodes a RNA-guided nuclease selected from Cas9, mutant Cas9 with nickase activity (Cas9n) and mutant Cas9 with no activity (dCas9).

10. The method of claim 1, further comprising introducing the molecules of the vector resulting from the method into a host cell, wherein the vector modifies the genome of the host cell and, wherein the host cell is a eukaryotic cell or a bacterial cell.

11. The method of claim 1, wherein: a) the guide RNAs have partially overlapping sequences; and
   b) the guide RNAs are each 15-30 nucleotide long.

12. The method of claim 11, wherein at least 50% of the guide RNA pairs are paired in a pre-determined way.

13. The method of claim 11, wherein the paired segments encode 50 to 100,000 distinct paired guide RNAs.

* * * * *